(12) United States Patent
Herrnstadt et al.

(10) Patent No.: US 6,441,149 B1
(45) Date of Patent: Aug. 27, 2002

(54) DIAGNOSTIC METHOD BASED ON QUANTIFICATION OF EXTRAMITOCHONDRIAL DNA

(75) Inventors: Corinna Herrnstadt; Soumitra S. Ghosh; William Clevenger; Eoin D. Fahy; Robert E. Davis, all of San Diego, CA (US)

(73) Assignee: Mitokor, San Diego, CA (US)

( * ) Notice: Subject to any disclaimer, the term of this patent is extended or adjusted under 35 U.S.C. 154(b) by 0 days.

(21) Appl. No.: 09/302,681

(22) Filed: Apr. 30, 1999

Related U.S. Application Data

(63) Continuation-in-part of application No. 09/097,889, filed on Jun. 15, 1998, now Pat. No. 6,218,117, and a continuation-in-part of application No. 09/098,079, filed on Jun. 15, 1998.

(51) Int. Cl.[7] .................. C07H 21/02; C07H 21/04; C12Q 1/68

(52) U.S. Cl. ................ 536/23.1; 536/24.1; 536/24.3; 435/6

(58) Field of Search .............. 536/23.1, 24.3; 536/24.1; 435/6

(56) References Cited

U.S. PATENT DOCUMENTS

| | | | |
|---|---|---|---|
| 4,683,202 A | 7/1987 | Mullis | 435/91 |
| 5,508,167 A | 4/1996 | Roses et al. | 435/6 |
| 5,840,493 A | 11/1998 | Davis et al. | 435/6 |

FOREIGN PATENT DOCUMENTS

| | | |
|---|---|---|
| EP | 0 594 959 A1 | 5/1994 |
| WO | WO 93/21339 | 10/1993 |
| WO | WO 95/26973 | 10/1995 |
| WO | WO 98/27227 | 6/1998 |

OTHER PUBLICATIONS

Wilson et al, Genbank Accession No. U29157 (Jun. 15, 1995).*
Xu et al, "The complete mitochondrial DNA (mtDNA) of the donkey and the mtDNA comparisons among four closely related mammalian species–pairs", J. Mol. Evolution 443:438–446 (1996).*
Horai et al, "Recent african origin of modern humans revealed by complete sequences of hominoid mitochondrial DNAs", Proc. Natl. Acad. Sci USA 92:532–536, Jan. 1995.*
Fujiwara et al, Genbank Locus C16832, Jan. 1995.*
Davis II and Parker, Jr., "Evidence That Two Reports of mtDNA Cytochrome c Oxidase 'Mutations' in Alzheimer's Diesease Are Based on nDNA Pseudogenes of Recent Evolutionary Origin," Biochemical and Biophysical Research Communications 244:877–833, 1998.
du Manoir et al., "Quantitative Analysis of Comparative Genomic Hybridization," Cytometry 19:27–41, 1995.

Ghosh et al., "Longitudinal Study of a Hetroplasmic 3460 Leber Hereditary Optic Neuropathy Family by Multiplexed Primer–Extension Analysis and Nucleotide Sequencing," Am. J. Hum. Genet. 58325–334, 1996.
Hadler et al., "Genomic Mitochondrial DNA–Like Sequences in Normal and Tumor Tissue of Mouse and Rat," The FASEB Journal 4(3):A764, 1990.
Parfait et al., "Coamplification of Nuclear Pseudogenes and Assessment of Hetroplasmy of Mitochondrial DNA Mutations," Biochemical and Biophysical Research Communications 247:57–59, 1998.
Suzuki et al., "Diabetes with Mitochondrial Gene tRNA$^{LYS}$ Mutation," Diabetes Care, US, American Diabetes Association, Alexandria, VA, 17(2):1428–1432, 1994.
Wallace, "Mitochondrial Genetics: A Paradigm for Aging and Degenerative Diseases?," Science 256:628–632, 1992.
Anderson et al., "Sequence and organization of the human mitochondrial genome," Nature 290: 457–465, 1981.
Antonetti et al., "Increased Expression Of Mitochondrial–Encoded Genes In Skeletal Muscle Of Humans With Diabetes Mellitus," J. Clin. Invest. 95: 1383–1388, 1995.
Boultwood et al., "Amplification Of Mitochondrial DNA In Acute Myeloid Leukaemia," British Journal Of Haematology 95: 426–431, 1996.
Cannizzaro and Shi, Methods in Molecular Biology, vol. 75: Basic Cell Culture Protocols, Humana Press Inc., Totowa, New Jersey, 1997, Chapter 26, "Fluorescent in Situ Hybridization (FISH) for DNA Probes in the Interphase and Metaphase Stages of the Cell Cycle," pp. 313–322.
Corder et al., "Gene Dose of Apolipoprotein E Type 4 Allele and the Risk of Alzheimer's Disease in late Onset Families," Science 261: 921–923, 1993.
Davis et al., "Mutations in mitochondrial cytochrome c oxidase genes segregrate with late–onset Alzheimer disease," Proc. Natl. Acad. Sci. USA 94: 4526–4531, 1997.
DeKosky and Scheff, "Synapse Loss in Frontal Cortex Biopsies in Alzheimer's Disease: Correlation with Cognitive Serverity," Annals of Neurology 27(5): 457–464, 1990.
Fahy et al., "Multiplex fluorescene–based primer extension method for quantitive mutation analysis of mitochondrial DNA and its diagnostic application for Alzheimer's disease," Nucleic Acids Research 25(15): 3102–3109, 1997.
Fossel, "Telomerase and the Aging Cell," JAMA The Journal of the American Medical Association 279(21): 1673–1760, 1998.

(List continued on next page.)

Primary Examiner—Jeffrey Fredman
(74) Attorney, Agent, or Firm—SEED Intellectual Property Law Group, PLLC

(57) ABSTRACT

Compositions and methods based on quantification of extra-mitochondrial DNA (exmtDNA) sequences are provided that are useful for detecting the presence of or risk for having a disease associated with altered mitochondrial function, and for identifying agents suitable for treating such diseases. The exmtDNA sequences have strong homology to authentic mitochondrial DNA (mtDNA) sequences.

2 Claims, 40 Drawing Sheets-

OTHER PUBLICATIONS

Gerbitz et al., "Mitochondria and Diabetes. Genetic, Biocheical, And Clinical Implications Of The Cellular Energy Circuit," *Diabetes 45*: 113–126, 1996.

Gómez–Diaz et al., "Ascorbate Stabilization Is Stimulated in $\rho°$HL–60 Cells by $CoQ_{10}$ Increase at the Plasma Membrane," *Biochemical And Biophysical Research Communications 234*: 79–81, 1997.

Hirano et al., "Apparent mtDNA heteroplamsy in Alzheimer's disease patients and in normals due to PCR amplification of nucleus–embedded mtDNA pseudogenes," *Proc. Natl. Acad. Sci. USA 94*: 14894–14899, 1997.

Iwama et al., "Telomeric length and telomerase activity vary with age in peripheral blood cells obtained from normal individuals," *Human Genetics 102*(4): 397–402, 1998.

LaBranche et al., "Telomere elongation by hnRNP A1 and a derivative that interacts with telomeric repeats and telomerase," *Nature Genetics 19*(2): 199–202, 1998.

Larm et al., "Up–regulation of the Plasma Membrane Oxidoreductase as a Prerequisite for the Viability of Human Namalwa $\rho°$ Cells," *The Journal Of Biological Chemistry 269*(48): 30097–30100, 1994.

Lightowlers et al., "Mammalian Mitochondrial Genetics: Heredity, Heteroplasmy And Disease," *TIG 13*(11): 450–455, 1997.

Lopez et al., "Numt, a Recent Transfer and Tandem Amplificaton of Mitochondrial DNA to the Nuclear Genome of the Domestic Cat," *Journal Of Molecular Evolution 39*: 174–190, 1994.

Marchetti et al., "Apoptosis–associated Derangement of Mitochondrial Function in Cells Lacking Mitochondrial DNA," *Cancer Research 56*(9): 2033–2038, 1996.

Moraes et al., "mtDNA Depletion With Variable Tissue Expression: A Novel Genetic Abnormality In Mitochondrial Diseases," *Am. J. Hum. Genet. 48*: 492–501, 1991.

National Institue on Aging/Alzheimer's Association Working Group, "Apoliprotein E genotyping in Alzheimer's disease," *The Lancet 347*: 1091–1095, 1996.

Nowak et al., "Regulation of Telomerase Activity in Normal and Malignant Human Cells," *The Cancer Journal from Scientific American 4*(3): 148–154, 1998.

Parker, Jr. et al., "Abnormalities of the Electron Transport Chain in Idiopathic Parkinson's Disease," *Ann. Neurol. 26*: 719–723, 1989.

Parnetti et al., "Increased cerebrospinal fluid pyruvate levels in Alzheimer's disease," *Neuroscience Letters 199*: 231–233, 1995.

Poulton et al., "Variation in mitochondrial DNA levels in muscles from normal controls. Is depletion of mtDNA in patients with mitochondrial myopathy a distinct clinical syndrome?," *J. Inher. Metab. Dis. 18*: 4–20, 1995.

Shay et al., "Mitochondrial DNA copy number is proportional to total cell DNA under a variety of growth conditions," *J. Biol. Chem 265*(25):14802–14807, 1990.

Shay, "Telomerase in Cancer: Diagnostic, Prognostic, and Therapeutic Implications," *The Cancer Journal from Scientific American 4*(Supplement 1): S26–S34, 1998.

Swerdlow et al., "Origin And Functional Consequences Of The Complex I Defect In Parkinson's Disease," *Ann. Neurol. 40*:663–671, 1996.

Wallace et al., "Ancient mtDNA sequences in the human nuclear genome: A potential source of errors in identifying pathogenic mutations," *Proc. Natl. Acad. Sci. USA 94*: 14900–14905, 1997.

Williams et al., "Regulation Of Nuclear And Mitochondrial Gene Expression by Contractile Activity In Skeletal Muscle," *The Journal Of Biological Chemistry 261*(1): 376–380, 1986.

Williams, "Mitochondrial Gene Expression In Mammalian Striated Muscles," *The Journal Of Biological Chemistry 261*(26): 12390–12394, 1986.

* cited by examiner

```
cactgtaaag ctaacccagc attaaccttt taagttaaag actaagagaa tcattatctc    60
tttacagtga aatgccacag ctaaatacca ctgtatgacc tgctatcatc accccaatac   120
tcctcacgtt atttctcatc acccaactaa aaatactaaa cacacactgc catctgccca   180
cctcaccaaa atttattaaa ataaaaaact acagtaagcc ctgagaacca aaatgaacga   240
aaatttattc gcttcattca ttacccctac agtactaggc ctacccgcca cagtaccaat   300
catcctatt  ccccccttac tggtcccaac ctccaaatac ctcatcaaca accgactaat   360
caccactcaa caatgactac ttcaactcac cttaaaacaa ataataacga tacataacat   420
taagggacga acctggtccc ttatactaat ttccctgatt attttattg ccacaactaa    480
tctcctcgga ctcttgcccc actcatttac accaatcac                         519
```

```
gatcacaggt ctatcaccct attaaccact cacgggagct ctccatgcat ttggtatttt     60
cgtctggggg gtatgcacgc gatagcattg cgagacgctg gagccggagc accctatgtc    120
gcagtatctg tctttgattc ctgcctcatc ctattattta tcgcacctac gttcaatatt    180
acaggcgaac atacttacta aagtgtgtta attaattaat gcttgtagga cataataata    240
acaattgaat gtctgcacag ccactttcca cacagacatc ataacaaaaa atttccacca    300
aacccccccct cccccgcttc tggccacagc acttaaacac atctctgcca aaccccaaaa    360
acaaagaacc ctaacaccag cctaaccaga tttcaaattt tatctttttgg cggtatgcac    420
ttttaacagt cacccccaa ctaacacatt attttcccct cccactccca tactactaat     480
ctcatcaata caaccccgc ccatcctacc cagcacacac acaccgctgc taaccccata     540
ccccgaacca accaaaccc aaagacaccc cccacagttt atgtagctta cctcctcaaa    600
gcaatacact gaaaatgttt agacgggctc acatcacccc ataaacaaat aggtttggtc    660
ctagcctttc tattagctct tagtaagatt acacatgcaa gcatcccgt tccagtgagt    720
tcaccctcta aatcaccacg atcaaaaggg acaagcatca agcacgcagc aatgcagctc    780
aaaacgctta gcctagccac acccccacgg gaaacagcag tgattaacct ttagcaataa    840
acgaaagttt aactaagcta tactaaccccc agggttggtc aatttcgtgc cagccaccgc    900
ggtcacacga ttaacccaag tcaatagaag ccggcgtaaa gagtgtttta gatcaccccc    960
tccccaataa agctaaaact cacctgagtt gtaaaaaact ccagttgaca caaaatagac   1020
tacgaaagtg gctttaacat atctgaacac acaatagcta agacccaaac tgggattaga   1080
taccccacta tgcttagccc taaaacctcaa cagttaaatc aacaaaactg ctcgccagaa   1140
cactacgagc cacagcttaa aactcaaagg acctggcggt gcttcatatc cctctagagg   1200
agcctgttct gtaatcgata aaccccgatc aacctcacca cctcttgctc agcctatata   1260
ccgccatctt cagcaaaccc tgatgaaggc tacaaagtaa gcgcaagtac ccacgtaaag   1320
acgttaggtc aaggtgtagc ccatgaggtg gcaagaaatg ggctacattt tctaccccag   1380
aaaactacga tagcccttat gaaacttaag ggtcgaaggt ggatttagca gtaaactaag   1440
agtagagtgc ttagttgaac agggccctga agcgcgtaca caccgcccgt caccctcctc   1500
aagtatactt caaaggacat ttaactaaaa cccctacgca tttatataga ggagacaagt   1560
cgtaacatgg taagtgtact ggaaagtgca cttggacgaa ccagagtgta gcttaacaca   1620
aagcacccaa cttacactta ggagatttca acttaacttg accgctctga gctaaaccta   1680
gccccaaacc cactccacct tactaccaga caaccttagc caaaccattt acccaaataa   1740
agtataggcg atagaaattg aaacctggcg caatagatat agtaccgcaa gggaaagatg   1800
aaaaattata accaagcata atatagcaag gactaacccc tatcccttct gcataatgaa   1860
ttaactagaa ataactttgc aaggagagcc aaagctaaga cccccgaaac cagacgagct   1920
acctaagaac agctaaaaga gcacacccgt ctatgtagca aaatagtggg aagatttata   1980
ggtagaggcg acaaacctac cgagcctggt gatagctggt tgtccaagat agaatcttag   2040
ttcaactttta aatttgccca cagaaccctc taaatcccct tgtaaattta actgttagtc   2100
caaagaggaa cagctctttg gacactagga aaaaaccttg tagagagagt aaaaaattta   2160
acacccatag taggcctaaa agcagccacc aattaagaaa gcgttcaagc tcaacaccca   2220
ctacctaaaa aatcccaaac atataactga actcctcaca cccaattgga ccaatctatc   2280
accctataga agaactaatg ttagtataag taacatgaaa acattctcct ccgcataagc   2340
ctgcgtcaga ttaaaacact gaactgacaa ttaacagccc aatatctaca atcaaccaac   2400
aagtcattat taccctcact gtcaacccaa cacaggcatg ctcataagga aaggttaaaa   2460
aaagtaaaag gaactcggca aatcttaccc cgcctgttta ccaaaaacat cacctctagc   2520
atcaccagta ttagaggcac cgcctgccca gtgacacatg tttaacggcc gcggtaccct   2580
aaccgtgcaa aggtagcata atcacttgtt ccttaaatag ggacctgtat gaatggctcc   2640
acgagggttc agctgtctct tactttttaac cagtgaaatt gacctgcccg tgaagaggcg   2700
ggcataacac agcaagacga gaagacccta tggagcttta atttattaat gcaaacagta   2760
cctaacaaac ccacaggtcc taaactacca aacctgcatt aaaaatttcg gttggggcga   2820
cctcggagca gaacccaacc tccgagcagt acatgctaag acttcaccag tcaaagcgaa   2880
ctactatact caattgatcc aataacttga ccaacggaac aagttaccct agggataaca   2940
gcgcaatcct attctagagt ccatatcaac aatagggttt acgacctcga tgttggatca   3000
ggacatcccg atggtgcagc cgctattaaa ggttcgtttg ttcaacgatt aaagtcctac   3060
gtgatctgag ttcagaccgg agtaatccag gtcggttttct atctaccttc aaattcctcc   3120
ctgtacgaaa ggacaagaga aataaggcct acttcacaaa gcgccttccc ccgtaaatga   3180
tatcatctca acttagtatt atacccacac ccacccaaga cagggtttg ttaagatggc   3240
agagcccggt aatcgcataa aacttaaaac tttacagtca gaggttcaat tcctcttctt   3300
aacaacatac ccatggccaa cctcctactc ctcattgtac ccattctaat cgcaatggca   3360
ttcctaatgc ttaccgaacg aaaaattcta ggctatatac aactacgcaa aggccccaac   3420
gttgtaggcc cctacgggct actacaaccc ttcgctgacg ccataaaact cttcaccaaa   3480
```

Fig. 2B

```
gagcccctaa aacccgccac atctaccatc accctctaca tcaccgcccc gaccttagct 3540
ctcaccatcg ctcttctact atgaacccccc ctccccatac ccaacccccct ggtcaacctc 3600
aacctaggcc tcctatttat tctagccacc tctagcctag ccgtttactc aatcctctga 3660
tcagggtgag catcaaactc aaactacgcc ctgatcggcg cactgcgagc agtagcccaa 3720
acaatctcat atgaagtcac cctagccatc attctactat caacattact aataagtggc 3780
tcctttaacc tctccaccct tatcacaaca caagaacacc tctgattact cctgccatca 3840
tgacccttgg ccataatatg atttatctcc acactagcag agaccaaccg aaccccccttc 3900
gaccttgccg aaggggagtc cgaactagtc tcaggcttca acatcgaata cgccgcaggc 3960
cccttcgccc tattcttcat agccgaatac acaaacatta ttataataaa caccctcacc 4020
actacaatct tcctaggaac aacatatgac gcactctccc ctgaactcta cacaacatat 4080
tttgtcacca agaccctact tctaacctcc ctgttcttat gaattcgaac agcatacccc 4140
cgattccgct acgaccaact catacacctc ctatgaaaaa acttcctacc actcacccta 4200
gcattactta tatgatatgt ctccataccc attacaatct ccagcattcc ccctcaaacc 4260
taagaaatat gtctgataaa agagttactt tgatagagta aataatagga gcttaaaccc 4320
ccttatttct aggactatga gaatcgaacc catccctgag aatccaaaat tctccgtgcc 4380
acctatcaca ccccatccta aagtaaggtc agctaaataa gctatcgggc ccataccccg 4440
aaaatgttgg ttatacccttt cccgtactaa ttaatcccct ggcccaaccc gtcatctact 4500
ctaccatctt tgcaggcaca ctcatcacag cgctaagctc gcactgattt tttacctgag 4560
taggcctaga aataaacatg ctagcttttta ttccagttct aaccaaaaaa ataaaccctc 4620
gttccacaga agctgccatc aagtatttcc tcacgcaagc aaccgcatcc ataatccttc 4680
taatagctat cctcttcaac aatatactct ccggacaatg aaccataacc aatactacca 4740
atcaatactc atcattaata atcataatag ctatagcaat aaaactagga atagcccct 4800
ttcacttctg agtcccagag gttacccaag gcacccctct gacatccggc ctgcttcttc 4860
tcacatgaca aaaactagcc cccatctcaa tcatatacca aatctctccc tcactaaacg 4920
taagcctttc cctcactctc tcaatcttat ccatcatagc aggcagttga ggtggattaa 4980
accagaccca gctacgcaaa atcttagcat actcctcaat tacccacata ggatgaataa 5040
tagcagttct accgtacaac cctaacataa ccattcttaa tttaactatt tatattatcc 5100
taactactac cgcattccta ctactcaact taaactccag caccacgacc ctactactat 5160
ctcgcacctg aaacaagcta acatgactaa cacccttaat tccatccacc ctcctctccc 5220
taggaggcct gcccccgcta accggctttt tgcccaaatg ggccattatc gaagaattca 5280
caaaaaacaa tagcctcatc atccccacca tcatagccac catcaccctc cttaacctct 5340
acttctacct acgcctaatc tactccacct caatcacact actccccata tctaacaacg 5400
taaaaataaa atgacagttt gaacatacaa aacccacccc attcctcccc acactcatcg 5460
cccttaccac gctactccta cctatctccc cttttatact aataatctta tagaaattta 5520
ggttaaatac agaccaagag ccttcaaagc cctcagtaag ttgcaatact aatttctgt 5580
aacagctaag gactgcaaaa ccccactctg catcaactga acgcaaatca gccactttaa 5640
ttaagctaag cccttactag accaatggga cttaaaccca caaacactta gttaacagct 5700
aagcacccta atcaactggc ttcaatctac ttctcccgcc gccgggaaaa aaggcgggag 5760
aagccccggc aggtttgaag ctgcttcttc gaatttgcaa ttcaaatga aaatcacctc 5820
ggagctggta aaaagaggcc taacccctgt ctttagattt acagtccaat gcttcactca 5880
gccatttac ctcaccccca ctgatgttcg ccgaccgttg actattctct acaaaccaca 5940
aagacattgg aacactatac ctattattcg gcgcatgagc tggagtccta ggcacagctc 6000
taagcctcct tattcgagcc gagctgggcc agccaggcaa ccttctaggt aacgaccaca 6060
tctacaacgt tatcgtcaca gcccatgcat ttgtaataat cttcttcata gtaatacccca 6120
tcataatcgg aggctttggc aactgactag ttcccctaat aatcggtgcc cccgatatgg 6180
cgtttccccg cataaacaac ataagcttct gactcttacc tccctctctc ctactcctgc 6240
tcgcatctgc tatagtggag gccggagcag gaacaggttg aacagtctac cctcccttag 6300
cagggaacta ctcccacct ggagcctccg tagacctaac catcttctcc ttacacctag 6360
caggtgtctc ctctatctta ggggccatca atttcatcac aacaattatc aatataaaac 6420
ccccctgccat aacccaatac caaacgcccc tcttcgtctg atccgtccta atcacagcag 6480
tcctacttct cctatctctc ccagtcctag ctgctggcat cactatacta ctaacagacc 6540
gcaacctcaa caccaccttc ttcgacccccg ccggaggagg agaccccatt ctataccaac 6600
acctattctg atttttcggt caccctgaag tttatattct tatcctacca ggcttcggaa 6660
taatctccca tattgtaact tactactccg gaaaaaaaga accatttgga tacataggta 6720
tggtctgagc tatgatatca attggcttcc tagggtttat cgtgtgagca caccatatat 6780
ttacagtagg aatagacgta gacacacgag catattcac ctccgctacc ataatcatcg 6840
ctatccccac cggcgtcaaa gtatttagct gactcgccac actccacgga agcaatatga 6900
aatgatctgc tgcagtgctc tgagccctag gattcatctt tcttttcacc gtaggtggcc 6960
```

Fig. 2C

```
tgactggcat tgtattagca aactcatcac tagacatcgt actacacgac acgtactacg    7020
ttgtagccca cttccactat gtcctatcaa taggagctgt atttgccatc ataggaggct    7080
tcattcactg atttccccta ttctcaggct acaccctaga ccaaacctac gccaaaatcc    7140
atttcactat catattcatc ggcgtaaatc taactttctt cccacaacac tttctcggcc    7200
tatccggaat gccccgacgt tactcggact accccgatgc atacaccaca tgaaacatcc    7260
tatcatctgt aggctcattc atttctctaa cagcagtaat attaataatt ttcatgattt    7320
gagaagcctt cgcttcgaag cgaaaagtcc taatagtaga agaaccctcc ataaacctgg    7380
agtgactata tggatgcccc ccaccctacc acacattcga agaacccgta tacataaaat    7440
ctagacaaaa aaggaaggaa tcgaaccccc caaagctggt ttcaagccaa ccccatggcc    7500
tccatgactt tttcaaaaag gtattagaaa aaccatttca taactttgtc aaagttaaat    7560
tataggctaa atcctatata tcttaatggc acatgcagcg caagtaggtc tacaagacgc    7620
tacttcccct atcatagaag agcttatcac ctttcatgat cacgccctca taatcatttt    7680
ccttatctgc ttcctagtcc tgtatgccct tttcctaaca ctcacaacaa aactaactaa    7740
tactaacatc tcagacgctc aggaaataga aaccgtctga actatcctgc ccgccatcat    7800
cctagtcctc atcgccctcc catccctacg catcctttac ataacagacg aggtcaacga    7860
tccctcccttt accatcaaat caattggcca ccaatggtac tgaacctacg agtacaccga    7920
ctacggcgga ctaatcttca actcctacat acttccccca ttattcctag aaccaggcga    7980
cctgcgactc cttgacgttg acaatcgagt agtactcccg attgaagccc ccattcgtat    8040
aataattaca tcacaagacg tcttgcactc atgagctgtc cccacattag gcttaaaaac    8100
agatgcaatt cccggacgtc taaaccaaac cactttcacc gctacacgac cgggggtata    8160
ctacggtcaa tgctctgaaa tctgtggagc aaaccacagt ttcatgccca tcgtcctaga    8220
attaattccc ctaaaaatct ttgaataggg cccgtatttt accctatagc acccccctcta    8280
ccccctctag agcccactgt aaagctaact tagcattaac cttttaagtt aaagattaag    8340
agaaccaaca cctctttaca gtgaaatgcc ccaactaaat actaccgtat ggcccaccat    8400
aattaccccc atactcctta cactattcct catcacccaa ctaaaaatat taaacacaaa    8460
ctaccaccta cctccctcac caaagcccat aaaaataaaa aattataaca aaccctgaga    8520
accaaaatga acgaaaatct gttcgcttca ttcattgccc ccacaatcct aggcctaccc    8580
gccgcagtac tgatcattct atttccccct ctattgatcc ccacctccaa atatctcatc    8640
aacaaccgac taatcaccac ccaacaatga ctaatcaaac taacctcaaa acaaatgata    8700
accatacaca acactaaagg acgaacctga tctcttatac tagtatcctt aatcattttt    8760
attgccacaa ctaacctcct cggactcctg cctcactcat ttacaccaac cacccaacta    8820
tctataaacc tagccatggc catcccctta tgagcgggca cagtgattat aggctttcgc    8880
tctaagatta aaaatgccct agcccacttc ttaccacaag gcacacctac acccctttatc    8940
cccatactag ttattatcga aaccatcagc ctactcattc aaccaatagc cctggccgta    9000
cgcctaaccg ctaacattac tgcaggccac ctactcatgc acctaattgg aagcgccacc    9060
ctagcaatat caactcccct acacttcacaat tcttcacaat tctaattcta    9120
ctgactatcc tagaaatcgc tgtcgcctta atccaagcct acgttttcac acttctagta    9180
agcctctacc tgcacgacaa cacataatga cccaccaatc acatgcctat catatagtaa    9240
aacccagccc atgaccccta acagggggccc tctcagcсcсt cctaatgacc tccggcctag    9300
ccatgtgatt tcacttccac tccataacgc tcctcatact aggcctacta accaacacac    9360
taaccatata ccaatgatgg cgcgatgtaa cacgagaaag cacataccaa ggccaccaca    9420
caccacctgt ccaaaaaggc cttcgatacg ggataatcct atttattacc tcagaagttt    9480
ttttcttcgc aggatttttc tgagcctttt accactccag cctagcccct acccccсcaat    9540
taggagggca ctggccccca acaggcatca ccccgctaaa tcccctagaa gtcccactcc    9600
taaacacatc cgtattactc gcatcaggag tatcaatcac ctgagctcac catagtctaa    9660
tagaaaacaa ccgaaaccaa ataattcaag cactgcttat tacaatttta ctgggtctct    9720
attttaccct cctacaagcc tcagagtact tcgagtctcc cttcaccatt tccgacggca    9780
tctacggctc aacattttt gtagccacag gcttccacgg acttcacgtc attattggct    9840
caactttcct cactatctgc ttcatccgcc aactaatatt tcactttaca tccaaacatc    9900
actttggctt cgaagccgcc gcctgatact ggcattttgt agatgtggtt tgactatttc    9960
tgtatgtctc catctattga tgagggtctt actcttttag tataaatagt accgttaact   10020
tccaattaac tagttttgac aacattcaaa aagagtaat aaacttcgcc ttaattttaa    10080
taatcaacac cctcctagcc ttactactaa taattattac atttgacta ccacaactca   10140
acggctacat agaaaaatcc accccttacg agtgcggctt cgaccctata tcccccgccc   10200
gcgtccccttt ctccataaaa ttcttcttag tagctattac cttcttatta tttgatctag   10260
aaattgccct ccttttaccc ctaccatgag ccctacaaac aactaacctg ccactaatag   10320
ttatgtcatc cctcttatta atcatcatcc tagccctaag tctggcctat gagtgactac   10380
aaaaaggatt agactgaacc gaattggtat atagtttaaa caaaacgaat gatttcgact   10440
```

Fig. 2D

```
cattaaatta tgataatcat atttaccaaa tgcccctcat ttacataaat attatactag  10500
catttaccat ctcacttcta ggaatactag tatatcgctc acacctcata tcctccctac  10560
tatgcctaga aggaataata ctatcgctgt tcattatagc tactctcata accctcaaca  10620
cccactccct cttagccaat attgtgccta ttgccatact agtctttgcc gcctgcgaag  10680
cagcggtggg cctagcccta ctagtctcaa tctccaacac atatggccta gactacgtac  10740
ataacctaaa cctactccaa tgctaaaact aatcgtccca acaattatat tactaccact  10800
gacatgactt tccaaaaaac acataatttg aatcaacaca accacccaca gcctaattat  10860
tagcatcatc cctctactat tttttaacca aatcaacaac aacctattta gctgttcccc  10920
aaccttttcc tccgacccccc taacaacccc cctcctaata ctaactacct gactcctacc  10980
cctcacaatc atggcaagcc aacgccactt atccagtgaa ccactatcac gaaaaaaact  11040
ctacctctct atactaatct ccctacaaat ctccttaatt ataacattca agccacaga  11100
actaatcata ttttatatct tcttcgaaac cacacttatc cccaccttgg ctatcatcac  11160
ccgatgaggc aaccagccag aacgcctgaa cgcaggcaca tacttcctat tctacacct  11220
agtaggctcc cttcccctac tcatcgcact aatttacact cacaacaccc taggctcact  11280
aaacattcta ctactcactc tcactgccca agaactatca aactcctgag ccaataactt  11340
aatatgacta gcttacacaa tagcttttat agtaaagata cctctttacg gactccactt  11400
atgactccct aaagcccatg tcgaagcccc catcgctggg tcaatagtac ttgccgcagt  11460
actcttaaaa ctaggcggct atggtataat acgcctcaca ctcattctca accccctgac  11520
aaaacacata gcctacccct tccttgtact atccctatga ggcataatta taacaagctc  11580
catctgccta cgacaaacag acctaaaatc gctcattgca tactcttcaa tcagccacat  11640
agccctcgta gtaacagcca ttctcatcca acccccctga agcttcaccg gcgcagtcat  11700
tctcataatc gcccacgggc ttacatcctc attactattc tgcctagcaa actcaaacta  11760
cgaacgcact cacagtcgca tcataatcct ctctcaagga cttcaaactc tactcccact  11820
aatagctttt tgatgacttc tagcaagcct cgctaacctc gccttacccc ccactattaa  11880
cctactggga gaactctctg tgctagtaac cacgttctcc tgatcaaata tcactctcct  11940
acttacagga ctcaacatac tagtcacagc cctatactcc ctctacatat ttaccacaac  12000
acaatggggc tcactcaccc accacattaa caacataaaa ccctcattca cacgagaaaa  12060
caccctcatg ttcatacacc tatcccccat tctcctccta tccctcaacc ccgacatcat  12120
taccgggttt tcctcttgta aatatagttt aaccaaaaca tcagattgtg aatctgacaa  12180
cagaggctta cgaccccctta tttaccgaga aagctcacaa gaactgctaa ctcatgcccc  12240
catgtctaac aacatggctt tctcaacttt taaaggataa cagctatcca ttggtcttag  12300
gccccaaaaa ttttggtgca actccaaata aaagtaataa ccatgcacac tactataacc  12360
accctaaccc tgacttccct aattccccccc atccttacca ccctcgttaa ccctaacaaa  12420
aaaaactcat accccccatta tgtaaaatcc attgtcgcat ccaccttttat tatcagtctc  12480
ttcccccacaa caatattcat gtgcctagac caagaagtta ttatctcgaa ctgacactga  12540
gccacaaccc aaacaaccca gctctcccta agcttcaaac tagactactt ctccataata  12600
ttcatccctg tagcattgtt cgttacatgg tccatcatag aattctcact gtgatatata  12660
aactcagacc caaacattaa tcagttcttc aaatatctac tcatcttcct aattaccata  12720
ctaatcttag ttaccgctaa caaccattc caactgttca tcggctgaga gggcgtagga  12780
attatatcct tcttgctcat cagttgatga tacgcccgag cagatgccaa cacagcagcc  12840
attcaagcaa tcctatacaa ccgtatcggc gatatcggtt tcatcctcgc cttagcatga  12900
tttatcctac actccaactc atgagaccca caacaaatag cccttctaaa cgctaatcca  12960
agcctcaccc cactactagg cctcctccta gcagcagcag gcaaatcagc ccaattaggt  13020
ctccaccccct gactcccctc agccatagaa ggccccaccc cagtctcagc cctactccac  13080
tcaagcacta tagttgtagc aggaatcttc ttactcatcc gcttccaccc cctagcagaa  13140
aatagcccac taatccaaac tctaacacta tgcttaggcg ctatcaccac tctgttcgca  13200
gcagtctgcg cccttacaca aaatgacatc aaaaaaatcg tagccttctc cacttcaagt  13260
caactaggac tcataatagt tacaatcggc atcaaccaac cacacctagc attcctgcac  13320
atctgtaccc acgccttctt caaagccata ctatttatgt gctccgggtc catcatccac  13380
aaccttaaca atgaacaaga tattcgaaaa ataggaggac tactcaaaac catacctctc  13440
acttcaacct ccctcaccat tggcagccta gcattagcag gaatacccttt cctcacaggt  13500
ttctactcca aagaccacat catcgaaacc gcaaacatat catacacaaa cgcctgagcc  13560
ctatctatta ctctcatcgc tacctccctg acaagcgcct atagcactcg aataattctt  13620
ctcaccctaa caggtcaacc tcgcttcccc acccttacta acattaacga aaataacccc  13680
accctactaa accccattaa acgcctggca gccggaagcc tattcgcagg atttctcatt  13740
actaacaaca tttcccccgc atccccctcc aaacaacaa tcccccctcta cctaaaactc  13800
acagccctcg ctgtcacttt cctaggactt ctaacagccc tagacctcaa ctacctaacc  13860
aacaaactta aaataaaatc cccactatgc acattttatt tctccaacat actcggattc  13920
```

```
taccctagca tcacacaccg cacaatcccc tatctaggcc ttcttacgag ccaaaacctg   13980
cccctactcc tcctagacct aacctgacta gaaaagctat tacctaaaac aatttcacag   14040
caccaaatct ccacctccat catcacctca acccaaaaag gcataattaa actttacttc   14100
ctctctttct tcttcccact catcctaacc ctactcctaa tcacataacc tattcccccg   14160
agcaatctca attacaatat atacaccaac aaacaatgtt caaccagtaa ctactactaa   14220
tcaacgccca taatcataca aagcccccgc accaatagga tcctcccgaa tcaaccctga   14280
cccctctcct tcataaatta ttcagcttcc tacactatta aagtttacca caaccaccac   14340
cccatcatac tctttcaccc acagcaccaa tcctacctcc atcgctaacc ccactaaaac   14400
actcaccaag acctcaaccc ctgaccccca tgcctcagga tactcctcaa tagccatcgc   14460
tgtagtatat ccaaagacaa ccatcattcc ccctaaataa attaaaaaaa ctattaaacc   14520
catataacct cccccaaaat tcagaataat aacacacccg accacaccgc taacaatcaa   14580
tactaaaccc ccataaatag gagaaggctt agaagaaaac cccacaaacc ccattactaa   14640
acccacactc aacagaaaca aagcatacat cattattctc gcacggacta caaccacgac   14700
caatgatatg aaaaaccatc gttgtatttc aactacaaga acaccaatga ccccaatacg   14760
caaaattaac cccctaataa aattaattaa ccactcattc atcgacctcc cacccccatc   14820
caacatctcc gcatgatgaa acttcggctc actccttggc gcctgcctga tcctccaaat   14880
caccacagga ctattcctag ccatgcacta ctcaccagac gcctcaaccg ccttttcatc   14940
aatcgcccac atcactcgag acgtaaatta tggctgaatc atccgctacc ttcacgccaa   15000
tggcgcctca atattcttta tctgcctctt cctacacatc gggcgaggcc tatattacgg   15060
atcatttctc tactcagaaa cctgaaacat cggcattatc ctcctgcttg caactatagc   15120
aacagccttc ataggctatg tcctcccgtg aggccaaata tcattctgag ggccacagt   15180
aattacaaac ttactatccg ccatcccata cattgggaca gacctagttc aatgaatctg   15240
aggaggctac tcagtagaca gtcccaccct cacacgattc tttacctttc acttcatctt   15300
gcccttcatt attgcagccc tagcaacact ccacctccta ttcttgcacg aaacgggatc   15360
aaacaacccc ctaggaatca cctcccattc cgataaaatc accttccacc cttactacac   15420
aatcaaagac gccctcggct tacttctctt ccttctctcc ttaatgacat taacactatt   15480
ctcaccagac ctcctaggcg acccagacaa ttatacccta gccaaccct taaacacccc   15540
tccccacatc aagcccgaat gatatttcct attcgcctac acaattctcc gatccgtccc   15600
taacaaacta ggaggcgtcc ttgccctatt actatccatc ctcatcctag caataatccc   15660
catcctccat atatccaaac aacaaagcat aatatttcgc ccactaagcc aatcacttta   15720
ttgactccta gccgcagacc tcctcattct aacctgaatc ggaggacaac cagtaagcta   15780
ccctttacc atcattggac aagtagcatc cgtactatac ttcacaacaa tcctaatcct   15840
aataccaact atctccctaa ttgaaaacaa aatactcaaa tgggcctgtc cttgtagtat   15900
aaactaatac accagtcttg taaaccggag atgaaaacct ttttccaagg acaaatcaga   15960
gaaaagtct ttaactccac cattagcacc caaagctaag attctaattt aaactattct   16020
ctgttctttc atggggaagc agatttgggt accacccaag tattgactca cccatcaaca   16080
accgctatgt atttcgtaca ttactgccag ccaccatgaa tattgtacgg taccataaat   16140
acttgaccac ctgtagtaca taaaaaccca atccacatca aaacccctc cccatgctta   16200
caagcaagta cagcaatcaa ccctcaacta tcacacatca actgcaactc aaaagccacc   16260
cctcacccac taggatacca acaaacctac ccacccttaa cagtacatag tacataaagc   16320
catttaccgt acatagcaca ttacagtcaa atcccttctc gtcccatgg atgacccccc   16380
tcagatgggg gtcccttgac caccatcctc cgtgaaatca atatcccgca caagagtgct   16440
actctcctcg ctccgggccc ataacacttg ggggtagcta aagtgaactg tatccgacat   16500
ctggttccta cttcagggtc ataaagccta aatagcccac acgttcccct taaataagac   16560
atcacgatg                                                           16569
```

```
ataggcattc caactcatcc gcttgctgac gacctccacg tgatttcaac aatgatttca      60
aatatttcac tttttaagtc agtgtgactt aagtatgaaa ttgcctctcc ctaaagctcc     120
cctaaggcct aaacagtcgt cattaccata gctgtgacag ggagactgtt gaatttataa     180
tctattggcc attcacagca tagcgtataa accctagctc atgatttctt tgcaatagaa     240
gtgtactttt tcatcacatt cccttcacaa cttactcacc agacagactt tgagctctcc     300
tcctggctta gcctggatcg tttgaaatgg tcatccatcc tttggcccca atacctaaac     360
taaggtctat gaacaataag atgattttac ttcagtggga cttttttgtt taatatatta     420
gatttgacct tcagcaaggt caaagggagt ccgaactagt ctcaggcttc aacatcgaat     480
acgccgcagg nccettcgcc ctattcttca tagccgaata cacaaacatt attataataa     540
acaccctcac cactacaatc ttcctaggaa caacatataa cgcactctcc cctgaactct     600
acacaacata ttttgtcacc aagaccctac ttctgacctc cctgttctta tgaattcgaa     660
cagcataccc ccgattccgc tacgaccaac tcatacacct cctatgaaaa aacttcctac     720
cactcaccct agcattactt atatgatatg tctccatacc cattacaatc tccagcattc     780
ccccctcaaac ctaagaaata tgtctgataa aagagttact ttgatagagt aaataatagg     840
agtttaaatc cccttatttc taggactatg agaatcgaac ccatccctga gaatccaaaa     900
ttctcggtgc caactatcac accccatctt aaagtaaggt cagctaaata agctatcggg     960
cccataccc gaaaatgttg gttatatcct tcccgtacta attaatcccc tggccctaacc    1020
cgtcatttac tctaccatct ttgcaggcac actcatcaca gcgctaagct cgcactgatt    1080
ttttacctga gtaggcctag aaataaacat gctagcttt attccagttc taaccaaaaa    1140
aataaaccct cgttccacag aagntgccat caagtatttc ctcacgcaag caaccgcatc    1200
cataatcctt ctaatagcta tcctnttcaa caatatactc tccggacaat gaaccatwac    1260
caataccacc aatcaatact catcattaat aatcataatg gctatagcaa taaaactagg    1320
aatagccccc tttcacttct gagtcccaga ggttacccaa ggcacccctc tgacatccgg    1380
cctgctcctt ctcacatgac aaaaactagc ccccatctca atcatatacc aaatttctcc    1440
ctcattaaac gtaagccttc tcctcactct ttcaatctta tccatcatgg caggcagttg    1500
aggtggatta aaccaaaccc aactacgcaa aatcttagca tactcctcaa ttacccacat    1560
aggatgaata acagcagttc taccgtacaa ccctaacata accattctta atttaactat    1620
ttatattatc ctaactacta ccgcattcct actactcaac ttaaactcca gcaccacaac    1680
cctactacta tctcgcacct gaaacaagct aacatgacta acacccttaa ttccatccac    1740
cctcctctcc ctaggaggcc tgcccccgct aaccggcttt tgcccaaat gggccattat    1800
cgaagaattc acaaaaaaca atagcctcat catccccacc atcatagcca tcatcaccct    1860
ccttaacctc tacttctacc tgcgcctaat ctactccacc tcaatcacac tactccctat    1920
atctaacaac gtaaaaataa aatgacagtt tgaacacaca aaacccaccc cattcctccc    1980
cacactcatc gcccttacca cactgctcct acctatctcc ccttttatgc taataatctt    2040
atagaaattt aggttaaata cagaccaaga gccttcaaag ccctcagtaa gttgcaatac    2100
ttaatttctg naacagctaa ggactgcaaa accccactct gcatcaactg nangcaaatc    2160
agccacttta attaagctaa gcccttacta gaccaatggg acttaaaccc acaaacactt    2220
agttaacagc taagcaccct aatcaactgg cttcaatcta cttctcccgc cgccgggaaa    2280
aaaggcggga gaagccccgg caggtttgaa gctgcttctt cgaatttgca attcaatatg    2340
aaaatcacct canagctggt aaaaagaggc ttaacccctg tctttagatt tacagtccaa    2400
tgcttcactc agccatttta cctcacccc actgatgttc gccgaccgtt gactattctc    2460
tacaaaccac aaagacattg gaacactata cctattattc ggcgcatgag ctggagtcct    2520
aggcacagct ctaagcctcc ttattcgagc cgaactgggc cagccaggca accttctagg    2580
taacgaccac atctacaacg ttatcgtcac agcccatgca tttgtaataa tcttcttcat    2640
agtaataccc atcataatcg gaggytttgg caastgacta gttccctaa taatcggtgc    2700
ccccgatatg gsgtttcccc gcataaacaa cataagcttn tgactcttac ccccctctct    2760
cntactcctg ttngcatctg ctatagtgga ggccggcgca ggaacaggtt gaacagtnta    2820
ccctcccttg gcagggaact actcccaccc tggagcctcc gtagacctaa ccatcttctc    2880
cttacaccta gcaggtatct cctctatctt agggaccatc aatttcatca caacaattat    2940
taatataaaa ccccctgcca taacccaata ccaaacgccc ctttcgtct gatccgtcct    3000
aatcacagca gtcttacttc tcctatctct cccagtccta gccgctggca tcactatact    3060
actaacagac cgtaaccctca acaccacctt cttcgaccca gccggaggag gagacccccat    3120
tctataccaa cacctattct gatttttcgg tcaccctgaa gtttatattc tcatcctacc    3180
aggcttcgga ataatctccc atattgtaac ttactactcc ggaaaaaaag aaccatttgg    3240
atacataggt atggtctgag ctatgatatc aattggcttc ctaggttta tcgtgtgagc    3300
acaccatata tttacagtag gaatagacgt agacacacga gcatatttca cctccgctac    3360
cataatcatc gctatcccca ccggcgtcaa agtatttagc tgactcgcca cactccacgg    3420
aagcaatatg aaatgatctg ctgcagtgct ctgagcccta ggatttattt ttctttttcac    3480
```

```
cgtaggtggc ctgactggca ttgtattagc aaactcatca ctagacatcg tactacacga   3540
cacgtactac gttgtagccc acttccacta tgtcctatca ataggagctg tatttgccat   3600
cataggaggc ttcattcact gatttcccct attctcaggc tacaccctag accaaaccta   3660
cgccaaaatc catttcgcta tcatattcat cggcgtaaat ctaactttct tcccacaaca   3720
ctttctcggc ctatccggaa tgccccgacg ttactcggac tatcccgatg catacaccac   3780
atgaaatatc ctatcatctg taggctcatt catttctcta acagcagtaa tattaataat   3840
tttcataatt tgagaagcct tcgcttcgaa gcgaaaagtc ctaatagtag aagaaccctc   3900
cataaacctg gagtgactat atggatgccc ccaccctac cacacattcg aagaacccgt   3960
atacataaaa tctagacaaa aaaggaagga atcgaacccc ccaaagctgg tttcaagcca   4020
accccatggc ctccatgact ttttcaaaaa gatattagaa aaaccatttc ataactttgt   4080
caaagttaaa ttataggcta aatcctatat atcttaatgg cacatgcagc gcaagtaggt   4140
ctacaagacg ctacttcccc tatcatagaa gagcttatca tctttcatga tcacgccctc   4200
ataatcattt tccttatctg cttcctagtc ctgtacgccc ttttcctaac actcacaaca   4260
aaactaacta atactaacat ctcagacgct caggaaatag aaaccgtctg aactatcctg   4320
cccgccatca tcctagtcct tatcgccctc ccatncctac gcatccttta cataacagac   4380
gaggtcaacg atccctcctt taccatcaaa tcaattggcc atcaatggta ctgaacctac   4440
gaatacaccg actacggcgg actaatcttc aactcctaca tacttccccc attattccta   4500
gaaccaggcg acctgcgact ccttgacgtt gacaatcgag tagtactccc ggttgaagcc   4560
cccattcgta taataattac atcacaagac gtcttacact catgagctgt ccccacatta   4620
ggcttaaaaa cagatgcaat tcccggacgt ctaaaccaaa ccactttcac tgctacacga   4680
ccagggggtat actacggcca atgctctgaa atctgtggag caaaccagtt ttatgcccat   4740
cgtcctagaa ttaattcccc taaaaatctt tgaaataggg cccgtattta ccctatagca   4800
ccccctctac cccctctaga gcccactgta aagctaactt agcattaacc ttttaagtta   4860
aagattaaga gaaccaacac ctctttacag tgaaatgccc caactaaata ctaccgtatg   4920
acccaccata attacccca tactccttac actattcctc atcacccaac taaaaatatt   4980
aaatacaaat taccacctac ctccctcacc aaagcccata aaaataaaaa actataacaa   5040
accctgagaa ccaaaatgaa cgaaaatctg ttcacttcat tcattgcccc cacaatccta   5100
ggcctacccg ccgcagtact gatcattcta ttyccccctc tattgatccc cacctccaaa   5160
tatctcatca acaaccgact aattaccacc caacaatgac taatccaact aacctcaaaa   5220
caaatgatag ccatacacaa cactaaggga cgaacctgat ctcttatact agtatcctta   5280
atcatttta ttgccacaac taacctcctc ggactcctgc ctcactcatt tacaccaacc   5340
acccaactat ctataaacct agccatggcc atcccttat gagcgggcgc agtgattata   5400
ggctttcgct ctaagattaa aaatgcccta gcccacttct taccacaagg cacacctaca   5460
cccccttatcc ctatactagt tattatcgaa accatcagcc tactcattca accaatagcc   5520
ctggccgtan gnctaaccgc taacattact gcaggccacc tactcatgna cctaattgga   5580
agcgccacac tagcaatatc aantattaac cttccctcta cacttatcat tttcacaatt   5640
ctaattctac tgactatcct agaaatcgct gtcgccttaa tccaagccta cgtttttaca   5700
ctttttagtaa gcctctacct gcacgacaac acataatgac ccaccaatca catgcctatc   5760
atatagtaaa acccagccca tggcccctaa caggggcct ctcanccctc ctaatgacct   5820
ccggcctagc catgtgattt cacttccact ccacaaccct ccttatacta ggcctactaa   5880
ccaacacact aaccatatac caatgatggc gcgatgtaac acgagaaagc acataccaag   5940
gccaccacac accacctgtc cagaaaggcc ttcgatacgg gataatccta tttattacct   6000
ccccccaact aggggggacac tggcccccaa caggcatcac cccgctaaat cccctagaag   6060
tccccactcct aaacacatcc gtattactcg catcaggggt atcaatcacc tgagctcacc   6180
atagtctaat agaaaacaac cgaaaccaaa taattcaagc actgcttatt acaattttac   6240
tgggtctcta ttttaccctc ctacaagcct cagngtactt cgaggttaaa atattagata   6300
tttcccctga tacagggctc aatcttttc tttttaaagc aatatttctc aaagtacttt   6360
tcacagaact taagtttcat taagcacttc actaaaagna aaagtctgtg atctaataaa   6420
tttggaaaat attgagaatt agagcccct cttagatatg tactgtagct actcagcttg   6480
ttacagatgg aagtaaacat tgtaatattc acccagcttt tgagtggatg tctattaaca   6540
tcacccaaat gagtattcca tggaatgcac tttgcaaaaa cctattattc aagaaaaatt   6600
ctggagcatg gaaagctatt aatggataaa cccattcaca aaatcacacc aaatatctaa   6660
aatcatgttt aaaatctcct agaaatgggt t                                    6691
```

Human exmtDNA Nucleotide Substitutions and Deletions Relative to Corresponding Human mtDNA Sequence [SEQ ID NO:2]

| Mitochondrial Gene Region | Fragment | Human mtDNA Nucleotide Position No. | Human mtDNA SEQ ID NO:2 | Human exmtDNA Substitution (or Deletion) |
|---|---|---|---|---|
| COI | 5.8 kb pg | 6023 | G | A |
|  |  | 6221 | T | C |
|  |  | 6242 | C | T |
|  |  | 6266 | A | C |
|  |  | 6299 | A | G |
|  |  | 6366 | G | A |
|  |  | 6383 | G | A |
|  |  | 6410 | C | T |
|  |  | 6452 | C | T |
|  |  | 6483 | C | C |
|  |  | 6512 | T | C |
|  |  | 6542 | C | T |
|  |  | 6569 | C | A |
|  |  | 6641 | T | C |
|  |  | 6935 | C | T |
|  |  | 6938 | C | T |
|  |  | 7146 | A | G |
|  |  | 7232 | C | T |
|  |  | 7256 | C | T |
|  |  | 7316 | G | A |
| COI | 11 | 6023 | G | A |
| COI | 12 | 6221 | T | C |
|  |  | 6242 | C | T |
|  |  | 6266 | A | C |
|  |  | 6299 | A | G |
|  |  | 6366 | G | A |
|  |  | 6383 | G | A |
|  |  | 6410 | C | T |
| COI | 12 | 6160 | T | A |
|  |  | 6182 | G | A |
|  |  | 6185 | T | C |
|  |  | 5216 | T | C |
|  |  | 6221 | T | T |
|  |  | 6224 | C | T |
|  |  | 6236 | C | T |
|  |  | 6242 | C | T |
|  |  | 6251 | T | C |
|  |  | 6260 | G | A |
|  |  | 6266 | A | C |
|  |  | 6269 | A | C |
|  |  | 6281 | A | G |
|  |  | 6326 | C | T |
|  |  | 6335 | C | T |
|  |  | 6353 | A | G |
|  |  | 6356 | C | T |
|  |  | 6365 | T | C |
|  |  | 6366 | G | A |
|  |  | 6378 | T | C |

Fig. 4B

Human exmtDNA Nucleotide Substitutions and Deletions Relative to Corresponding Human mtDNA Sequence [SEQ ID NO:2]

| Mito-chondrial Gene Region | Fragment | Human mtDNA Nucleotide Position No. | Human mtDNA SEQ ID NO:2 | Human exmtDNA Substitution (or Deletion) |
|---|---|---|---|---|
| | | 6383 | G | A |
| | | 6389 | C | T |
| | | 6392 | T | C |
| | | 6398 | C | T |
| | | 6407 | T | C |
| | | 6410 | C | T |
| COI | 12 | 6260 | G | A |
| | | 6266 | A | C |
| | | 6269 | A | C |
| | | 6281 | A | G |
| | | 6326 | C | T |
| | | 6335 | C | T |
| | | 6353 | A | G |
| | | 6356 | C | T |
| | | 6365 | T | C |
| | | 6366 | G | A |
| | | 6378 | T | C |
| | | 6383 | G | A |
| | | 6392 | T | C |
| | | 6398 | C | T |
| COI | 12 | 6182 | G | A |
| | | 6216 | T | C |
| | | 6221 | T | C |
| | | 6260 | G | A |
| | | 6266 | A | C |
| | | 6269 | A | C |
| | | 6281 | A | G |
| | | 6326 | C | T |
| | | 6335 | C | T |
| | | 6353 | A | G |
| | | 6356 | C | T |
| | | 6365 | T | C |
| | | 6366 | G | A |
| | | 6378 | T | C |
| | | 6383 | G | A |
| | | 6392 | T | C |
| | | 6398 | C | T |
| COI | 12 | 6160 | T | A |
| | | 6182 | G | A |
| | | 6185 | T | C |
| | | 5216 | T | C |
| | | 6221 | T | C |
| | | 6224 | C | T |
| | | 6236 | C | T |
| | | 6242 | C | T |
| | | 6251 | T | C |
| | | 6266 | A | C |
| | | 6269 | A | C |

Fig. 4C

Human exmtDNA Nucleotide Substitutions and Deletions Relative to Corresponding Human mtDNA Sequence [SEQ ID NO:2]

| Mitochondrial Gene Region | Fragment | Human mtDNA Nucleotide Position No. | Human mtDNA SEQ ID NO:2 | Human exmtDNA Substitution (or Deletion) |
|---|---|---|---|---|
| | | 6326 | C | T |
| | | 6335 | C | T |
| | | 6353 | A | G |
| | | 6356 | C | T |
| | | 6365 | T | C |
| | | 6366 | G | A |
| | | 6378 | T | C |
| | | 6383 | G | A |
| | | 6392 | T | C |
| COI | 12 | 6160 | T | A |
| | | 6182 | G | A |
| | | 6185 | T | C |
| | | 5216 | T | C |
| | | 6221 | T | C |
| | | 6224 | C | T |
| | | 6242 | C | T |
| | | 6251 | T | C |
| | | 6260 | G | A |
| | | 6266 | A | C |
| | | 6269 | A | C |
| | | 6281 | A | G |
| | | 6326 | C | T |
| | | 6335 | C | T |
| | | 6353 | A | G |
| | | 6356 | C | T |
| | | 6365 | T | C |
| | | 6366 | G | A |
| | | 6378 | T | C |
| | | 6383 | G | A |
| | | 6389 | C | T |
| | | 6392 | T | C |
| | | 6398 | C | T |
| | | 6407 | T | C |
| | | 6410 | C | T |
| COI | 12 | 6251 | T | C |
| | | 6260 | G | A |
| | | 6266 | A | C |
| | | 6269 | A | C |
| | | 6281 | A | G |
| | | 6326 | C | T |
| | | 6335 | C | T |
| | | 6353 | A | G |
| | | 6356 | C | T |
| | | 6365 | T | C |
| | | 6366 | G | A |
| | | 6378 | T | C |
| | | 6383 | G | A |
| | | 6392 | T | C |

Fig. 4D

Human exmtDNA Nucleotide Substitutions and Deletions Relative to Corresponding Human mtDNA Sequence [SEQ ID NO:2]

| Mito-chondrial Gene Region | Fragment | Human mtDNA Nucleotide Position No. | Human mtDNA SEQ ID NO:2 | Human exmtDNA Substitution (or Deletion) |
|---|---|---|---|---|
| | | 6398 | C | T |
| COI | 12 | 6185 | T | C |
| | | 6251 | T | C |
| | | 6260 | G | A |
| | | 6266 | A | C |
| | | 6269 | A | C |
| | | 6281 | A | G |
| | | 6326 | C | T |
| | | 6335 | C | T |
| | | 6353 | A | G |
| | | 6356 | C | T |
| | | 6365 | T | C |
| | | 6366 | G | A |
| | | 6378 | T | C |
| | | 6383 | G | A |
| | | 6392 | T | C |
| | | 6398 | C | T |
| COI | 12 | 6185 | T | C |
| | | 6236 | C | T |
| | | 6251 | T | C |
| | | 6260 | G | A |
| | | 6266 | A | C |
| | | 6269 | A | C |
| | | 6281 | A | G |
| | | 6326 | C | T |
| | | 6335 | C | T |
| | | 6353 | A | G |
| | | 6356 | C | T |
| | | 6365 | T | C |
| | | 6366 | G | A |
| | | 6378 | T | C |
| | | 6383 | G | A |
| | | 6392 | T | C |
| | | 6398 | C | T |
| COI | 12 | 6236 | C | T |
| | | 6251 | T | C |
| | | 6260 | G | A |
| | | 6266 | A | C |
| | | 6269 | A | C |
| | | 6281 | A | G |
| | | 6326 | C | T |
| | | 6335 | C | T |
| | | 6353 | A | G |
| | | 6356 | C | T |
| | | 6365 | T | C |
| | | 6366 | G | A |
| | | 6378 | T | C |
| | | 6383 | G | A |

Fig. 4E

Human exmtDNA Nucleotide Substitutions and Deletions Relative to
Corresponding Human mtDNA Sequence [SEQ ID NO:2]

| Mito-chondrial Gene Region | Fragment | Human mtDNA Nucleotide Position No. | Human mtDNA SEQ ID NO:2 | Human exmtDNA Substitution (or Deletion) |
|---|---|---|---|---|
|  |  | 6392 | T | C |
|  |  | 6398 | C | T |
| COI | 12 | 6236 | C | T |
|  |  | 6251 | T | C |
|  |  | 6260 | G | A |
|  |  | 6266 | A | C |
|  |  | 6269 | A | C |
|  |  | 6281 | A | G |
|  |  | 6326 | C | T |
|  |  | 6335 | C | T |
|  |  | 6353 | A | G |
|  |  | 6356 | C | T |
|  |  | 6365 | T | C |
|  |  | 6366 | G | A |
|  |  | 6378 | T | C |
|  |  | 6383 | G | A |
|  |  | 6392 | T | C |
| COI | 12 | 6185 | T | C |
|  |  | 6236 | C | T |
|  |  | 6251 | T | C |
|  |  | 6260 | G | A |
|  |  | 6266 | A | C |
|  |  | 6269 | A | C |
|  |  | 6281 | A | G |
|  |  | 6326 | C | T |
|  |  | 6353 | A | G |
|  |  | 6356 | C | T |
|  |  | 6365 | T | C |
|  |  | 6366 | G | A |
|  |  | 6383 | G | A |
|  |  | 6392 | T | C |
|  |  | 6398 | C | T |
| COI | 12 | 6185 | T | C |
|  |  | 6236 | C | T |
|  |  | 6251 | T | C |
|  |  | 6260 | G | A |
|  |  | 6266 | A | C |
|  |  | 6269 | A | C |
|  |  | 6281 | A | G |
|  |  | 6326 | C | T |
|  |  | 6353 | A | G |
|  |  | 6356 | C | T |
|  |  | 6365 | T | C |
|  |  | 6366 | G | A |
|  |  | 6383 | G | A |
| COI | 12 | 6185 | T | C |
|  |  | 6251 | T | C |
|  |  | 6260 | G | A |

Fig. 4F

Human exmtDNA Nucleotide Substitutions and Deletions Relative to Corresponding Human mtDNA Sequence [SEQ ID NO:2]

| Mito-chondrial Gene Region | Fragment | Human mtDNA Nucleotide Position No. | Human mtDNA SEQ ID NO:2 | Human exmtDNA Substitution (or Deletion) |
|---|---|---|---|---|
| | | 6266 | A | C |
| | | 6269 | A | C |
| | | 6281 | A | G |
| | | 6326 | C | T |
| | | 6335 | C | T |
| | | 6353 | A | G |
| | | 6356 | C | T |
| | | 6365 | T | C |
| | | 6366 | G | A |
| | | 6383 | G | A |
| | | 6392 | T | C |
| | | 6398 | C | T |
| COI | 12 | 6185 | T | C |
| | | 6251 | T | C |
| | | 6260 | G | A |
| | | 6266 | A | C |
| | | 6269 | A | C |
| | | 6281 | A | G |
| | | 6326 | C | T |
| | | 6335 | C | T |
| | | 6353 | A | G |
| | | 6356 | C | T |
| | | 6365 | T | C |
| | | 6366 | G | A |
| | | 6392 | T | C |
| | | 6398 | C | T |
| COI | 13 | 6452 | C | T |
| | | 6483 | C | T |
| | | 6512 | T | C |
| | | 6542 | C | T |
| | | 6569 | C | A |
| | | 6641 | T | C |
| | | 6935 | C | T |
| | | 6938 | C | T |
| COI | 15 | 7146 | A | G |
| COI | 15 | 6950 | C | A |
| | | 6962 | G | A |
| | | 6965 | T | G |
| | | 6975 | T | C |
| | | 6990 | C | T |
| | | 7013 | G | A |
| | | 7040 | T | C |
| | | 7064 | T | C |
| | | 7076 | A | G |
| | | 7145 | C | T |
| | | 7146 | A | G |
| | | 7160 | C | A |
| | | 7175 | T | C |

Fig. 4G

Human exmtDNA Nucleotide Substitutions and Deletions Relative to Corresponding Human mtDNA Sequence [SEQ ID NO:2]

| Mito-chondrial Gene Region | Fragment | Human mtDNA Nucleotide Position No. | Human mtDNA SEQ ID NO:2 | Human exmtDNA Substitution (or Deletion) |
|---|---|---|---|---|
| COI | 15 | 6950 | C | A |
| | | 6962 | G | A |
| | | 6965 | T | G |
| | | 6975 | T | C |
| | | 7013 | G | A |
| | | 7040 | T | C |
| | | 7064 | T | C |
| | | 7076 | A | G |
| | | 7145 | C | T |
| | | 7146 | A | G |
| | | 7160 | C | A |
| | | 7175 | T | C |
| COI | 15 | 6932 | A | G |
| | | 6935 | C | T |
| | | 6938 | C | T |
| | | 6944 | T | C |
| | | 6950 | C | A |
| | | 6962 | G | A |
| | | 6965 | T | G |
| | | 6975 | T | C |
| | | 6990 | C | T |
| | | 7013 | G | A |
| | | 7022 | T | C |
| | | 7028 | C | T |
| | | 7037 | C | T |
| | | 7040 | T | C |
| | | 7064 | T | C |
| | | 7072 | T | C |
| | | 7079 | C | T |
| | | 7100 | A | G |
| | | 7112 | C | T |
| | | 7145 | C | T |
| | | 7146 | A | G |
| | | 7160 | C | A |
| | | 7169 | T | C |
| | | 7175 | T | C |
| COI | 15 | 6932 | A | G |
| | | 6935 | C | T |
| | | 6938 | C | T |
| | | 6944 | T | C |
| | | 6950 | C | A |
| | | 6962 | G | A |
| | | 6965 | T | G |
| | | 6975 | T | C |
| | | 6990 | C | T |
| | | 7013 | G | A |
| | | 7022 | T | C |
| | | 7028 | C | T |

Fig. 4H

Human exmtDNA Nucleotide Substitutions and Deletions Relative to Corresponding Human mtDNA Sequence [SEQ ID NO:2]

| Mitochondrial Gene Region | Fragment | Human mtDNA Nucleotide Position No. | Human mtDNA SEQ ID NO:2 | Human exmtDNA Substitution (or Deletion) |
|---|---|---|---|---|
| | | 7037 | C | T |
| | | 7064 | T | C |
| | | 7072 | T | C |
| | | 7079 | C | T |
| | | 7100 | A | G |
| | | 7112 | C | T |
| | | 7145 | C | T |
| | | 7146 | A | G |
| | | 7160 | C | A |
| | | 7169 | T | C |
| | | 7175 | T | C |
| COI | 15 | 6929 | A | G |
| | | 6938 | C | T |
| | | 6944 | T | C |
| | | 6950 | C | A |
| | | 6956 | T | C |
| | | 6962 | G | A |
| | | 7013 | G | A |
| | | 7022 | T | C |
| | | 7040 | T | C |
| | | 7064 | T | C |
| | | 7076 | A | G |
| | | 7133 | C | T |
| | | 7145 | C | T |
| | | 7146 | A | G |
| | | 7169 | T | C |
| COI | 15 | 6929 | A | G |
| | | 6938 | C | T |
| | | 6944 | T | C |
| | | 6950 | C | A |
| | | 6956 | T | C |
| | | 7013 | G | A |
| | | 7022 | T | C |
| | | 7040 | T | C |
| | | 7064 | T | C |
| | | 7076 | A | G |
| | | 7133 | C | T |
| | | 7145 | C | T |
| | | 7146 | A | G |
| | | 7169 | T | C |
| COI | 15 | 6929 | A | G |
| | | 6938 | C | T |
| | | 6944 | T | C |
| | | 6950 | C | A |
| | | 6956 | T | C |
| | | 6962 | G | A |
| | | 7013 | G | A |
| | | 7022 | T | C |

Fig. 4I

Human exmtDNA Nucleotide Substitutions and Deletions Relative to Corresponding Human mtDNA Sequence [SEQ ID NO:2]

| Mitochondrial Gene Region | Fragment | Human mtDNA Nucleotide Position No. | Human mtDNA SEQ ID NO:2 | Human exmtDNA Substitution (or Deletion) |
|---|---|---|---|---|
| | | 7040 | T | C |
| | | 7064 | T | C |
| | | 7076 | A | G |
| | | 7133 | C | T |
| | | 7146 | A | G |
| | | 7169 | T | C |
| COI | 15 | 6950 | C | A |
| | | 6962 | G | A |
| | | 6965 | T | G |
| | | 6975 | T | C |
| | | 6990 | C | T |
| | | 7013 | G | A |
| | | 7040 | T | C |
| | | 7064 | T | C |
| | | 7076 | A | G |
| | | 7145 | C | T |
| | | 7146 | A | G |
| | | 7160 | C | A |
| | | 7175 | T | C |
| COI | 15 | 6932 | A | G |
| | | 6938 | C | T |
| | | 6950 | C | A |
| | | 6962 | G | A |
| | | 6965 | T | G |
| | | 6975 | T | C |
| | | 6990 | C | T |
| | | 7013 | G | A |
| | | 7022 | T | C |
| | | 7028 | C | T |
| | | 7037 | C | T |
| | | 7040 | T | C |
| | | 7064 | T | C |
| | | 7072 | T | C |
| | | 7079 | C | T |
| | | 7100 | A | G |
| | | 7112 | C | T |
| | | 7146 | A | G |
| | | 7160 | C | A |
| | | 7169 | T | C |
| | | 7175 | T | C |
| COI | 16 | 7232 | C | T |
| | | 7256 | C | T |
| | | 7316 | G | A |
| COII | 5.8 kb pg | 7650 | C | T |
| | | 7705 | T | C |
| | | 7810 | C | T |
| | | 7868 | C | T |
| | | 7891 | C | T |

Fig. 4J

Human exmtDNA Nucleotide Substitutions and Deletions Relative to Corresponding Human mtDNA Sequence [SEQ ID NO:2]

| Mito-chondrial Gene Region | Fragment | Human mtDNA Nucleotide Position No. | Human mtDNA SEQ ID NO:2 | Human exmtDNA Substitution (or Deletion) |
|---|---|---|---|---|
| | | 7912 | G | A |
| | | 8021 | A | G |
| | | 8065 | G | A |
| | | 8140 | C | T |
| | | 8152 | G | A |
| | | 8167 | T | C |
| | | 8196-8197 | AC | deletion |
| | | 8203 | C | T |
| COII | 21/22/23 | 7650 | C | T |
| | | 7705 | T | C |
| | | 7810 | C | T |
| | | 7868 | C | T |
| | | 7891 | C | T |
| | | 7912 | G | A |
| | | 8021 | A | G |
| | | 8065 | G | A |
| | | 8140 | C | T |
| | | 8152 | G | A |
| | | 8167 | T | C |
| | | 8196-8197 | AC | deletion |
| | | 8203 | C | T |
| COII | 21/22/23 | 7650 | C | T |
| | | 7705 | T | C |
| | | 7810 | C | T |
| | | 7868 | C | T |
| | | 7891 | C | T |
| | | 7912 | G | A |
| | | 8021 | A | G |
| COII | 21 | 7650 | C | T |
| | | 7705 | T | C |
| | | 7810 | C | T |
| COII | 21 | 7650 | C | T |
| COII | 21/22/23 | 7650 | C | T |
| | | 7705 | T | C |
| | | 7861 | T | C |
| | | 7868 | C | T |
| | | 7891 | C | T |
| | | 7900 | C | T |
| | | 7912 | G | A |
| | | 7927 | C | T |
| | | 8011 | A | G |
| | | 8021 | A | G |
| | | 8038 | T | C |
| COII | 21/22/23 | 7650 | C | T |
| | | 7663 | C | T |
| | | 7705 | T | C |
| | | 7810 | C | T |
| | | 7868 | C | T |

Fig. 4K

Human exmtDNA Nucleotide Substitutions and Deletions Relative to
Corresponding Human mtDNA Sequence [SEQ ID NO:2]

| Mitochondrial Gene Region | Fragment | Human mtDNA Nucleotide Position No. | Human mtDNA SEQ ID NO:2 | Human exmtDNA Substitution (or Deletion) |
|---|---|---|---|---|
| | | 7891 | C | T |
| | | 7912 | G | A |
| | | 8021 | A | G |
| COII | 21/22/23 | 7650 | C | T |
| | | 7705 | T | C |
| | | 7810 | C | T |
| | | 7861 | T | C |
| | | 7868 | C | T |
| | | 7891 | C | T |
| | | 7900 | C | T |
| | | 7912 | G | A |
| | | 7927 | C | T |
| | | 8011 | A | G |
| | | 8021 | A | G |
| COII | 22 | 7868 | C | T |
| | | 7891 | C | T |
| | | 7912 | G | A |
| COII | 21/22/23 | 7650 | C | T |
| | | 7705 | T | C |
| | | 7757 | G | A |
| | | 7810 | C | T |
| | | 7868 | C | T |
| | | 7891 | C | T |
| | | 7912 | G | A |
| | | 8021 | A | G |
| COII | 22 | 7868 | C | T |
| | | 7891 | C | T |
| | | 8021 | A | G |
| COII | 21/22 | 7650 | C | T |
| | | 7810 | C | T |
| | | 7868 | C | T |
| | | 7891 | C | T |
| | | 7912 | G | A |
| | | 8021 | A | G |
| COII | 21/22 | 7650 | C | T |
| | | 7705 | T | C |
| | | 7810 | C | T |
| | | 7861 | T | C |
| | | 7868 | C | T |
| | | 7891 | C | T |
| | | 7900 | C | T |
| | | 7912 | G | A |
| | | 7927 | C | T |
| | | 8011 | A | G |
| | | 8021 | A | G |
| | | 8038 | T | C |
| COII | 21 | 7650 | C | T |
| | | 7810 | C | T |

Fig. 4L

Human exmtDNA Nucleotide Substitutions and Deletions Relative to Corresponding Human mtDNA Sequence [SEQ ID NO:2]

| Mito-chondrial Gene Region | Fragment | Human mtDNA Nucleotide Position No. | Human mtDNA SEQ ID NO:2 | Human exmtDNA Substitution (or Deletion) |
|---|---|---|---|---|
| COIII | 5.8 kb pg | 9254 | A | G |
| | | 9325 | T | C |
| | | 9329 | G | C |
| | | 9335 | C | T |
| | | 9434 | A | G |
| | | 9540 | T | C |
| | | 9545 | A | G |
| | | 9548 | G | A |
| | | 9559 | G | C |
| | | 9629 | A | G |
| ATPase 8 | 26/5.8 kb pg | 8392 | G | A |
| | | 8455 | C | T |
| | | 8461 | C | T |
| | | 8503 | T | C |
| | | 8545 | G | A |
| ATPase 8/6 | 519 bp pg | 8541 | G | A |
| | | 8557 | G | A |
| | | 8562 | C | T |
| | | 8566 | A | G |
| | | 8568 | C | A |
| ATPase 8 | 26 | 8371 | C | A |
| | | 8374 | A | G |
| | | 8380 | T | C |
| | | 8383 | T | C |
| | | 8386 | C | T |
| | | 8392 | G | A |
| | | 8401 | A | C |
| | | 8410 | C | A |
| | | 8419 | T | C |
| | | 8428 | C | T |
| | | 8455 | C | T |
| | | 8461 | C | T |
| | | 8467 | C | T |
| | | 8468 | C | T |
| | | 8469 | T | C |
| | | 8473 | T | deletion |
| | | 8476 | C | T |
| | | 8485 | G | A |
| | | 8491 | A | T |
| | | 8503 | T | C |
| | | 8506 | T | C |
| | | 8507 | A | G |
| | | 8509 | C | T |
| | | 8541 | G | A |
| | | 8558 | C | G |
| | | 8562 | C | T |
| | | 8566 | A | G |

Fig. 4M

Human exmtDNA Nucleotide Substitutions and Deletions Relative to Corresponding Human mtDNA Sequence [SEQ ID NO:2]

| Mitochondrial Gene Region | Fragment | Human mtDNA Nucleotide Position No. | Human mtDNA SEQ ID NO:2 | Human exmtDNA Substitution (or Deletion) |
|---|---|---|---|---|
| | | 8568 | C | A |
| ATPase 8 | 26/519 bp pg | 8371 | C | A |
| | | 8374 | A | G |
| | | 8383 | T | C |
| | | 8386 | C | T |
| | | 8392 | G | A |
| | | 8395 | C | T |
| | | 8396 | A | G |
| | | 8398 | C | T |
| | | 8401 | A | C |
| | | 8404 | T | C |
| | | 8410 | C | A |
| | | 8419 | T | C |
| | | 8422 | A | G |
| | | 8423 | C | T |
| | | 8428 | C | T |
| | | 8450 | T | C |
| | | 8459 | A | C |
| | | 8463 | A | G |
| | | 8467 | C | T |
| | | 8470 | A | G |
| | | 8473 | T | C |
| | | 8474 | C | A |
| | | 8485 | G | A |
| | | 8486 | C | T |
| | | 8487 | C | T |
| | | 8488 | C | T |
| | | 8491 | A | T |
| | | 8503 | T | C |
| | | 8506 | T | C |
| | | 8508 | A | G |
| | | 8509 | C | T |
| | | 8512 | A | G |
| | | 8539 | C | T |
| | | 8541 | G | A |
| | | 8557 | G | A |
| | | 8562 | C | T |
| | | 8566 | A | G |
| | | 8568 | C | A |
| ATPase 6 | 5.8 kb pg | 8545 | G | A |
| | | 8655 | C | T |
| | | 8677 | A | C |
| | | 8701 | A | G |
| | | 8718 | A | G |
| | | 8860 | A | G |
| | | 8943 | C | T |
| | | 9060 | C | A |
| | | 9075 | C | T |

Fig. 4N

Human exmtDNA Nucleotide Substitutions and Deletions Relative to
Corresponding Human mtDNA Sequence [SEQ ID NO:2]

| Mito-chondrial Gene Region | Fragment | Human mtDNA Nucleotide Position No. | Human mtDNA SEQ ID NO:2 | Human exmtDNA Substitution (or Deletion) |
|---|---|---|---|---|
| | | 9103 | C | T |
| | | 9168 | C | T |
| | | 9175 | C | T |
| ATPase 6 | 519 bp pg | 8584 | G | A |
| | | 8591 | T | C |
| | | 8592 | G | A |
| | | 8598 | T | C |
| | | 8610 | T | C |
| | | 8611 | C | T |
| | | 8614 | T | C |
| | | 8617 | A | G |
| | | 8622 | C | A |
| | | 8634 | T | C |
| | | 8661 | C | T |
| | | 8674 | A | C |
| | | 8676 | C | T |
| | | 8677 | A | C |
| | | 8682 | A | C |
| | | 8687 | C | T |
| | | 8697 | G | A |
| | | 8703 | C | G |
| | | 8709 | C | T |
| | | 8714 | C | T |
| | | 8718 | A | G |
| | | 8730 | A | G |
| | | 8733 | T | C |
| | | 8743 | G | A |
| | | 8745 | A | T |
| | | 8749 | T | C |
| | | 8751 | A | G |
| | | 8754 | C | T |
| | | 8775 | C | T |
| | | 8788 | C | T |
| | | 8793 | T | C |
| | | 8810 | C | T |
| ND1 | 63/5.8 kb pg | 4048 | G | A |
| | | 4104 | A | G |
| ND2 | 5.8 kb pg | 4496 | C | T |
| | | 4736 | T | C |
| | | 4769 | A | G |
| | | 4856 | T | C |
| | | 4904 | C | T |
| | | 4914 | C | T |
| | | 4940 | C | T |
| | | 4958 | A | G |
| | | 4985 | G | A |
| | | 4991 | G | A |
| | | 5041 | T | C |

Fig. 4O

Human exmtDNA Nucleotide Substitutions and Deletions Relative to Corresponding Human mtDNA Sequence [SEQ ID NO:2]

| Mitochondrial Gene Region | Fragment | Human mtDNA Nucleotide Position No. | Human mtDNA SEQ ID NO:2 | Human exmtDNA Substitution (or Deletion) |
|---|---|---|---|---|
| | | 5147 | G | A |
| | | 5320 | C | T |
| | | 5351 | A | G |
| | | 5387 | C | T |
| | | 5426 | T | C |
| | | 5471 | G | A |
| | | 5474 | A | G |
| | | 5498 | A | G |
| ND2 | 72 | 4736 | T | C |
| | | 4856 | T | C |
| | | 4904 | C | T |
| | | 4914 | C | T |
| | | 4940 | C | T |
| | | 4958 | A | G |
| | | 4991 | G | A |
| | | 5041 | T | C |
| ND2 | 73 | 5041 | T | C |
| | | 5147 | G | A |
| ND2 | 74 | 5320 | C | T |
| | | 5351 | A | G |
| | | 5387 | C | T |
| | | 5426 | T | C |
| | | 5471 | G | A |
| | | 5474 | A | G |
| | | 5498 | A | G |
| ND3 | 75 | 10040 | C | T |
| | | 10041 | A | G |
| | | 10043 | C | T |
| | | 10071 | T | C |
| | | 10077 | T | C |
| | | 10083 | A | G |
| | | 10088 | C | T |
| | | 10101 | T | C |
| | | 10107 | C | T |
| | | 10113 | A | G |
| | | 10124 | T | C |
| | | 10128 | C | T |
| | | 10143 | G | A |
| | | 10145 | C | T |
| | | 10162 | C | A |
| | | 10172 | G | A |
| | | 10175 | C | T |
| | | 10187 | T | C |
| | | 10188 | A | C |
| | | 10192 | C | T |
| | | 10197 | G | A |
| | | 10203 | G | A |
| | | 10205 | C | T |

Fig. 4P

Human exmtDNA Nucleotide Substitutions and Deletions Relative to Corresponding Human mtDNA Sequence [SEQ ID NO:2]

| Mitochondrial Gene Region | Fragment | Human mtDNA Nucleotide Position No. | Human mtDNA SEQ ID NO:2 | Human exmtDNA Substitution (or Deletion) |
|---|---|---|---|---|
| | | 10217 | A | G |
| | | 10235 | T | C |
| | | 10238 | T | C |
| | | 10244 | C | T |
| | | 10245 | T | C |
| | | 10256 | T | C |
| | | 10268 | C | T |
| | | 10274 | T | A |
| | | 10275 | T | C |
| | | 10277 | A | G |
| | | 10281 | C | T |
| | | 10304 | T | C |
| | | 10308 | C | T |
| | | 10309 | T | A |
| | | 10310 | G | A |
| | | 10318 | T | C |
| | | 10322 | T | C |
| | | 10325 | G | A |
| | | 10346 | C | T |
| | | 10353 | G | A |
| | | 10361 | T | C |
| | | 10364 | G | A |
| | | 10373 | G | A |
| | | 10377 | C | T |
| | | 10378 | T | C |
| | | 10385 | A | G |
| | | 10398 | A | G |
| | | 10410 | T | C |
| | | 10421 | C | T |
| ND3 | 75 | 10007 | T | G |
| | | 10008 | A | C |
| | | 10009 | G | T |
| | | 10037 | T | C |
| | | 10043 | C | A |
| | | 10044 | A | G |
| | | 10046 | T | C |
| | | 10047 | C | T |
| | | 10048 | A | G |
| | | 10061 | A | T |
| | | 10065 | T | C |
| | | 10067 | C | A |
| | | 10070 | C | A |
| | | 10071 | T | C |
| | | 10074 | A | G |
| | | 10075 | T | C |
| | | 10076 | T | C |
| | | 10077 | T | C |
| | | 10084 | T | C |

Fig. 4Q

Human exmtDNA Nucleotide Substitutions and Deletions Relative to Corresponding Human mtDNA Sequence [SEQ ID NO:2]

| Mitochondrial Gene Region | Fragment | Human mtDNA Nucleotide Position No. | Human mtDNA SEQ ID NO:2 | Human exmtDNA Substitution (or Deletion) |
|---|---|---|---|---|
| | | 10085 | C | T |
| | | 10086 | A | G |
| | | 10091 | C | T |
| | | 10092 | C | T |
| | | 10094 | C | A |
| | | 10095 | C | T |
| | | 10098 | G | A |
| | | 10100 | C | T |
| | | 10101 | T | C |
| | | 10104 | C | T |
| | | 10107 | C | T |
| | | 10110 | A | G |
| | | 10113 | A | G |
| | | 10115 | T | A |
| | | 10130 | A | T |
| | | 10131 | C | G |
| | | 10134 | C | T |
| | | 10139 | C | T |
| | | 10142 | C | T |
| | | 10143 | G | A |
| | | 10144 | G | C |
| | | 10145 | C | T |
| | | 10162 | C | G |
| | | 10165 | C | T |
| | | 10169 | C | T |
| | | 10172 | G | A |
| | | 10175 | C | T |
| | | 10176 | G | A |
| | | 10178 | C | A |
| | | 10181 | C | T |
| | | 10184 | C | T |
| | | 10187 | T | A |
| | | 10188 | A | T |
| | | 10191 | T | A |
| | | 10194 | C | T |
| | | 10196 | C | T |
| | | 10197 | G | A |
| | | 10201 | G | A |
| | | 10203 | G | C |
| | | 10207 | C | T |
| | | 10208 | T | C |
| | | 10226 | C | T |
| | | 10227 | T | C |
| | | 10235 | T | C |
| | | 10238 | T | C |
| | | 10241 | C | A |
| | | 10244 | C | T |
| | | 10245 | T | C |

Fig. 4R

Human exmtDNA Nucleotide Substitutions and Deletions Relative to Corresponding Human mtDNA Sequence [SEQ ID NO:2]

| Mito-chondrial Gene Region | Fragment | Human mtDNA Nucleotide Position No. | Human mtDNA SEQ ID NO:2 | Human exmtDNA Substitution (or Deletion) |
|---|---|---|---|---|
| | | 10247 | A | C |
| | | 10248 | T | C |
| | | 10253 | T | C |
| | | 10257 | C | deletion |
| | | 10265 | T | C |
| | | 10267 | C | T |
| | | 10271 | C | A |
| | | 10272 | C | T |
| | | 10274 | T | C |
| | | 10275 | T | C |
| | | 10283 | A | G |
| | | 10295 | A | T |
| | | 10303 | C | A |
| | | 10310 | G | T |
| | | 10311 | C | A |
| | | 10312 | C | T |
| | | 10320 | G | A |
| | | 10322 | T | C |
| | | 10324 | T | G |
| | | 10325 | G | T |
| | | 10326 | T | A |
| | | 10329 | T | A |
| | | 10334 | C | T |
| | | 10335 | T | C |
| | | 10338 | T | C |
| | | 10343 | C | T |
| | | 10345 | T | C |
| | | 10349 | C | T |
| | | 10353 | G | A |
| | | 10354 | C | T |
| | | 10359 | A | G |
| | | 10361 | T | G |
| | | 10364 | G | A |
| | | 10365 | G | A |
| | | 10366 | C | T |
| | | 10367 | C | T |
| | | 10373 | G | A |
| | | 10377 | C | A |
| | | 10378 | T | C |
| | | 10379 | A | C |
| | | 10394 | C | T |
| | | 10398 | A | G |
| | | 10399 | C | T |
| | | 10400 | C | T |
| | | 10404 | T | C |
| | | 10410 | T | A |
| | | 10421 | C | T |
| | | 10422 | A | T |

Fig. 4S

Human exmtDNA Nucleotide Substitutions and Deletions Relative to Corresponding Human mtDNA Sequence [SEQ ID NO:2]

| Mitochondrial Gene Region | Fragment | Human mtDNA Nucleotide Position No. | Human mtDNA SEQ ID NO:2 | Human exmtDNA Substitution (or Deletion) |
|---|---|---|---|---|
| | | 10426 | C | deletion |
| | | 10427 | G | deletion |
| | | 10428 | A | deletion |
| | | 10429 | A | deletion |
| ND3 | 75 | 10040 | C | T |
| | | 10041 | A | G |
| | | 10043 | C | T |
| | | 10071 | T | C |
| | | 10077 | T | C |
| | | 10083 | A | G |
| | | 10088 | C | T |
| | | 10101 | T | C |
| | | 10107 | C | T |
| | | 10113 | A | G |
| | | 10124 | T | C |
| | | 10128 | C | T |
| | | 10143 | G | A |
| | | 10145 | C | T |
| | | 10162 | C | A |
| | | 10172 | G | A |
| | | 10175 | C | T |
| | | 10187 | T | C |
| | | 10188 | A | C |
| | | 10192 | C | T |
| | | 10197 | G | A |
| | | 10203 | G | A |
| | | 10205 | C | T |
| | | 10217 | A | G |
| | | 10235 | T | C |
| | | 10238 | T | C |
| | | 10244 | C | T |
| | | 10245 | T | C |
| | | 10256 | T | C |
| | | 10268 | C | T |
| | | 10274 | T | A |
| | | 10275 | T | C |
| | | 10277 | A | G |
| | | 10281 | C | T |
| | | 10304 | T | C |
| | | 10308 | C | T |
| | | 10310 | G | A |
| | | 10318 | T | C |
| | | 10322 | T | C |
| | | 10325 | G | A |
| | | 10336 | T | A |
| | | 10346 | C | T |
| | | 10353 | G | A |
| | | 10361 | T | C |

Fig. 4T

Human exmtDNA Nucleotide Substitutions and Deletions Relative to Corresponding Human mtDNA Sequence [SEQ ID NO:2]

| Mitochondrial Gene Region | Fragment | Human mtDNA Nucleotide Position No. | Human mtDNA SEQ ID NO:2 | Human exmtDNA Substitution (or Deletion) |
|---|---|---|---|---|
| | | 10364 | G | A |
| | | 10370 | T | C |
| | | 10373 | G | A |
| | | 10377 | C | T |
| | | 10378 | T | C |
| | | 10385 | A | G |
| | | 10398 | A | G |
| | | 10410 | T | C |
| | | 10421 | C | T |
| ND3 | 75 | 10040 | C | T |
| | | 10041 | A | G |
| | | 10043 | C | T |
| | | 10071 | T | C |
| | | 10083 | A | G |
| | | 10088 | C | T |
| | | 10101 | T | C |
| | | 10107 | C | T |
| | | 10113 | A | G |
| | | 10124 | T | C |
| | | 10128 | C | T |
| | | 10143 | G | A |
| | | 10145 | C | T |
| | | 10162 | C | A |
| | | 10172 | G | A |
| | | 10175 | C | T |
| | | 10187 | T | C |
| | | 10188 | A | C |
| | | 10192 | C | T |
| | | 10197 | G | A |
| | | 10203 | G | A |
| | | 10205 | C | T |
| | | 10217 | A | G |
| | | 10235 | T | C |
| | | 10238 | T | C |
| | | 10244 | C | T |
| | | 10245 | T | C |
| | | 10256 | T | C |
| | | 10268 | C | T |
| | | 10274 | T | A |
| | | 10275 | T | C |
| | | 10277 | A | G |
| | | 10281 | C | T |
| | | 10304 | T | C |
| | | 10308 | C | T |
| | | 10310 | G | A |
| | | 10318 | T | C |
| | | 10322 | T | C |
| | | 10325 | G | A |

Fig. 4U

Human exmtDNA Nucleotide Substitutions and Deletions Relative to Corresponding Human mtDNA Sequence [SEQ ID NO:2]

| Mito-chondrial Gene Region | Fragment | Human mtDNA Nucleotide Position No. | Human mtDNA SEQ ID NO:2 | Human exmtDNA Substitution (or Deletion) |
|---|---|---|---|---|
| | | 10346 | C | T |
| | | 10353 | G | A |
| | | 10361 | T | C |
| | | 10364 | G | A |
| | | 10370 | T | C |
| | | 10373 | G | A |
| | | 10377 | C | T |
| | | 10378 | T | C |
| | | 10385 | A | G |
| | | 10398 | A | G |
| | | 10410 | T | C |
| | | 10421 | C | T |
| ND4L | 81 | 10475 | C | T |
| | | 10501 | C | A |
| | | 10547 | C | G |
| | | 10586 | G | A |
| | | 10589 | G | A |
| | | 10601 | T | C |
| | | 10646 | G | A |
| | | 10652 | T | C |
| | | 10670 | C | T |
| | | 10677 | G | A |
| | | 10679 | A | G |
| | | 10685 | G | A |
| | | 10688 | G | A |
| | | 10721 | A | G |
| | | 10750 | A | G |
| ND4 | 82 | 10750 | A | G |
| | | 10774 | C | T |
| | | 10785 | T | C |
| | | 10810 | T | C |
| | | 10846 | C | T |
| | | 10866 | T | C |
| | | 10873 | T | C |
| | | 10885 | T | C |
| | | 10915 | T | C |
| | | 10919 | C | T |
| | | 10920 | T | C |
| | | 10922 | A | T |
| | | 10927 | T | C |
| | | 10945 | A | G |
| | | 11016 | G | A |
| ND4 | 82 | 10750 | A | G |
| | | 10774 | C | T |
| | | 10810 | T | C |
| | | 10846 | C | T |
| | | 10866 | T | C |
| | | 10873 | T | C |

Fig. 4V

Human exmtDNA Nucleotide Substitutions and Deletions Relative to Corresponding Human mtDNA Sequence [SEQ ID NO:2]

| Mitochondrial Gene Region | Fragment | Human mtDNA Nucleotide Position No. | Human mtDNA SEQ ID NO:2 | Human exmtDNA Substitution (or Deletion) |
|---|---|---|---|---|
| | | 10885 | T | C |
| | | 10915 | T | C |
| | | 10919 | C | T |
| | | 10920 | T | C |
| | | 10922 | A | T |
| | | 10927 | T | C |
| | | 10945 | A | G |
| | | 11016 | G | A |
| ND4 | 82 | 10750 | A | G |
| | | 10774 | C | T |
| | | 10786 | T | C |
| | | 10800 | T | A |
| | | 10808 | C | T |
| | | 10810 | T | C |
| | | 10822 | C | T |
| | | 10846 | C | T |
| | | 10866 | T | C |
| | | 10873 | T | C |
| | | 10915 | T | C |
| | | 10920 | T | C |
| | | 10922 | A | T |
| | | 10927 | T | C |
| | | 10945 | A | G |
| | | 10975 | C | T |
| | | 11002 | A | G |
| | | 11009 | T | C |
| | | 11016 | G | A |
| | | 11017 | T | C |
| | | 11053 | A | G |
| ND4 | 82 | 10750 | A | G |
| | | 10775 | G | A |
| | | 10786 | T | C |
| | | 10801 | G | A |
| | | 10808 | C | T |
| | | 10810 | T | C |
| | | 10822 | C | T |
| | | 10846 | C | T |
| | | 10866 | T | C |
| | | 10873 | T | C |
| | | 10915 | T | C |
| | | 10920 | T | C |
| | | 10922 | A | T |
| | | 10927 | T | C |
| | | 10945 | A | G |
| | | 10975 | C | T |
| | | 11002 | A | G |
| | | 11009 | T | C |
| | | 11016 | G | A |

Fig. 4W

Human exmtDNA Nucleotide Substitutions and Deletions Relative to Corresponding Human mtDNA Sequence [SEQ ID NO:2]

| Mitochondrial Gene Region | Fragment | Human mtDNA Nucleotide Position No. | Human mtDNA SEQ ID NO:2 | Human exmtDNA Substitution (or Deletion) |
|---|---|---|---|---|
|  |  | 11017 | T | C |
|  |  | 11053 | A | G |
| ND4 | 83 | 11083 | A | G |
|  |  | 11097 | C | T |
|  |  | 11147 | T | C |
|  |  | 11176 | G | A |
|  |  | 11197 | C | T |
|  |  | 11233 | T | C |
|  |  | 11254 | T | C |
|  |  | 11260 | T | C |
|  |  | 11281 | A | G |
|  |  | 11284 | C | T |
|  |  | 11291 | C | T |
|  |  | 11302 | C | T |
|  |  | 11335 | T | C |
| ND4 | 85 | 11590 | A | G |
|  |  | 11662 | T | C |
|  |  | 11708 | A | G |
|  |  | 11719 | G | A |
|  |  | 11767 | C | T |
|  |  | 11770 | T | C |
|  |  | 11788 | C | T |
|  |  | 11809 | T | C |
|  |  | 11827 | T | C |
|  |  | 11852 | G | A |
|  |  | 11857 | C | T |
|  |  | 11887 | G | A |
| ND4 | 86 | 11857 | C | T |
|  |  | 11887 | G | A |
|  |  | 11914 | G | A |
|  |  | 11963 | G | A |
|  |  | 12007 | G | A |
|  |  | 12013 | A | G |
|  |  | 12018 | C | G |
|  |  | 12064 | C | T |
|  |  | 12088 | C | T |
|  |  | 12091 | T | C |
|  |  | 12115 | C | T |
|  |  | 12136 | T | C |
| ND4 | 86 | 11854 | T | C |
|  |  | 11863 | C | T |
|  |  | 11886 | A | G |
|  |  | 11875 | T | C |
|  |  | 11887 | G | A |
|  |  | 11898 | C | T |
|  |  | 11899 | T | C |
|  |  | 11902 | G | A |
|  |  | 11908 | A | G |

Fig. 4X

Human exmtDNA Nucleotide Substitutions and Deletions Relative to Corresponding Human mtDNA Sequence [SEQ ID NO:2]

| Mito-chondrial Gene Region | Fragment | Human mtDNA Nucleotide Position No. | Human mtDNA SEQ ID NO:2 | Human exmtDNA Substitution (or Deletion) |
|---|---|---|---|---|
| | | 11912 | A | T |
| | | 11914 | G | A |
| | | 11929 | T | C |
| | | 11935 | T | C |
| | | 11944 | T | C |
| | | 11953 | C | T |
| | | 11963 | G | A |
| | | 11986 | C | T |
| | | 12007 | G | A |
| | | 12013 | A | G |
| | | 12019 | C | A |
| | | 12047 | T | C |
| | | 12049 | C | T |
| | | 12064 | C | T |
| | | 12071 | G | A |
| | | 12091 | T | C |
| | | 12106 | C | T |
| | | 12112 | C | T |
| | | 12115 | C | T |
| | | 12131 | T | A |
| | | 12136 | T | C |
| ND5 | 93 | 12346 | C | T |
| | | 12348 | C | T |
| | | 12349 | A | G |
| | | 12351 | T | C |
| | | 12354 | T | C |
| | | 12362 | C | T |
| | | 12367 | A | G |
| | | 12372 | G | A |
| | | 12379 | C | T |
| | | 12394 | C | A |
| | | 12397 | A | G |
| | | 12403 | C | T |
| | | 12406 | G | A |
| | | 12408 | T | C |
| | | 12423 | A | G |
| | | 12425 | A | G |
| | | 12426 | C | T |
| | | 12438 | T | C |
| | | 12450 | C | A |
| | | 12454 | G | A |
| | | 12456 | C | T |
| | | 12463 | A | G |
| | | 12474 | C | T |
| | | 12477 | T | C |
| | | 12481 | T | C |
| | | 12501 | G | A |
| | | 12528 | G | A |

Fig. 4Y

Human exmtDNA Nucleotide Substitutions and Deletions Relative to Corresponding Human mtDNA Sequence [SEQ ID NO:2]

| Mitochondrial Gene Region | Fragment | Human mtDNA Nucleotide Position No. | Human mtDNA SEQ ID NO:2 | Human exmtDNA Substitution (or Deletion) |
|---|---|---|---|---|
| | | 12543 | C | A |
| | | 12557 | C | T |
| | | 12558 | C | A |
| | | 12561 | G | A |
| | | 12567 | C | G |
| | | 12574 | T | G |
| | | 12576 | C | T |
| | | 12603 | C | A |
| | | 12616 | T | C |
| | | 12618 | G | A |
| | | 12624 | T | C |
| | | 12630 | G | A |
| | | 12651 | G | A |
| | | 12654 | A | G |
| | | 12662 | A | G |
| ND5 | 93 | 12346 | C | T |
| | | 12349 | A | G |
| | | 12358 | A | C |
| | | 12367 | A | G |
| | | 12372 | G | A |
| | | 12379 | C | T |
| | | 12390 | C | T |
| | | 12406 | G | A |
| | | 12417 | C | T |
| | | 12432 | C | T |
| | | 12441 | T | A |
| | | 12454 | G | A |
| | | 12466 | T | C |
| | | 12469 | A | G |
| | | 12474 | C | T |
| | | 12501 | G | A |
| | | 12503 | G | A |
| | | 12519 | T | C |
| | | 12528 | G | A |
| | | 12540 | A | G |
| | | 12543 | C | A |
| | | 12561 | G | A |
| | | 12585 | C | T |
| | | 12588 | C | T |
| | | 12603 | C | T |
| | | 12616 | T | C |
| | | 12627 | A | G |
| | | 12630 | G | A |
| | | 12651 | G | A |
| | | 12662 | A | G |
| ND5 | 93 | 12302 | C | A |
| | | 12303 | C | A |
| | | 12311 | T | C |

Fig. 4Z

Human exmtDNA Nucleotide Substitutions and Deletions Relative to Corresponding Human mtDNA Sequence [SEQ ID NO:2]

| Mitochondrial Gene Region | Fragment | Human mtDNA Nucleotide Position No. | Human mtDNA SEQ ID NO:2 | Human exmtDNA Substitution (or Deletion) |
|---|---|---|---|---|
| | | 12312 | T | A |
| | | 12316 | G | A |
| | | 12319 | C | T |
| | | 12338 | T | C |
| | | 12341 | C | A |
| | | 12346 | C | T |
| | | 12348 | C | T |
| | | 12349 | A | deletion |
| | | 12352 | A | T |
| | | 12354 | T | C |
| | | 12357 | A | G |
| | | 12358 | A | G |
| | | 12360 | C | T |
| | | 12362 | C | T |
| | | 12363 | C | A |
| | | 12364 | C | A |
| | | 12365 | T | C |
| | | 12367 | A | G |
| | | 12372 | G | A |
| | | 12374 | C | T |
| | | 12375 | T | C |
| | | 12376 | T | C |
| | | 12379 | C | T |
| | | 12387 | C | T |
| | | 12388 | C | A |
| | | 12391 | A | G |
| | | 12392 | T | A |
| | | 12393 | C | T |
| | | 12394 | C | T |
| | | 12395 | T | A |
| | | 12396 | T | C |
| | | 12397 | A | T |
| | | 12398 | C | A |
| | | 12399 | C | T |
| | | 12400 | A | T |
| | | 12401 | C | A |
| | | 12405 | C | T |
| | | 12406 | G | A |
| | | 12409 | A | C |
| | | 12411 | C | A |
| | | 12413 | C | T |
| | | 12414 | T | C |
| | | 12415 | A | C |
| | | 12416 | A | T |
| | | 21417 | C | G |
| | | 12418 | A | C |
| | | 12423 | A | T |
| | | 12425 | A | G |

Fig. 4AA

Human exmtDNA Nucleotide Substitutions and Deletions Relative to Corresponding Human mtDNA Sequence [SEQ ID NO:2]

| Mito-chondrial Gene Region | Fragment | Human mtDNA Nucleotide Position No. | Human mtDNA SEQ ID NO:2 | Human exmtDNA Substitution (or Deletion) |
|---|---|---|---|---|
| | | 12426 | C | G |
| | | 12427 | T | C |
| | | 12428 | C | T |
| | | 12429 | A | C |
| | | 12430 | T | A |
| | | 12431 | A | T |
| | | 12432 | C | A |
| | | 12436 | C | A |
| | | 12438 | T | A |
| | | 12440 | A | T |
| | | 12441 | T | A |
| | | 12442 | G | T |
| | | 12443 | T | G |
| | | 12444 | A | T |
| | | 12448 | T | A |
| | | 12449 | C | A |
| | | 12453 | T | C |
| | | 12454 | G | T |
| | | 12455 | T | A |
| | | 12456 | C | T |
| | | 12457 | G | C |
| | | 12458 | C | G |
| | | 12459 | A | C |
| | | 12460 | T | A |
| | | 12461 | C | T |
| | | 12462 | C | A |
| | | 12463 | A | T |
| | | 12464 | C | G |
| | | 12466 | T | C |
| | | 12469 | A | C |
| | | 12470 | T | A |
| | | 12472 | A | C |
| | | 12473 | T | G |
| | | 12474 | C | T |
| | | 12475 | A | T |
| | | 12476 | G | A |
| | | 12477 | T | G |
| | | 12479 | T | C |
| | | 12480 | C | T |
| | | 12481 | T | C |
| | | 12482 | T | A |
| | | 12483 | C | T |
| | | 12486 | C | deletion |
| | | 12487 | A | deletion |
| | | 12494 | T | C |
| | | 12495 | A | G |
| | | 12498 | C | T |
| | | 12501 | G | A |

Fig. 4BB

Human exmtDNA Nucleotide Substitutions and Deletions Relative to Corresponding Human mtDNA Sequence [SEQ ID NO:2]

| Mitochondrial Gene Region | Fragment | Human mtDNA Nucleotide Position No. | Human mtDNA SEQ ID NO:2 | Human exmtDNA Substitution (or Deletion) |
|---|---|---|---|---|
| | | 12505 | C | A |
| | | 12506 | T | C |
| | | 12518 | T | C |
| | | 12519 | T | C |
| | | 12528 | G | A |
| | | 12537 | C | T |
| | | 12541 | G | A |
| | | 12542 | C | T |
| | | 12543 | C | G |
| | | 12545 | C | T |
| | | 12546 | A | G |
| | | 12548 | C | T |
| | | 12552 | A | G |
| | | 12555 | A | T |
| | | 12556 | A | C |
| | | 12557 | C | T |
| | | 12559 | C | A |
| | | 12561 | G | A |
| | | 12566 | C | T |
| | | 12567 | C | A |
| | | 12596 | T | C |
| | | 12599 | T | A |
| | | 12603 | C | T |
| | | 12609 | T | A |
| | | 12614 | C | T |
| | | 12615 | A | G |
| | | 12616 | T | C |
| | | 12618 | G | A |
| | | 12622 | G | A |
| | | 12627 | A | C |
| | | 12630 | G | A |
| | | 12633 | C | T |
| | | 12636 | C | T |
| | | 12637 | A | G |
| | | 12649 | C | A |
| | | 12651 | G | A |
| | | 12663 | C | T |
| ND5 | 93 | 12302 | C | A |
| | | 12303 | C | A |
| | | 12312 | T | A |
| | | 12315 | G | T |
| | | 12322 | C | T |
| | | 12346 | C | T |
| | | 12348 | C | T |
| | | 12349 | A | T |
| | | 12350 | C | T |
| | | 12352 | A | T |
| | | 12354 | T | C |

Fig. 4CC

Human exmtDNA Nucleotide Substitutions and Deletions Relative to Corresponding Human mtDNA Sequence [SEQ ID NO:2]

| Mitochondrial Gene Region | Fragment | Human mtDNA Nucleotide Position No. | Human mtDNA SEQ ID NO:2 | Human exmtDNA Substitution (or Deletion) |
|---|---|---|---|---|
| | | 12357 | A | T |
| | | 12360 | C | T |
| | | 12362 | C | T |
| | | 12363 | C | A |
| | | 12364 | C | A |
| | | 12370 | C | T |
| | | 12372 | G | A |
| | | 12374 | C | T |
| | | 12375 | T | C |
| | | 12379 | C | T |
| | | 12383 | T | C |
| | | 12384 | T | C |
| | | 12385 | C | T |
| | | 12386 | C | T |
| | | 12387 | C | A |
| | | 12390 | C | A |
| | | 12393 | C | T |
| | | 12394 | C | A |
| | | 12398 | C | T |
| | | 12399 | C | T |
| | | 12400 | A | G |
| | | 12403 | C | T |
| | | 12406 | G | A |
| | | 12407 | T | C |
| | | 12408 | T | C |
| | | 12415 | A | G |
| | | 12416 | A | G |
| | | 12417 | C | T |
| | | 12420 | A | G |
| | | 12423 | A | G |
| | | 12429 | A | G |
| | | 12432 | C | T |
| | | 12435 | C | A |
| | | 12436 | C | T |
| | | 12448 | T | A |
| | | 12449 | C | G |
| | | 12451 | A | deletion |
| | | 12452 | T | deletion |
| | | 12454 | G | A |
| | | 12457 | G | T |
| | | 12460 | T | A |
| | | 12461 | C | G |
| | | 12465 | C | T |
| | | 12468 | T | C |
| | | 12469 | A | G |
| | | 12470 | T | C |
| | | 12471 | T | C |
| | | 12474 | C | T |

Fig. 4DD

Human exmtDNA Nucleotide Substitutions and Deletions Relative to
Corresponding Human mtDNA Sequence [SEQ ID NO:2]

| Mito-chondrial Gene Region | Fragment | Human mtDNA Nucleotide Position No. | Human mtDNA SEQ ID NO:2 | Human exmtDNA Substitution (or Deletion) |
|---|---|---|---|---|
| | | 12477 | T | C |
| | | 12481 | T | C |
| | | 12483 | C | T |
| | | 12486 | C | G |
| | | 12487 | A | G |
| | | 12498 | C | T |
| | | 12504 | C | T |
| | | 12505 | C | A |
| | | 12506 | T | C |
| | | 12518 | T | C |
| | | 12519 | T | C |
| | | 12522 | T | C |
| | | 12528 | G | A |
| | | 12535 | C | T |
| | | 12537 | C | T |
| | | 12541 | G | A |
| | | 12542 | C | T |
| | | 12543 | C | A |
| | | 12548 | C | T |
| | | 12555 | A | C |
| | | 12556 | A | C |
| | | 12558 | C | A |
| | | 12559 | C | A |
| | | 12561 | G | A |
| | | 12567 | C | A |
| | | 12568 | C | T |
| | | 12592 | T | deletion |
| | | 12596 | T | deletion |
| | | 12600 | A | G |
| | | 12603 | C | T |
| | | 12606 | C | T |
| | | 12609 | T | A |
| | | 12616 | T | C |
| | | 12618 | G | A |
| | | 12621 | C | T |
| | | 12622 | G | A |
| | | 12624 | T | C |
| | | 12627 | A | T |
| | | 12630 | G | A |
| | | 12633 | C | T |
| | | 12636 | C | T |
| | | 12649 | C | deletion |
| | | 12651 | G | A |
| | | 12654 | A | G |
| | | 12663 | C | G |
| | | 12669 | C | T |
| ND6 | 91 | 14170 | A | T |
| | | 14172 | T | G |

Fig. 4EE

Human exmtDNA Nucleotide Substitutions and Deletions Relative to Corresponding Human mtDNA Sequence [SEQ ID NO:2]

| Mitochondrial Gene Region | Fragment | Human mtDNA Nucleotide Position No. | Human mtDNA SEQ ID NO:2 | Human exmtDNA Substitution (or Deletion) |
|---|---|---|---|---|
| | | 14182 | T | C |
| | | 14274 | A | G |
| | | 14284 | C | T |
| | | 14305 | G | A |
| | | 14311 | T | C |
| | | 14323 | G | A |
| | | 14362 | C | T |
| | | 14364 | G | A |
| | | 14368 | C | T |
| | | 14377 | C | T |
| | | 14384 | G | A |
| | | 14386 | T | C |
| | | 14404 | C | T |
| ND6 | 91 | 14152 | A | G |
| | | 14155 | C | A |
| | | 14165 | A | C |
| | | 14197 | T | G |
| | | 14215 | T | C |
| | | 14218 | T | C |
| | | 14255 | C | T |
| | | 14230 | A | G |
| | | 14237 | A | G |
| | | 14239 | C | T |
| | | 14275 | C | T |
| | | 14276 | C | G |
| | | 14280 | A | G |
| | | 14287 | T | C |
| | | 14305 | G | A |
| | | 14323 | G | A |
| | | 14326 | T | C |
| | | 14334 | C | T |
| | | 14350 | C | T |
| | | 14356 | C | T |
| | | 14362 | C | T |
| | | 14368 | C | T |
| | | 14371 | T | C |
| | | 14374 | T | C |
| | | 14377 | C | T |
| | | 14380 | C | T |
| | | 14384 | G | T |
| | | 14389 | C | T |
| | | 14404 | C | T |
| tRNA Lys | 519 bp pg | 8310 | T | C |
| | | 8311 | T | C |
| | | 8336 | T | C |
| | | 8345 | C | T |
| | | 8348 | A | T |
| | | 8349 | C | T |

Human exmtDNA Nucleotide Substitutions and Deletions Relative to
Corresponding Human mtDNA Sequence [SEQ ID NO:2]

| Mito-chondrial Gene Region | Fragment | Human mtDNA Nucleotide Position No. | Human mtDNA SEQ ID NO:2 | Human exmtDNA Substitution (or Deletion) |
|---|---|---|---|---|
|  |  | 8351 | C | T |
| tRNA Ile | 5.8 kb pg | 4312 | C | T |
|  |  | 4318 | C | T |
| tRNA Gln | 5.8 kb pg | 4375 | C | G |
|  |  | 4382 | C | A |
|  |  | 4398 | C | T |
| tRNA Met | 5.8 kb pg | 4456 | C | T |
| tRNA Cys | 5.8 kb pg | 5821 | G | A |
| tRNA Tyr | 5.8 kb pg | 5840 | C | T |
| tRNA Asp | 5.8 kb pg | 7521 | G | A |

*Fig. 4FF*

SEQUENCE LISTING

<160> NUMBER OF SEQ ID NOS: 108

<210> SEQ ID NO 1
<211> LENGTH: 519
<212> TYPE: DNA
<213> ORGANISM: Homo sapien

<400> SEQUENCE: 1

```
cactgtaaag ctaacccagc attaaccttt taagttaaag actaagagaa tcattatctc      60
tttacagtga aatgccacag ctaaatacca ctgtatgacc tgctatcatc accccaatac     120
tcctcacgtt atttctcatc acccaactaa aaatactaaa cacacactgc catctgccca     180
cctcaccaaa atttattaaa ataaaaaact acagtaagcc ctgagaacca aaatgaacga     240
```

-continued

| aaatttattc | gcttcattca | ttaccctac | agtactaggc | ctacccgcca | cagtaccaat | 300 |
| catcctattt | ccccccttac | tggtcccaac | ctccaaatac | ctcatcaaca | accgactaat | 360 |
| caccactcaa | caatgactac | ttcaactcac | cttaaaacaa | ataataacga | tacataaacat | 420 |
| taagggacga | acctggtccc | ttatactaat | ttccctgatt | atttttattg | ccacaactaa | 480 |
| tctcctcgga | ctcttgcccc | actcatttac | accaatcac | | | 519 |

<210> SEQ ID NO 2
<211> LENGTH: 16569
<212> TYPE: DNA
<213> ORGANISM: Homo sapien

<400> SEQUENCE: 2

| gatcacaggt | ctatcaccct | attaaccact | cacgggagct | ctccatgcat | ttggtatttt | 60 |
| cgtctggggg | gtatgcacgc | gatagcattg | cgagacgctg | gagccggagc | acccctatgtc | 120 |
| gcagtatctg | tctttgattc | ctgcctcatc | ctattattta | tcgcacctac | gttcaatatt | 180 |
| acaggcgaac | atacttacta | aagtgtgtta | ttaattaat | gcttgtagga | cataataata | 240 |
| acaattgaat | gtctgcacag | ccactttcca | cacagacatc | ataacaaaaa | atttccacca | 300 |
| aaccccccct | cccccgcttc | tggccacagc | acttaaacac | atctctgcca | aaccccaaaa | 360 |
| acaaagaacc | ctaacaccag | cctaaccaga | tttcaaattt | tatcttttgg | cggtatgcac | 420 |
| ttttaacagt | cacccccaa | ctaacacatt | attttcccct | cccactccca | tactactaat | 480 |
| ctcatcaata | caaccccgc | ccatcctacc | cagcacacac | acaccgctgc | taaccccata | 540 |
| ccccgaacca | accaaacccc | aaagacaccc | cccacagttt | atgtagctta | cctcctcaaa | 600 |
| gcaatacact | gaaaatgttt | agacgggctc | acatcacccc | ataaacaaat | aggtttggtc | 660 |
| ctagcctttc | tattagctct | tagtaagatt | acacatgcaa | gcatcccgt | tccagtgagt | 720 |
| tcaccctcta | aatcaccacg | atcaaaaggg | acaagcatca | agcacgcagc | aatgcagctc | 780 |
| aaaacgctta | gcctagccac | accccacgg | gaaacagcag | tgattaacct | ttagcaataa | 840 |
| acgaaagttt | aactaagcta | tactaacccc | agggttggtc | aatttcgtgc | cagccaccgc | 900 |
| ggtcacacga | ttaacccaag | tcaatagaag | ccggcgtaaa | gagtgtttta | gatcacccc | 960 |
| tccccaataa | agctaaaact | cacctgagtt | gtaaaaaact | ccagttgaca | caaaatagac | 1020 |
| tacgaaagtg | gctttaacat | atctgaacac | acaatagcta | agacccaaac | tgggattaga | 1080 |
| taccccacta | tgcttagccc | taaacctcaa | cagttaaatc | aacaaaactg | ctcgccagaa | 1140 |
| cactacgagc | cacagcttaa | aactcaaagg | acctggcggt | gcttcatatc | cctctagagg | 1200 |
| agcctgttct | gtaatcgata | aacccgatc | aacctcacca | cctcttgctc | agcctatata | 1260 |
| ccgccatctt | cagcaaaccc | tgatgaaggc | tacaaagtaa | gcgcaagtac | ccacgtaaag | 1320 |
| acgttaggtc | aaggtgtagc | ccatgaggtg | gcaagaaatg | ggctacattt | tctaccccag | 1380 |
| aaaactacga | tagcccttat | gaaacttaag | ggtcgaaggt | ggatttagca | gtaaactaag | 1440 |
| agtagagtgc | ttagttgaac | agggccctga | agcgcgtaca | caccgcccgt | caccctcctc | 1500 |
| aagtatactt | caaaggacat | ttaactaaaa | cccctacgca | tttatataga | ggagacaagt | 1560 |
| cgtaacatgg | taagtgtact | ggaaagtgca | cttggacgaa | ccagagtgta | gcttaacaca | 1620 |
| aagcacccaa | cttacactta | ggagatttca | acttaacttg | accgctctga | gctaaaccta | 1680 |
| gccccaaacc | cactccacct | tactaccaga | caaccttagc | caaaccattt | acccaaataa | 1740 |
| agtataggcg | atagaaattg | aaacctggcg | caatagatat | agtaccgcaa | gggaaagatg | 1800 |
| aaaaattata | accaagcata | atatagcaag | gactaaccc | tataccttct | gcataatgaa | 1860 |

```
ttaactagaa ataactttgc aaggagagcc aaagctaaga cccccgaaac cagacgagct   1920
acctaagaac agctaaaaga gcacacccgt ctatgtagca aaatagtggg aagatttata   1980
ggtagaggcg acaaacctac cgagcctggt gatagctggt tgtccaagat agaatcttag   2040
ttcaacttta aatttgccca cagaaccctc taaatcccct tgtaaattta actgttagtc   2100
caaagaggaa cagctctttg gacactagga aaaaaccttg tagagagagt aaaaaattta   2160
acacccatag taggcctaaa agcagccacc aattaagaaa gcgttcaagc tcaacaccca   2220
ctacctaaaa aatcccaaac atataactga actcctcaca cccaattgga ccaatctatc   2280
accctataga agaactaatg ttagtataag taacatgaaa acattctcct ccgcataagc   2340
ctgcgtcaga ttaaaacact gaactgacaa ttaacagccc aatatctaca atcaaccaac   2400
aagtcattat taccctcact gtcaacccaa cacaggcatg ctcataagga aaggttaaaa   2460
aaagtaaaag gaactcggca aatcttaccc cgcctgttta ccaaaaacat cacctctagc   2520
atcaccagta ttagaggcac cgcctgccca gtgacacatg tttaacggcc gcggtaccct   2580
aaccgtgcaa aggtagcata atcacttgtt ccttaaatag ggacctgtat gaatggctcc   2640
acgagggttc agctgtctct tactttttaac cagtgaaatt gacctgcccg tgaagaggcg   2700
ggcataaaca agcaagacga gaagacccta tggagcttta atttattaat gcaaacagta   2760
cctaacaaac ccacaggtcc taaactacca aacctgcatt aaaaatttcg gttggggcga   2820
cctcggagca gaacccaacc tccgagcagt acatgctaag acttcaccag tcaaagcgaa   2880
ctactatact caattgatcc aataacttga ccaacggaac aagttaccct agggataaca   2940
gcgcaatcct attctagagt ccatatcaac aatagggttt acgacctcga tgttggatca   3000
ggacatcccg atggtgcagc cgctattaaa ggttcgtttg ttcaacgatt aaagtcctac   3060
gtgatctgag ttcagaccgg agtaatccag gtcggtttct atctaccttc aaattcctcc   3120
ctgtacgaaa ggacaagaga aataaggcct acttcacaaa gcgccttccc ccgtaaatga   3180
tatcatctca acttagtatt atacccacac ccacccaaga acagggtttg ttaagatggc   3240
agagcccggt aatcgcataa aacttaaaac tttacagtca gaggttcaat tcctcttctt   3300
aacaacatac ccatggccaa cctcctactc ctcattgtac ccattctaat cgcaatggca   3360
ttcctaatgc ttaccgaacg aaaaattcta ggctatatac aactacgcaa aggccccaac   3420
gttgtaggcc cctacgggct actacaaccc ttcgctgacg ccataaaact cttcaccaaa   3480
gagcccctaa aacccgccac atctaccatc accctctaca tcaccgcccc gaccttagct   3540
ctcaccatcg ctcttctact atgaaccccc ctccccatac ccaaccccct ggtcaacctc   3600
aacctaggcc tcctatttat tctagccacc tctagcctag ccgtttactc aatcctctga   3660
tcagggtgag catcaaactc aaactacgcc ctgatcggcg cactgcgagc agtagcccaa   3720
acaatctcat atgaagtcac cctagccatc attctactat caacattact aataagtggc   3780
tcctttaacc tctccaccct tatcacaaca caagaacacc tctgattact cctgccatca   3840
tgacccttgg ccataatatg atttatctcc acactagcag agaccaaccg aaccccttc    3900 gaccttgccg aagggagtc cgaactagtc tcaggcttca acatcgaata cgccgcaggc   3960
cccttcgccc tattcttcat agccgaatac acaaacatta ttataataaa caccctcacc   4020
actacaatct tcctaggaac aacatatgac gcactctccc ctgaactcta cacaacatat   4080
tttgtcacca agaccctact tctaacctcc ctgttcttat gaattcgaac agcatacccc   4140
cgattccgct acgaccaact catacacctc ctatgaaaaa acttcctacc actcacccta   4200
```

-continued

```
gcattactta tatgatatgt ctccataccc attacaatct ccagcattcc ccctcaaacc  4260
taagaaatat gtctgataaa agagttactt tgatagagta aataatagga gcttaaaccc  4320
ccttatttct aggactatga gaatcgaacc catccctgag aatccaaaat tctccgtgcc  4380
acctatcaca ccccatccta aagtaaggtc agctaaataa gctatcgggc ccatacccccg  4440 aaaatgttgg ttatacccctt cccgtactaa ttaatcccct ggcccaaccc gtcatctact  4500
ctaccatctt tgcaggcaca ctcatcacag cgctaagctc gcactgattt tttacctgag  4560
taggcctaga aataaacatg ctagctttta ttccagttct aaccaaaaaa ataaaccctc  4620
gttccacaga agctgccatc aagtatttcc tcacgcaagc aaccgcatcc ataatccttc  4680
taatagctat cctcttcaac aatatactct ccggacaatg aaccataacc aatactacca  4740
atcaatactc atcattaata atcataatag ctatagcaat aaaactagga atagcccccct  4800 ttcacttctg agtcccagag gttacccaag gcacccctct gacatccggc ctgcttcttc  4860
tcacatgaca aaaactagcc cccatctcaa tcatatacca aatctctccc tcactaaacg  4920
taagccttct cctcactctc tcaatcttat ccatcatagc aggcagttga ggtggattaa  4980
accagaccca gctacgcaaa atcttagcat actcctcaat tacccacata ggatgaataa  5040
tagcagttct accgtacaac cctaacataa ccattcttaa tttaactatt tatattatcc  5100
taactactac cgcattccta ctactcaact aaaactccag caccacgacc ctactactat  5160
ctcgcacctg aaacaagcta acatgactaa caccccttaat tccatccacc ctcctctccc  5220
taggaggcct gcccccgcta accggctttt tgcccaaatg ggccattatc gaagaattca  5280
caaaaaacaa tagcctcatc atccccacca tcatagccac catcaccctc cttaacctct  5340
acttctacct acgcctaatc tactccacct caatcacact actccccata tctaacaacg  5400
taaaaataaa atgacagttt gaacatacaa acccacccc attcctcccc acactcatcg  5460
cccttaccac gctactccta cctatctccc cttttatact aataatctta tagaaattta  5520
ggttaaatac agaccaagag ccttcaaagc cctcagtaag ttgcaatact taatttctgt  5580
aacagctaag gactgcaaaa ccccactctg catcaactga acgcaaatca gccacttttaa  5640 ttaagctaag ccccttactag accaatggga cttaaaccca caaacactta gttaacagct  5700
aagcacccta atcaactggc ttcaatctac ttctcccgcc gccggaaaaa aaggcgggag  5760
aagccccggc aggtttgaag ctgcttcttc gaatttgcaa ttcaatatga aaatcacctc  5820
ggagctggta aaaagaggcc taaccccctgt ctttagattt acagtccaat gcttcactca  5880 gccatttttac ctcacccccca ctgatgttcg ccgaccgttg actattctct acaaaccaca  5940
aagacattgg aacactatac ctattattcg gcgcatgagc tggagtccta ggcacagctc  6000
taagcctcct tattcgagcc gagctgggcc agccaggcaa ccttctaggt aacgaccaca  6060
tctacaacgt tatcgtcaca gcccatgcat ttgtaataat cttcttcata gtaataccca  6120
tcataatcgg aggctttggc aactgactag ttccccctaat aatcggtgcc cccgatatgg  6180 cgttccccg cataaacaac ataagcttct gactcttacc tccctctctc ctactcctgc  6240
tcgcatctgc tatagtggag gccggagcag gaacaggttg aacagtctac cctcccttag  6300
cagggaacta ctcccaccct ggagcctccg tagacctaac catcttctcc ttacacctag  6360
caggtgtctc ctctatctta ggggccatca atttcatcac aacaattatc aatataaaac  6420
cccctgccat aacccaatac caaacgcccc tcttcgtctg atccgtccta atcacagcag  6480
tcctacttct cctatctctc ccagtcctag ctgctggcat cactatacta ctaacagacc  6540
gcaacctcaa caccaccttc ttcgaccccg ccggaggagg agaccccatt ctataccaac  6600
```

```
acctattctg attttttcggt caccctgaag tttatattct tatcctacca ggcttcggaa      6660
taatctccca tattgtaact tactactccg gaaaaaaaga accatttgga tacataggta      6720
tggtctgagc tatgatatca attggcttcc tagggtttat cgtgtgagca caccatatat      6780
ttacagtagg aatagacgta gacacacgag catatttcac ctccgctacc ataatcatcg      6840
ctatccccac cggcgtcaaa gtatttagct gactcgccac actccacgga agcaatatga      6900
aatgatctgc tgcagtgctc tgagccctag gattcatctt tcttttcacc gtaggtggcc      6960
tgactggcat tgtattagca aactcatcac tagacatcgt actacacgac acgtactacg      7020
ttgtagccca cttccactat gtcctatcaa taggagctgt atttgccatc ataggaggct      7080
tcattcactg atttccccta ttctcaggct acacccctaga ccaaacctac gccaaaatcc      7140
atttcactat catattcatc ggcgtaaatc taactttctt cccacaacac tttctcggcc      7200
tatccggaat gccccgacgt tactcggact accccgatgc ataccacca tgaaacatcc      7260 tatcatctgt aggctcattc atttctctaa cagcagtaat attaataatt ttcatgattt      7320
gagaagcctt cgcttcgaag cgaaaagtcc taatagtaga agaaccctcc ataaacctgg      7380
agtgactata tggatgcccc ccaccctacc acacattcga agaacccgta tacataaaat      7440
ctagacaaaa aaggaaggaa tcgaaccccc caaagctggt tcaagccaa ccccatggcc      7500 tccatgactt tttcaaaaag gtattagaaa accatttca taactttgtc aaagttaaat      7560
tataggctaa atcctatata tcttaatggc acatgcagcg caagtaggtc tacaagacgc      7620
tacttcccct atcatagaag agcttatcac ctttcatgat cacgccctca taatcatttt      7680
ccttatctgc ttcctagtcc tgtatgccct tttcctaaca ctcacaacaa aactaactaa      7740
tactaacatc tcagacgctc aggaaataga aaccgtctga actatcctgc ccgccatcat      7800
cctagtcctc atcgccctcc catccctacg catcctttac ataacagacg aggtcaacga      7860
tccctccctt accatcaaat caattggcca ccaatggtac tgaacctacg agtacaccga      7920
ctacggcgga ctaatcttca actcctacat acttccccca ttattcctag aaccaggcga      7980
cctgcgactc cttgacgttg acaatcgagt agtactcccg attgaagccc ccattcgtat      8040
aataattaca tcacaagacg tcttgcactc atgagctgtc cccacattag gcttaaaaac      8100
agatgcaatt cccggacgtc taaaccaaac cactttcacc gctacacgac cgggggtata      8160
ctacggtcaa tgctctgaaa tctgtggagc aaaccacagt ttcatgccca tcgtcctaga      8220
attaattccc ctaaaaatct tgaaataggg cccgtatttt accctatagc accccctcta      8280 cccctctag agcccactgt aaagctaact tagcattaac cttttaagtt aaagattaag      8340
agaaccaaca cctctttaca gtgaaatgcc ccaactaaat actaccgtat ggcccaccat      8400
aattaccccc atactcctta cactattcct catcacccaa ctaaaaatat aaacacaaa      8460 ctaccaccta cctccctcac caaagcccat aaaaataaaa aattataaca aaccctgaga      8520
accaaaatga cgaaaatct gttcgcttca ttcattgccc ccacaatcct aggcctaccc      8580
gccgcagtac tgatcattct atttcccct ctattgatcc ccacctccaa atatctcatc      8640
aacaaccgac taatcaccac ccaacaatga ctaatcaaac taacctcaaa acaaatgata      8700
accatacaca acactaaagg acgaacctga tctcttatac tagtatccctt aatcattttt      8760 attgccacaa ctaacctcct cggactcctg cctcactcat ttacaccaac cacccaacta      8820
tctataaacc tagccatggc catccccta tgagcgggca cagtgattat aggctttcgc      8880
tctaagatta aaaatgccct agcccacttc ttaccacaag gcacacctac acccccttatc      8940
```

-continued

```
cccatactag ttattatcga aaccatcagc ctactcattc aaccaatagc cctggccgta    9000
cgcctaaccg ctaacattac tgcaggccac ctactcatgc acctaattgg aagcgccacc    9060
ctagcaatat caaccattaa ccttccctct acacttatca tcttcacaat tctaattcta    9120
ctgactatcc tagaaatcgc tgtcgcctta atccaagcct acgttttcac acttctagta    9180
agcctctacc tgcacgacaa cacataatga cccaccaatc acatgcctat catatagtaa    9240
aacccagccc atgaccccta acagggccc tctcagccct cctaatgacc tccggcctag    9300
ccatgtgatt tcacttccac tccataacgc tcctcatact aggcctacta accaacacac    9360
taaccatata ccaatgatgg cgcgatgtaa cacgagaaag cacataccaa ggccaccaca    9420
caccacctgt ccaaaaaggc cttcgatacg ggataatcct atttattacc tcagaagttt    9480
ttttcttcgc aggatttttc tgagcctttt accactccag cctagcccct accccccaat    9540
taggagggca ctggccccca acaggcatca ccccgctaaa tccccctaga gtcccactcc    9600
taaacacatc cgtattactc gcatcaggag tatcaatcac ctgagctcac catagtctaa    9660
tagaaaacaa ccgaaaccaa ataattcaag cactgcttat tacaatttta ctgggtctct    9720
attttacccct cctacaagcc tcagagtact tcgagtctcc cttcaccatt tccgacggca    9780
tctacggctc aacattttt gtagccacag gcttccacgg acttcacgtc attattggct    9840
caactttcct cactatctgc ttcatccgcc aactaatatt tcactttaca tccaaacatc    9900
actttggctt cgaagccgcc gcctgatact ggcattttgt agatgtggtt tgactatttc    9960
tgtatgtctc catctattga tgagggtctt actcttttag tataaatagt accgttaact   10020
tccaattaac tagttttgac aacattcaaa aagagtaat aaacttcgcc ttaattttaa   10080
taatcaacac cctcctagcc ttactactaa taattattac attttgacta ccacaactca   10140
acggctacat agaaaaatcc accccttacg agtgcggctt cgaccctata tcccccgccc   10200
gcgtcccttt ctccataaaa ttcttcttag tagctattac cttcttatta tttgatctag   10260
aaattgccct ccttttaccc ctaccatgag ccctacaaac aactaacctg ccactaatag   10320
ttatgtcatc cctcttatta atcatcatcc tagccctaag tctggcctat gagtgactac   10380
aaaaaggatt agactgaacc gaattggtat atagtttaaa caaaacgaat gatttcgact   10440
cattaaatta tgataatcat atttaccaaa tgcccctcat ttacataaat attatactag   10500
catttaccat ctcacttcta ggaatactag tatatcgctc acacctcata tcctccctac   10560
tatgcctaga aggaataata ctatcgctgt tcattatagc tactctcata accctcaaca   10620
cccactccct cttagccaat attgtgccta ttgccatact agtctttgcc gcctgcgaag   10680
cagcggtggg cctagcccta ctagtctcaa tctccaacac atatggccta gactacgtac   10740
ataacctaaa cctactccaa tgctaaaact aatcgtccca caattatat tactaccact   10800
gacatgactt tccaaaaaac acataatttg aatcaacaca accacccaca gcctaattat   10860
tagcatcatc cctctactat tttttaacca aatcaacaac aacctattta gctgttcccc   10920
aacctttcc tccgaccccc taacaacccc ctcctaata ctaactacct gactcctacc   10980
cctcacaatc atggcaagcc aacgccactt atccagtgaa ccactatcac gaaaaaaact   11040
ctacctctct atactaatct ccctacaaat tccttaatt ataacattca cagccacaga   11100
actaatcata ttttatatct cttcgaaac cacacttatc cccaccttgg ctatcatcac   11160
ccgatgaggc aaccagccag aacgcctgaa cgcaggcaca tacttcctat tctacaccct   11220
agtaggctcc cttcccctac tcatcgcact aatttacact cacaacaccc taggctcact   11280
aaacattcta ctactcactc tcactgccca agaactatca aactcctgag ccataaactt   11340
```

```
aatatgacta gcttacacaa tagcttttat agtaaagata cctctttacg gactccactt   11400
atgactccct aaagcccatg tcgaagcccc catcgctggg tcaatagtac ttgccgcagt   11460
actcttaaaa ctaggcggct atggtataat acgcctcaca ctcattctca accccctgac   11520
aaaacacata gcctacccct tccttgtact atccctatga ggcataatta taacaagctc   11580
catctgccta cgacaaacag acctaaaatc gctcattgca tactcttcaa tcagccacat   11640
agccctcgta gtaacagcca ttctcatcca accccctga agcttaccg gcgcagtcat   11700 tctcataatc gcccacgggc ttacatcctc attactattc tgcctagcaa actcaaacta   11760
cgaacgcact cacagtcgca tcataatcct ctctcaagga cttcaaactc tactcccact   11820
aatagctttt tgatgacttc tagcaagcct cgctaacctc gccttacccc ccactattaa   11880
cctactggga gaactctctg tgctagtaac cacgttctcc tgatcaaata tcactctcct   11940
acttacagga ctcaacatac tagtcacagc cctatactcc ctctacatat ttaccacaac   12000 acaatgggc tcactcaccc accacattaa caacataaaa ccctcattca cacgagaaaa   12060
caccctcatg ttcatacacc tatcccccat tctcctccta cccctcaacc ccgacatcat   12120
taccgggttt tcctcttgta aatatagttt aaccaaaaca tcagattgtg aatctgacaa   12180
cagaggctta cgacccctta tttaccgaga agctcacaa gaactgctaa ctcatgcccc   12240
catgtctaac aacatggctt tctcaacttt taaaggataa cagctatcca ttggtcttag   12300
gccccaaaaa ttttggtgca actccaaata aaagtaataa ccatgcacac tactataacc   12360
accctaaccc tgacttccct aattcccccc atccttacca ccctcgttaa ccctaacaaa   12420
aaaaactcat accccatta tgtaaaatcc attgtcgcat ccacctttat tatcagtctc   12480
ttccccacaa caatattcat gtgcctagac caagaagtta ttatctcgaa ctgacactga   12540
gccacaaccc aaaacaaccca gctctcccta agcttcaaac tagactactt ctccataata   12600
ttcatccctg tagcattgtt cgttacatgg tccatcatag aattctcact gtgatatata   12660
aactcagacc caaacattaa tcagttcttc aaatatctac tcatcttcct aattaccata   12720
ctaatcttag ttaccgctaa caacctattc caactgttca tcggctgaga gggcgtagga   12780
attatatcct tcttgctcat cagttgatga tacgcccgag cagatgccaa cacagcagcc   12840
attcaagcaa tcctatacaa ccgtatcggc gatatcggtt tcatcctcgc cttagcatga   12900
tttatcctac actccaactc atgagaccca caacaaatag cccttctaaa cgctaatcca   12960
agcctcaccc cactactagg cctcctccta gcagcagcag gcaaatcagc ccaattaggt   13020 ctccaccccct gactccccte agccatagaa ggccccaccc cagtctcagc cctactccac   13080
tcaagcacta tagttgtagc aggaatcttc ttactcatcc gcttccaccc cctagcagaa   13140
aatagcccac taatccaaac tctaacacta tgcttaggcg ctatcaccac tctgttcgca   13200
gcagtctgcg cccttacaca aaatgacatc aaaaaaatcg tagccttctc cacttcaagt   13260
caactaggac tcataatagt tacaatcggc atcaaccaac cacacctagc attcctgcac   13320
atctgtaccc acgccttctt caaagccata ctatttatgt gctccgggtc catcatccac   13380
aaccttaaca atgaacaaga tattcgaaaa ataggaggac tactcaaaac catacctctc   13440
acttcaacct ccctcaccat tggcagccta gcattagcag gaatacctt cctcacaggt   13500 ttctactcca aagaccacat catcgaaacc gcaaacatat catacacaaa cgcctgagcc   13560
ctatctatta ctctcatcgc tacctcctg acaagcgcct atagcactcg aataattctt   13620
ctcaccctaa caggtcaacc tcgcttcccc acccttacta acattaacga aataaccccc   13680
```

```
accctactaa accccattaa acgcctggca gccggaagcc tattcgcagg atttctcatt    13740
actaacaaca tttcccccgc atccccttc  caaacaacaa tcccctcta cctaaaactc    13800
acagccctcg ctgtcacttt cctaggactt ctaacagccc tagacctcaa ctacctaacc    13860
aacaaactta aaataaaatc cccactatgc acattttatt tctccaacat actcggattc    13920
tacccctagca tcacacaccg cacaatcccc tatctaggcc ttcttacgag ccaaaacctg    13980
cccctactcc tcctagacct aacctgacta gaaaagctat tacctaaaac aatttcacag    14040
caccaaatct ccacctccat catcacctca acccaaaaag gcataattaa actttacttc    14100
ctctctttct tcttcccact catcctaacc ctactcctaa tcacataacc tattcccccg    14160
agcaatctca attacaatat atacaccaac aaacaatgtt caaccagtaa ctactactaa    14220
tcaacgccca taatcataca agcccccgc accaatagga tcctcccgaa tcaaccctga    14280
cccctctcct tcataaatta ttcagcttcc tacactatta aagtttacca caaccaccac    14340
cccatcatac tctttcaccc acagcaccaa tcctacctcc atcgctaacc ccactaaaac    14400
actcaccaag acctcaaccc ctgaccccca tgcctcagga tactcctcaa tagccatcgc    14460
tgtagtatat ccaaagacaa ccatcattcc ccctaaataa attaaaaaaa ctattaaacc    14520
catataacct cccccaaaat tcagaataat aacacacccg accacaccgc taacaatcaa    14580
tactaaaccc ccataaatag gagaaggctt agaagaaaac cccacaaacc ccattactaa    14640
acccacactc aacagaaaca agcatacat cattattctc gcacggacta caaccacgac    14700
caatgatatg aaaaaccatc gttgtatttc aactacaaga acaccaatga ccccaatacg    14760
caaaattaac ccctaataa aattaattaa ccactcattc atcgacctcc cccacccatc    14820
caacatctcc gcatgatgaa acttcggctc actccttggc gctgcctga tcctccaaat    14880
caccacagga ctattcctag ccatgcacta ctcaccagac gcctcaaccg ccttttcatc    14940
aatcgcccac atcactcgag acgtaaatta tggctgaatc atccgctacc ttcacgccaa    15000
tggcgcctca atattcttta tctgcctctt cctacacatc gggcgaggcc tatattacgg    15060
atcatttctc tactcagaaa cctgaaacat cggcattatc ctcctgcttg caactatagc    15120
aacagccttc ataggctatg tcctcccgtg aggccaaata tcattctgag gggccacagt    15180
aattacaaac ttactatccg ccatcccata cattgggaca gacctagttc aatgaatctg    15240
aggaggctac tcagtagaca gtcccacccct cacacgattc tttaccttc  acttcatctt    15300
gcccttcatt attgcagccc tagcaacact ccacctccta ttcttgcacg aaacgggatc    15360
aaacaacccc ctaggaatca cctcccattc cgataaaatc accttccacc cttactacac    15420
aatcaaagac gccctcggct tacttctctt ccttctctcc ttaatgacat taacactatt    15480
ctcaccagac ctcctaggcg acccagacaa ttataccta gccaaccct taaacacccc    15540
tccccacatc aagcccgaat gatatttcct attcgcctac acaattctcc gatccgtccc    15600
taacaaacta ggaggcgtcc ttgccctatt actatccatc ctcatcctag caataatccc    15660
catcctccat atatccaaac aacaaagcat aatatttcgc ccactaagcc aatcactttta   15720
ttgactccta gccgcagacc tcctcattct aacctgaatc ggaggacaac cagtaagcta    15780
cccttttacc atcattggac aagtagcatc cgtactatac ttcacaacaa tcctaatcct    15840
aataccaact atctccctaa ttgaaaacaa atactcaaa tgggcctgtc cttgtagtat    15900
aaactaatac accagtcttg taaaccggag atgaaaacct ttttccaagg acaaatcaga    15960
gaaaagtct ttaactccac cattagcacc caaagctaag attctaatttt aaactattct    16020
ctgttctttc atggggaagc agatttgggt accacccaag tattgactca cccatcaaca    16080
```

-continued

```
accgctatgt atttcgtaca ttactgccag ccaccatgaa tattgtacgg taccataaat    16140
acttgaccac ctgtagtaca taaaaaccca atccacatca aaaccccctc cccatgctta    16200
caagcaagta cagcaatcaa ccctcaacta tcacacatca actgcaactc caaagccacc    16260
cctcacccac taggatacca acaaacctac ccacccttaa cagtacatag tacataaagc    16320
catttaccgt acatagcaca ttacagtcaa atcccttctc gtcccatgg atgacccccc     16380 tcagataggg gtcccttgac caccatcctc cgtgaaatca atatcccgca caagagtgct    16440
actctcctcg ctccgggccc ataacacttg ggggtagcta aagtgaactg tatccgacat    16500
ctggttccta cttcagggtc ataaagccta aatagcccac acgttcccct taaataagac    16560
atcacgatg                                                           16569
```

<210> SEQ ID NO 3
<211> LENGTH: 6691
<212> TYPE: DNA
<213> ORGANISM: Homo sapien
<220> FEATURE:
<221> NAME/KEY: misc_feature
<222> LOCATION: (1)...(6691)
<223> OTHER INFORMATION: n = A,T,C or G

<400> SEQUENCE: 3

```
ataggcattc caactcatcc gcttgctgac gacctccacg tgatttcaac aatgatttca      60
aatatttcac tttttaagtc agtgtgactt aagtatgaaa ttgcctctcc ctaaagctcc     120
cctaaggcct aaacagtcgt cattaccata gctgtgacag ggagactgtt gaatttataa     180
tctattggcc attcacagca tagcgtataa accctagctc atgatttctt tgcaatagaa     240
gtgtactttt tcatcacatt cccttcacaa cttactcacc agacagactt tgagctctcc     300
tcctggctta gcctggatcg tttgaaatgg tcatccatcc tttggcccca ataacctaaac    360 taaggtctat gaacaataag atgattttac ttcagtggga cttttttgtt taatatatta     420
gatttgacct tcagcaaggt caagggagt ccgaactagt ctcaggcttc aacatcgaat      480
acgccgcagg nccctttcgcc ctattcttca tagccgaata cacaaacatt attataataa    540
acaccctcac cactacaatc ttcctaggaa caacatataa cgcactctcc cctgaactct     600
acacaacata ttttgtcacc aagaccctac ttctgacctc cctgttctta tgaattcgaa     660
cagcataccc ccgattccgc tacgaccaac tcatacacct cctatgaaaa aacttcctac     720
cactcaccct agcattactt atatgatatg tctccatacc cattacaatc tccagcattc     780
cccctcaaac ctaagaaata tgtctgataa aagagttact ttgatagagt aaataatagg     840
agtttaaatc cccttatttc taggactatg agaatcgaac ccatccctga aatccaaaa     900 ttctcggtgc caactatcac acccccatctt aaagtaaggt cagctaaata agctatcggg    960 cccataccce gaaaatgttg gttatatcct tcccgtacta attaatcccc tggcccaacc    1020
cgtcatttac tctaccatct ttgcaggcac actcatcaca gcgctaagct cgcactgatt    1080
ttttacctga gtaggcctag aaataaacat gctagctttt attccagttc taaccaaaaa   1140
aataaaccct cgttccacag aagntgccat caagtatttc ctcacgcaag caaccgcatc    1200
cataatcctt ctaatagcta tcctntttcaa caatatactc tccggacaat gaaccatwac   1260
caataccacc aatcaatact catcattaat aatcataatg gctatagcaa taaaactagg   1320
aatagccccc tttcacttct gagtcccaga ggttacccaa gcacccctc tgacatccgg   1380 cctgctcctt ctcacatgac aaaaactagc ccccatctca atcatatacc aaatttctcc   1440
```

-continued

```
ctcattaaac gtaagccttc tcctcactct ttcaatctta tccatcatgg caggcagttg   1500
aggtggatta aaccaaaccc aactacgcaa atcttagca tactcctcaa ttacccacat   1560
aggatgaata acagcagttc taccgtacaa ccctaacata accattctta atttaactat   1620
ttatattatc ctaactacta ccgcattcct actactcaac ttaaactcca gcaccacaac   1680
cctactacta tctcgcacct gaaacaagct aacatgacta cacccttaa ttccatccac   1740 cctcctctcc ctaggaggcc tgccccgct aaccggcttt ttgcccaaat gggccattat   1800
cgaagaattc acaaaaaaca atagcctcat catccccacc atcatagcca tcatcaccct   1860 ccttaaccte tacttctacc tgcgcctaat ctactccacc tcaatcacac tactccctat   1920
atctaacaac gtaaaaataa aatgacagtt tgaacacaca aaacccaccc cattcctccc   1980
cacactcatc gcccttacca cactgctcct acctatctcc ccttttatgc taataatctt   2040
atagaaattt aggttaaata cagaccaaga gccttcaaag ccctcagtaa gttgcaatac   2100
ttaatttctg naacagctaa ggactgcaaa accccactct gcatcaactg nangcaaatc   2160
agccacttta attaagctaa gcccttacta gaccaatggg acttaaaccc acaaacactt   2220
agttaacagc taagcaccct aatcaactgg cttcaatcta cttctcccgc cgccgggaaa   2280
aaaggcggga gaagccccgg caggtttgaa gctgcttctt cgaatttgca attcaatatg   2340
aaaatcacct canagctggt aaaaagaggc ttaacccctg tctttagatt tacagtccaa   2400
tgcttcactc agccatttta cctcacccc actgatgttc gccgaccgtt gactattctc   2460
tacaaaccac aaagacattg gaacactata cctattattc ggcgcatgag ctggagtcct   2520
aggcacagct ctaagcctcc ttattcgagc cgaactgggc cagccaggca accttctagg   2580
taacgaccac atctacaacg ttatcgtcac agcccatgca tttgtaataa tcttcttcat   2640
agtaataccc atcataatcg gaggytttgg caastgacta gttcccctaa taatcggtgc   2700
ccccgatatg gsgtttcccc gcataaacaa cataagcttn tgactcttac ccccctctct   2760
cntactcctg ttngcatctg ctatagtgga ggccggcgca ggaacaggtt gaacagtnta   2820
ccctcccttg gcagggaact actcccaccc tggagcctcc gtagacctaa ccatcttctc   2880
cttacaccta gcaggtatct cctctatctt agggaccatc aatttcatca acaacaattat   2940 taatataaaa cccctgcca taacccaata ccaaacgccc cttttcgtct gatccgtcct   3000
aatcacagca gtcttacttc tcctatctct cccagtccta gccgctggca tcactatact   3060
actaacagac cgtaacctca acaccacctt cttcgaccca gccggaggag gagaccccat   3120
tctataccaa cacctattct gatttttcgg tcaccctgaa gtttatattc tcatcctacc   3180
aggcttcgga ataatctccc atattgtaac ttactactcc ggaaaaaag aaccatttgg   3240 atacataggt atggtctgag ctatgatatc aattggcttc ctagggttta tcgtgtgagc   3300
acaccatata tttacagtag gaatagacgt agacacacga gcatatttca cctccgctac   3360
cataatcatc gctatcccca ccggcgtcaa agtatttagc tgactcgcca cactccacgg   3420
aagcaatatg aaatgatctg ctgcagtgct ctgagcccta ggatttattt ttcttttcac   3480
cgtaggtggc ctgactggca ttgtattagc aaactcatca ctagacatcg tactacacga   3540
cacgtactac gttgtagccc acttccacta tgtcctatca ataggagctg tatttgccat   3600
cataggaggc ttcattcact gatttcccct attctcaggc tacacctag accaaaccta   3660 cgccaaaatc catttcgcta tcatattcat cggcgtaaat ctaactttct tcccacaaca   3720
ctttctcggc ctatccggaa tgccccgacg ttactcggac tatcccgatg catacaccac   3780
atgaaatatc ctatcatctg taggctcatt catttctcta acagcagtaa tattaataat   3840
```

```
tttcataatt tgagaagcct tcgcttcgaa gcgaaaagtc ctaatagtag aagaaccctc    3900
cataaacctg gagtgactat atggatgccc cccaccctac cacacattcg aagaacccgt    3960
atacataaaa tctagacaaa aaaggaagga atcgaacccc ccaaagctgg tttcaagcca    4020
accccatggc ctccatgact ttttcaaaaa gatattagaa aaaccatttc ataactttgt    4080
caaagttaaa ttataggcta aatcctatat atcttaatgg cacatgcagc gcaagtaggt    4140
ctacaagacg ctacttcccc tatcatagaa gagcttatca tctttcatga tcacgccctc    4200
ataatcattt tccttatctg cttcctagtc ctgtacgccc ttttcctaac actcacaaca    4260
aaactaacta atactaacat ctcagacgct caggaaatag aaaccgtctg aactatcctg    4320
cccgccatca tcctagtcct tatcgccctc ccatncctac gcatccttta cataacagac    4380
gaggtcaacg atccctcctt taccatcaaa tcaattggcc atcaatggta ctgaacctac    4440
gaatacaccg actacggcgg actaatcttc aactcctaca tacttccccc attattccta    4500
gaaccaggcg acctgcgact ccttgacgtt gacaatcgag tagtactccc ggttgaagcc    4560
cccattcgta taataattac atcacaagac gtcttacact catgagctgt ccccacatta    4620
ggcttaaaaa cagatgcaat tcccggacgt ctaaaccaaa ccactttcac tgctacacga    4680
ccagggggtat actacggcca atgctctgaa atctgtggag caaaccagtt ttatgcccat    4740
cgtcctagaa ttaattcccc taaaaatctt tgaaataggg cccgtattta ccctatagca    4800
cccctctac ccctctaga gcccactgta aagctaactt agcattaacc ttttaagtta    4860
aagattaaga gaaccaacac ctctttacag tgaaatgccc caactaaata ctaccgtatg    4920
acccaccata attcccccca tactccttac actattcctc atcacccaac taaaaatatt    4980
aaatacaaat taccacctac ctccctcacc aaagcccata aaataaaaa actataacaa    5040
accctgagaa ccaaaatgaa cgaaaatctg ttcacttcat tcattgcccc cacaatccta    5100
ggcctacccg ccgcagtact gatcattcta ttyccccctc tattgatccc cacctccaaa    5160
tatctcatca acaaccgact aattaccacc caacaatgac taatccaact aacctcaaaa    5220
caaatgatag ccatacacaa cactaaggga cgaacctgat ctcttatact agtatcctta    5280
atcattttta ttgccacaac taacctcctc ggactcctgc ctcactcatt tacaccaacc    5340
acccaactat ctataaacct agccatggcc atccccttat gagcgggcgc agtgattata    5400
ggctttcgct ctaagattaa aaatgcccta gcccacttct taccacaagg cacacctaca    5460
cccccttatcc ctatactagt tattatcgaa accatcagcc tactcattca accaatagcc    5520
ctggccgtan gnctaaccgc taacattact gcaggccacc tactcatgna cctaattgga    5580
agcgccacac tagcaatatc aantattaac cttccctcta cacttatcat tttcacaatt    5640
ctaattctac tgactatcct agaaatcgct gtcgccttaa tccaagccta cgttttaca    5700
cttttagtaa gcctctacct gcacgacaac acataatgac ccaccaatca catgcctatc    5760
atatagtaaa acccagccca tggcccctaa caggggccct ctcancccctc ctaatgacct    5820
ccggcctagc catgtgattt cacttccact ccacaaccct cctatacta ggcctactaa    5880
ccaacacact aaccatatac caatgatggc gcgatgtaac acgagaaagc acataccaag    5940
gccaccacac accacctgtc cagaaaggcc ttcgatacgg gataatccta tttattcctt    6000
cagaagtttt tttcttcgca ggatttttct gagccttta ccactccagc ctagccccna    6060
ccccccaact aggggggacac tggccccaa caggcatcac cccgctaaat ccctagaag    6120
tcccactcct aaaacacatcc gtattactcg catcagggggt atcaatcacc tgagctcacc    6180
```

-continued

| | |
|---|---|
| atagtctaat agaaacaac cgaaaccaaa taattcaagc actgcttatt acaattttac | 6240 |
| tgggtctcta ttttacccctc ctacaagcct cagngtactt cgaggttaaa atattagata | 6300 |
| tttccccctga tacagggctc aatcttttc tttttaaagc aatatttctc aaagtactttt | 6360 |
| tcacagaact taagtttcat taagcacttc actaaaagna aaagtctgtg atctaataaa | 6420 |
| tttggaaaat attgagaatt agagccccct cttagatatg tactgtagct actcagcttg | 6480 |
| ttacagatgg aagtaaacat tgtaatattc acccagcttt tgagtggatg tctattaaca | 6540 |
| tcacccaaat gagtattcca tggaatgcac tttgcaaaaa cctattattc aagaaaatt | 6600 |
| ctggagcatg gaaagctatt aatggataaa cccattcaca aaatcacacc aaatatctaa | 6660 |
| aatcatgttt aaaatctcct agaaatgggt t | 6691 |

<210> SEQ ID NO 4
<211> LENGTH: 1263
<212> TYPE: DNA
<213> ORGANISM: Homo sapien

<400> SEQUENCE: 4

| | |
|---|---|
| gagagaggc atgtgaattg ggaatttggg aaaaatttt tggggggaag gaaagaaata | 60 |
| gaggtcaaga ggtagaatag aagttgatga agaaaagaaa aaaagaaggt aatgaagggg | 120 |
| gtgctggatg tttccaacac aaagaaatga taaatgtttg ggaggatgga tattctaatt | 180 |
| agcctaatta gcctgattag ccctcgccag agttcactgt aaagctaacc cagcattaac | 240 |
| cttttaagtt aaagactaag agaatcatta tctcttttaca gtgaaatgcc acagctaaat | 300 |
| accactgtat gacctgctat catcacccca atactcctca cgttatttct catcacccaa | 360 |
| ctaaaaatac taaacacaca ctgccatctg cccacctcac caaaatttat taaaataaaa | 420 |
| aactacagta agccctgaga accaaaatga cgaaaattt attcgcttca ttcattaccc | 480 |
| ctacagtact aggcctaccc gccacagtac caatcatcct atttccccccc ttactggtcc | 540 |
| caacctccaa atacctcatc aacaaccgac taatcaccac tcaacaatga ctacttcaac | 600 |
| tcaccttaaa acaaataata acgatacata acattaaggg acgaacctgg tcccttatac | 660 |
| taatttccct gattattttt attgccacaa ctaatctcct cggactcttg ccccactcat | 720 |
| ttacaccaat cactatacat gtgtctattg aaacgtcact atgtgtgccc catgaatatg | 780 |
| tacatattat tatgtgatgt acatgattat gtacacatta tgtgccaatg aaataaataa | 840 |
| aattaaaagg taattcccaa ataaataaaa acagaaaatt ttaaaaagag agagagagag | 900 |
| atgagatggg gctttgggtg ggaacctggt tatggaaatc tgctgctgcc ctctttccct | 960 |
| taggaatgca agactttaat tatctccata ccaactgctt tgagatcacg ctggaactga | 1020 |
| gttgcgacaa gtttcccccc gaagaggagt tacagcggga gtggctgggt aatcgggaag | 1080 |
| ccctaatcca gttcctggaa caggtaaaat ctcatttgtt aactctcttg tttgcaaaaa | 1140 |
| gagaagtgct tctcaatggc aggcaagtgt ttcactggtt cagtctgact tttgctctga | 1200 |
| ctctgtccaa tatatctggg cgttcttctt ccattgagat tttattcatt tccaccttta | 1260 |
| ttt | 1263 |

<210> SEQ ID NO 5
<211> LENGTH: 18
<212> TYPE: DNA
<213> ORGANISM: Artificial Sequence
<220> FEATURE:
<223> OTHER INFORMATION: Primer complementary to mitochondrial DNA
      sequences in the CO1 encoding region of SEQ ID
      NO:2

-continued

```
<400> SEQUENCE: 5
ccttacacct agcaggta                                                    18

<210> SEQ ID NO 6
<211> LENGTH: 20
<212> TYPE: DNA
<213> ORGANISM: Artificial Sequence
<220> FEATURE:
<223> OTHER INFORMATION: Primer complementary to mitochondrial DNA
      sequences in the CO1 encoding region of SEQ ID
      NO:2

<400> SEQUENCE: 6
acgccgatga atatgatagc                                                  20

<210> SEQ ID NO 7
<211> LENGTH: 27
<212> TYPE: DNA
<213> ORGANISM: Artificial Sequence
<220> FEATURE:
<223> OTHER INFORMATION: Primer

<400> SEQUENCE: 7
catgcagcgc aagtaggtct acaagac                                          27

<210> SEQ ID NO 8
<211> LENGTH: 27
<212> TYPE: DNA
<213> ORGANISM: Artificial Sequence
<220> FEATURE:
<223> OTHER INFORMATION: Primer

<400> SEQUENCE: 8
tgttatgtaa aggatgcgta gggatgg                                          27

<210> SEQ ID NO 9
<211> LENGTH: 22
<212> TYPE: DNA
<213> ORGANISM: Artificial Sequence
<220> FEATURE:
<223> OTHER INFORMATION: Primer

<400> SEQUENCE: 9
tatgagggcg tgatcatgaa ag                                               22

<210> SEQ ID NO 10
<211> LENGTH: 17
<212> TYPE: DNA
<213> ORGANISM: Artificial Sequence
<220> FEATURE:
<223> OTHER INFORMATION: Primer

<400> SEQUENCE: 10
ggcacggctg tccaagg                                                     17

<210> SEQ ID NO 11
<211> LENGTH: 17
<212> TYPE: DNA
<213> ORGANISM: Artificial Sequence
<220> FEATURE:
<223> OTHER INFORMATION: Primer

<400> SEQUENCE: 11
cccggcctgg tacactg                                                     17
```

```
<210> SEQ ID NO 12
<211> LENGTH: 18
<212> TYPE: DNA
<213> ORGANISM: Artificial Sequence
<220> FEATURE:
<223> OTHER INFORMATION: Primer

<400> SEQUENCE: 12
gcggacatgg aggacgtg                                                    18

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
cgatgccgat gacctgcaga ag                                               22

<210> SEQ ID NO 14
<211> LENGTH: 21
<212> TYPE: DNA
<213> ORGANISM: Artificial Sequence
<220> FEATURE:
<223> OTHER INFORMATION: Oligonucleotide primer corresponding to
      cytochrome c oxidase encoding mitochondrial DNA

<400> SEQUENCE: 14
gtccaatgct tcactcagcc a                                                21

<210> SEQ ID NO 15
<211> LENGTH: 21
<212> TYPE: DNA
<213> ORGANISM: Artificial Sequence
<220> FEATURE:
<223> OTHER INFORMATION: Oligonucleotide primer corresponding to
      cytochrome c oxidase encoding mitochondrial DNA

<400> SEQUENCE: 15
ttacagtcca atgcttcact c                                                21

<210> SEQ ID NO 16
<211> LENGTH: 18
<212> TYPE: DNA
<213> ORGANISM: Artificial Sequence
<220> FEATURE:
<223> OTHER INFORMATION: Oligonucleotide primer corresponding to
      cytochrome c oxidase encoding mitochondrial DNA

<400> SEQUENCE: 16
tatgcgggga aacgccat                                                    18

<210> SEQ ID NO 17
<211> LENGTH: 19
<212> TYPE: DNA
<213> ORGANISM: Artificial Sequence
<220> FEATURE:
<223> OTHER INFORMATION: Oligonucleotide primer corresponding to
      cytochrome c oxidase encoding mitochondrial DNA

<400> SEQUENCE: 17
tgtttatgcg gggaaacgc                                                   19

<210> SEQ ID NO 18
<211> LENGTH: 21
```

```
<212> TYPE: DNA
<213> ORGANISM: Artificial Sequence
<220> FEATURE:
<223> OTHER INFORMATION: Oligonucleotide primer corresponding to
      cytochrome c oxidase encoding mitochondrial DNA

<400> SEQUENCE: 18
ggcaactgac tagttcccct a                                            21

<210> SEQ ID NO 19
<211> LENGTH: 21
<212> TYPE: DNA
<213> ORGANISM: Artificial Sequence
<220> FEATURE:
<223> OTHER INFORMATION: Oligonucleotide primer corresponding to
      cytochrome c oxidase encoding mitochondrial DNA

<400> SEQUENCE: 19
aatcggaggc tttggcaact g                                            21

<210> SEQ ID NO 20
<211> LENGTH: 21
<212> TYPE: DNA
<213> ORGANISM: Artificial Sequence
<220> FEATURE:
<223> OTHER INFORMATION: Oligonucleotide primer corresponding to
      cytochrome c oxidase encoding mitochondrial DNA

<400> SEQUENCE: 20
gtttggtatt gggttatggc a                                            21

<210> SEQ ID NO 21
<211> LENGTH: 21
<212> TYPE: DNA
<213> ORGANISM: Artificial Sequence
<220> FEATURE:
<223> OTHER INFORMATION: Oligonucleotide primer corresponding to
      cytochrome c oxidase encoding mitochondrial DNA

<400> SEQUENCE: 21
tggtattggg ttatggcagg g                                            21

<210> SEQ ID NO 22
<211> LENGTH: 20
<212> TYPE: DNA
<213> ORGANISM: Artificial Sequence
<220> FEATURE:
<223> OTHER INFORMATION: Oligonucleotide primer corresponding to
      cytochrome c oxidase encoding mitochondrial DNA

<400> SEQUENCE: 22
ggccatcaat ttcatcacaa                                              20

<210> SEQ ID NO 23
<211> LENGTH: 22
<212> TYPE: DNA
<213> ORGANISM: Artificial Sequence
<220> FEATURE:
<223> OTHER INFORMATION: Oligonucleotide primer corresponding to
      cytochrome c oxidase encoding mitochondrial DNA

<400> SEQUENCE: 23
tagcaggtgt ctcctctatc tt                                           22

<210> SEQ ID NO 24
<211> LENGTH: 25
<212> TYPE: DNA
```

```
<213> ORGANISM: Artificial Sequence
<220> FEATURE:
<223> OTHER INFORMATION: Oligonucleotide primer corresponding to
      cytochrome c oxidase encoding mitochondrial DNA

<400> SEQUENCE: 24
atacctatgt atccaaatgg ttctt                                              25

<210> SEQ ID NO 25
<211> LENGTH: 25
<212> TYPE: DNA
<213> ORGANISM: Artificial Sequence
<220> FEATURE:
<223> OTHER INFORMATION: Oligonucleotide primer corresponding to
      cytochrome c oxidase encoding mitochondrial DNA

<400> SEQUENCE: 25
ccatacctat gtatccaaat ggttc                                              25

<210> SEQ ID NO 26
<211> LENGTH: 25
<212> TYPE: DNA
<213> ORGANISM: Artificial Sequence
<220> FEATURE:
<223> OTHER INFORMATION: Oligonucleotide primer corresponding to
      cytochrome c oxidase encoding mitochondrial DNA

<400> SEQUENCE: 26
ggaataatct cccatattgt aactt                                              25

<210> SEQ ID NO 27
<211> LENGTH: 18
<212> TYPE: DNA
<213> ORGANISM: Artificial Sequence
<220> FEATURE:
<223> OTHER INFORMATION: Oligonucleotide primer corresponding to
      cytochrome c oxidase encoding mitochondrial DNA

<400> SEQUENCE: 27
caggccacct acggtgaa                                                      18

<210> SEQ ID NO 28
<211> LENGTH: 18
<212> TYPE: DNA
<213> ORGANISM: Artificial Sequence
<220> FEATURE:
<223> OTHER INFORMATION: Oligonucleotide primer corresponding to
      cytochrome c oxidase encoding mitochondrial DNA

<400> SEQUENCE: 28
gtcaggccac ctacggtg                                                      18

<210> SEQ ID NO 29
<211> LENGTH: 20
<212> TYPE: DNA
<213> ORGANISM: Artificial Sequence
<220> FEATURE:
<223> OTHER INFORMATION: Oligonucleotide primer corresponding to
      cytochrome c oxidase encoding mitochondrial DNA

<400> SEQUENCE: 29
agtgctctga gccctaggat                                                    20

<210> SEQ ID NO 30
<211> LENGTH: 20
<212> TYPE: DNA
<213> ORGANISM: Artificial Sequence
```

```
<220> FEATURE:
<223> OTHER INFORMATION: Oligonucleotide primer corresponding to
      cytochrome c oxidase encoding mitochondrial DNA

<400> SEQUENCE: 30
atgatctgct gcagtgctct                                              20

<210> SEQ ID NO 31
<211> LENGTH: 18
<212> TYPE: DNA
<213> ORGANISM: Artificial Sequence
<220> FEATURE:
<223> OTHER INFORMATION: Oligonucleotide primer corresponding to
      cytochrome c oxidase encoding mitochondrial DNA

<400> SEQUENCE: 31
attccggata ggccgaga                                                18

<210> SEQ ID NO 32
<211> LENGTH: 22
<212> TYPE: DNA
<213> ORGANISM: Artificial Sequence
<220> FEATURE:
<223> OTHER INFORMATION: Oligonucleotide primer corresponding to
      cytochrome c oxidase encoding mitochondrial DNA

<400> SEQUENCE: 32
tcggcgtaaa tctaactttc tt                                           22

<210> SEQ ID NO 33
<211> LENGTH: 19
<212> TYPE: DNA
<213> ORGANISM: Artificial Sequence
<220> FEATURE:
<223> OTHER INFORMATION: Oligonucleotide primer corresponding to
      cytochrome c oxidase encoding mitochondrial DNA

<400> SEQUENCE: 33
ggggttcgat tccttcctt                                               19

<210> SEQ ID NO 34
<211> LENGTH: 19
<212> TYPE: DNA
<213> ORGANISM: Artificial Sequence
<220> FEATURE:
<223> OTHER INFORMATION: Oligonucleotide primer corresponding to
      cytochrome c oxidase encoding mitochondrial DNA

<400> SEQUENCE: 34
ttggcttgaa accagcttt                                               19

<210> SEQ ID NO 35
<211> LENGTH: 24
<212> TYPE: DNA
<213> ORGANISM: Artificial Sequence
<220> FEATURE:
<223> OTHER INFORMATION: Oligonucleotide primer corresponding to
      cytochrome c oxidase encoding mitochondrial DNA

<400> SEQUENCE: 35
ttgtcaaagt taaattatag gcta                                         24

<210> SEQ ID NO 36
<211> LENGTH: 24
<212> TYPE: DNA
<213> ORGANISM: Artificial Sequence
<220> FEATURE:
```

```
<223> OTHER INFORMATION: Oligonucleotide primer corresponding to
      cytochrome c oxidase encoding mitochondrial DNA

<400> SEQUENCE: 36
gtcaaagtta aattataggc taaa                                              24

<210> SEQ ID NO 37
<211> LENGTH: 23
<212> TYPE: DNA
<213> ORGANISM: Artificial Sequence
<220> FEATURE:
<223> OTHER INFORMATION: Oligonucleotide primer corresponding to
      cytochrome c oxidase encoding mitochondrial DNA

<400> SEQUENCE: 37
acctcgtctg ttatgtaaag gat                                               23

<210> SEQ ID NO 38
<211> LENGTH: 23
<212> TYPE: DNA
<213> ORGANISM: Artificial Sequence
<220> FEATURE:
<223> OTHER INFORMATION: Oligonucleotide primer corresponding to
      cytochrome c oxidase encoding mitochondrial DNA

<400> SEQUENCE: 38
tgacctcgtc tgttatgtaa agg                                               23

<210> SEQ ID NO 39
<211> LENGTH: 20
<212> TYPE: DNA
<213> ORGANISM: Artificial Sequence
<220> FEATURE:
<223> OTHER INFORMATION: Oligonucleotide primer corresponding to
      cytochrome c oxidase encoding mitochondrial DNA

<400> SEQUENCE: 39
cgccatcatc ctagtcctca                                                   20

<210> SEQ ID NO 40
<211> LENGTH: 23
<212> TYPE: DNA
<213> ORGANISM: Artificial Sequence
<220> FEATURE:
<223> OTHER INFORMATION: Oligonucleotide primer corresponding to
      cytochrome c oxidase encoding mitochondrial DNA

<400> SEQUENCE: 40
atgagtgcaa gacgtcttgt gat                                               23

<210> SEQ ID NO 41
<211> LENGTH: 23
<212> TYPE: DNA
<213> ORGANISM: Artificial Sequence
<220> FEATURE:
<223> OTHER INFORMATION: Oligonucleotide primer corresponding to
      cytochrome c oxidase encoding mitochondrial DNA

<400> SEQUENCE: 41
aatcgagtag tactcccgat tga                                               23

<210> SEQ ID NO 42
<211> LENGTH: 23
<212> TYPE: DNA
<213> ORGANISM: Artificial Sequence
<220> FEATURE:
<223> OTHER INFORMATION: Oligonucleotide primer corresponding to
``` cytochrome c oxidase encoding mitochondrial DNA

<400> SEQUENCE: 42
gagtagtact cccgattgaa gcc                                    23

<210> SEQ ID NO 43
<211> LENGTH: 24
<212> TYPE: DNA
<213> ORGANISM: Artificial Sequence
<220> FEATURE:
<223> OTHER INFORMATION: Oligonucleotide primer corresponding to
      cytochrome c oxidase encoding mitochondrial DNA

<400> SEQUENCE: 43
gttagcttta cagtgggctc taga                                   24

<210> SEQ ID NO 44
<211> LENGTH: 24
<212> TYPE: DNA
<213> ORGANISM: Artificial Sequence
<220> FEATURE:
<223> OTHER INFORMATION: Oligonucleotide primer corresponding to
      cytochrome c oxidase encoding mitochondrial DNA

<400> SEQUENCE: 44
agttagcttt acagtgggct ctag                                   24

<210> SEQ ID NO 45
<211> LENGTH: 24
<212> TYPE: DNA
<213> ORGANISM: Artificial Sequence
<220> FEATURE:
<223> OTHER INFORMATION: Oligonucleotide primer corresponding to
      cytochrome c oxidase encoding mitochondrial DNA

<400> SEQUENCE: 45
acttctagta agcctctacc tgca                                   24

<210> SEQ ID NO 46
<211> LENGTH: 24
<212> TYPE: DNA
<213> ORGANISM: Artificial Sequence
<220> FEATURE:
<223> OTHER INFORMATION: Oligonucleotide primer corresponding to
      cytochrome c oxidase encoding mitochondrial DNA

<400> SEQUENCE: 46
ttctagtaag cctctacctg cacg                                   24

<210> SEQ ID NO 47
<211> LENGTH: 25
<212> TYPE: DNA
<213> ORGANISM: Artificial Sequence
<220> FEATURE:
<223> OTHER INFORMATION: Oligonucleotide primer corresponding to
      cytochrome c oxidase encoding mitochondrial DNA

<400> SEQUENCE: 47
aggtaataaa taggattatc ccgta                                  25

<210> SEQ ID NO 48
<211> LENGTH: 25
<212> TYPE: DNA
<213> ORGANISM: Artificial Sequence
<220> FEATURE:
<223> OTHER INFORMATION: Oligonucleotide primer corresponding to
      cytochrome c oxidase encoding mitochondrial DNA

```
<400> SEQUENCE: 48
aataaatagg attatcccgt atcga                                    25

<210> SEQ ID NO 49
<211> LENGTH: 19
<212> TYPE: DNA
<213> ORGANISM: Artificial Sequence
<220> FEATURE:
<223> OTHER INFORMATION: Oligonucleotide primer corresponding to
      cytochrome c oxidase encoding mitochondrial DNA

<400> SEQUENCE: 49
ccacacacca cctgtccaa                                           19

<210> SEQ ID NO 50
<211> LENGTH: 19
<212> TYPE: DNA
<213> ORGANISM: Artificial Sequence
<220> FEATURE:
<223> OTHER INFORMATION: Oligonucleotide primer corresponding to
      cytochrome c oxidase encoding mitochondrial DNA

<400> SEQUENCE: 50
accacacacc acctgtcca                                           19

<210> SEQ ID NO 51
<211> LENGTH: 23
<212> TYPE: DNA
<213> ORGANISM: Artificial Sequence
<220> FEATURE:
<223> OTHER INFORMATION: Oligonucleotide primer corresponding to
      cytochrome c oxidase encoding mitochondrial DNA

<400> SEQUENCE: 51
aagggagact cgaagtactc tga                                      23

<210> SEQ ID NO 52
<211> LENGTH: 23
<212> TYPE: DNA
<213> ORGANISM: Artificial Sequence
<220> FEATURE:
<223> OTHER INFORMATION: Oligonucleotide primer corresponding to
      cytochrome c oxidase encoding mitochondrial DNA

<400> SEQUENCE: 52
tgggtctcta ttttaccctc cta                                      23

<210> SEQ ID NO 53
<211> LENGTH: 23
<212> TYPE: DNA
<213> ORGANISM: Artificial Sequence
<220> FEATURE:
<223> OTHER INFORMATION: Oligonucleotide primer corresponding to
      cytochrome c oxidase encoding mitochondrial DNA

<400> SEQUENCE: 53
tattacaatt ttactgggtc tct                                      23

<210> SEQ ID NO 54
<211> LENGTH: 25
<212> TYPE: DNA
<213> ORGANISM: Artificial Sequence
<220> FEATURE:
<223> OTHER INFORMATION: Oligonucleotide primer corresponding to
      cytochrome c oxidase encoding mitochondrial DNA
```

-continued

<400> SEQUENCE: 54
actagttaat tggaagttaa cggta                                          25

<210> SEQ ID NO 55
<211> LENGTH: 23
<212> TYPE: DNA
<213> ORGANISM: Artificial Sequence
<220> FEATURE:
<223> OTHER INFORMATION: Oligonucleotide primer corresponding to NADH
      dehydrogenase encoding mitochondrial DNA

<400> SEQUENCE: 55
gaggttcaat tcctcttctt aac                                            23

<210> SEQ ID NO 56
<211> LENGTH: 22
<212> TYPE: DNA
<213> ORGANISM: Artificial Sequence
<220> FEATURE:
<223> OTHER INFORMATION: Oligonucleotide primer corresponding to NADH
      dehydrogenase encoding mitochondrial DNA

<400> SEQUENCE: 56
ttgagtaaac ggctaggcta ga                                             22

<210> SEQ ID NO 57
<211> LENGTH: 20
<212> TYPE: DNA
<213> ORGANISM: Artificial Sequence
<220> FEATURE:
<223> OTHER INFORMATION: Oligonucleotide primer corresponding to NADH
      dehydrogenase encoding mitochondrial DNA

<400> SEQUENCE: 57
ctggtcaacc tcaacctagg                                                20

<210> SEQ ID NO 58
<211> LENGTH: 16
<212> TYPE: DNA
<213> ORGANISM: Artificial Sequence
<220> FEATURE:
<223> OTHER INFORMATION: Oligonucleotide primer corresponding to NADH
      dehydrogenase encoding mitochondrial DNA

<400> SEQUENCE: 58
ggcctgcggc gtattc                                                    16

<210> SEQ ID NO 59
<211> LENGTH: 17
<212> TYPE: DNA
<213> ORGANISM: Artificial Sequence
<220> FEATURE:
<223> OTHER INFORMATION: Oligonucleotide primer corresponding to NADH
      dehydrogenase encoding mitochondrial DNA

<400> SEQUENCE: 59
ccgaagggga gtccgaa                                                   17

<210> SEQ ID NO 60
<211> LENGTH: 25
<212> TYPE: DNA
<213> ORGANISM: Artificial Sequence
<220> FEATURE:
<223> OTHER INFORMATION: Oligonucleotide primer corresponding to NADH
      dehydrogenase encoding mitochondrial DNA

<400> SEQUENCE: 60

```
atcaaagtaa ctcttttatc agaca                                        25

<210> SEQ ID NO 61
<211> LENGTH: 20
<212> TYPE: DNA
<213> ORGANISM: Artificial Sequence
<220> FEATURE:
<223> OTHER INFORMATION: Oligonucleotide primer corresponding to NADH
      dehydrogenase encoding mitochondrial DNA

<400> SEQUENCE: 61
ttggttatac ccttcccgta                                              20

<210> SEQ ID NO 62
<211> LENGTH: 26
<212> TYPE: DNA
<213> ORGANISM: Artificial Sequence
<220> FEATURE:
<223> OTHER INFORMATION: Oligonucleotide primer corresponding to NADH
      dehydrogenase encoding mitochondrial DNA

<400> SEQUENCE: 62
ctattcctag ttttattgct atagct                                       26

<210> SEQ ID NO 63
<211> LENGTH: 22
<212> TYPE: DNA
<213> ORGANISM: Artificial Sequence
<220> FEATURE:
<223> OTHER INFORMATION: Oligonucleotide primer corresponding to NADH
      dehydrogenase encoding mitochondrial DNA

<400> SEQUENCE: 63
acaatatact ctccggacaa tg                                           22

<210> SEQ ID NO 64
<211> LENGTH: 23
<212> TYPE: DNA
<213> ORGANISM: Artificial Sequence
<220> FEATURE:
<223> OTHER INFORMATION: Oligonucleotide primer corresponding to NADH
      dehydrogenase encoding mitochondrial DNA

<400> SEQUENCE: 64
gaatggttat gttagggttg tac                                          23

<210> SEQ ID NO 65
<211> LENGTH: 22
<212> TYPE: DNA
<213> ORGANISM: Artificial Sequence
<220> FEATURE:
<223> OTHER INFORMATION: Oligonucleotide primer corresponding to NADH
      dehydrogenase encoding mitochondrial DNA

<400> SEQUENCE: 65
agctacgcaa aatcttagca ta                                           22

<210> SEQ ID NO 66
<211> LENGTH: 19
<212> TYPE: DNA
<213> ORGANISM: Artificial Sequence
<220> FEATURE:
<223> OTHER INFORMATION: Oligonucleotide primer corresponding to NADH
      dehydrogenase encoding mitochondrial DNA

<400> SEQUENCE: 66
```

-continued

```
agggtgatgg tggctatga                                                19
```

<210> SEQ ID NO 67
<211> LENGTH: 15
<212> TYPE: DNA
<213> ORGANISM: Artificial Sequence
<220> FEATURE:
<223> OTHER INFORMATION: Oligonucleotide primer corresponding to NADH
      dehydrogenase encoding mitochondrial DNA

<400> SEQUENCE: 67

```
cccgctaacc ggctt                                                    15
```

<210> SEQ ID NO 68
<211> LENGTH: 18
<212> TYPE: DNA
<213> ORGANISM: Artificial Sequence
<220> FEATURE:
<223> OTHER INFORMATION: Oligonucleotide primer corresponding to NADH
      dehydrogenase encoding mitochondrial DNA

<400> SEQUENCE: 68

```
agggctttga aggctctt                                                 18
```

<210> SEQ ID NO 69
<211> LENGTH: 25
<212> TYPE: DNA
<213> ORGANISM: Artificial Sequence
<220> FEATURE:
<223> OTHER INFORMATION: Oligonucleotide primer corresponding to NADH
      dehydrogenase encoding mitochondrial DNA

<400> SEQUENCE: 69

```
tttcgactca ttaaattatg ataat                                         25
```

<210> SEQ ID NO 70
<211> LENGTH: 25
<212> TYPE: DNA
<213> ORGANISM: Artificial Sequence
<220> FEATURE:
<223> OTHER INFORMATION: Oligonucleotide primer corresponding to NADH
      dehydrogenase encoding mitochondrial DNA

<400> SEQUENCE: 70

```
catgtcagtg gtagtaatat aattg                                         25
```

<210> SEQ ID NO 71
<211> LENGTH: 22
<212> TYPE: DNA
<213> ORGANISM: Artificial Sequence
<220> FEATURE:
<223> OTHER INFORMATION: Oligonucleotide primer corresponding to NADH
      dehydrogenase encoding mitochondrial DNA

<400> SEQUENCE: 71

```
cacatatggc ctagactacg ta                                            22
```

<210> SEQ ID NO 72
<211> LENGTH: 23
<212> TYPE: DNA
<213> ORGANISM: Artificial Sequence
<220> FEATURE:
<223> OTHER INFORMATION: Oligonucleotide primer corresponding to NADH
      dehydrogenase encoding mitochondrial DNA

<400> SEQUENCE: 72

```
ataattaagg agatttgtag gga                                           23
```

<210> SEQ ID NO 73
<211> LENGTH: 19
<212> TYPE: DNA
<213> ORGANISM: Artificial Sequence
<220> FEATURE:
<223> OTHER INFORMATION: Oligonucleotide primer corresponding to NADH dehydrogenase encoding mitochondrial DNA

<400> SEQUENCE: 73
ccaacgccac ttatccagt                                                19

<210> SEQ ID NO 74
<211> LENGTH: 25
<212> TYPE: DNA
<213> ORGANISM: Artificial Sequence
<220> FEATURE:
<223> OTHER INFORMATION: Oligonucleotide primer corresponding to NADH dehydrogenase encoding mitochondrial DNA

<400> SEQUENCE: 74
aagctattgt gtaagctagt catat                                         25

<210> SEQ ID NO 75
<211> LENGTH: 25
<212> TYPE: DNA
<213> ORGANISM: Artificial Sequence
<220> FEATURE:
<223> OTHER INFORMATION: Oligonucleotide primer corresponding to NADH dehydrogenase encoding mitochondrial DNA

<400> SEQUENCE: 75
ctcactaaac attctactac tcact                                         25

<210> SEQ ID NO 76
<211> LENGTH: 21
<212> TYPE: DNA
<213> ORGANISM: Artificial Sequence
<220> FEATURE:
<223> OTHER INFORMATION: Oligonucleotide primer corresponding to NADH dehydrogenase encoding mitochondrial DNA

<400> SEQUENCE: 76
gtggctgatt gaagagtatg c                                             21

<210> SEQ ID NO 77
<211> LENGTH: 24
<212> TYPE: DNA
<213> ORGANISM: Artificial Sequence
<220> FEATURE:
<223> OTHER INFORMATION: Oligonucleotide primer corresponding to NADH dehydrogenase encoding mitochondrial DNA

<400> SEQUENCE: 77
cctatgaggc ataattataa caag                                          24

<210> SEQ ID NO 78
<211> LENGTH: 22
<212> TYPE: DNA
<213> ORGANISM: Artificial Sequence
<220> FEATURE:
<223> OTHER INFORMATION: Oligonucleotide primer corresponding to NADH dehydrogenase encoding mitochondrial DNA

<400> SEQUENCE: 78
acgtggttac tagcacagag ag                                            22

<210> SEQ ID NO 79
<211> LENGTH: 19
<212> TYPE: DNA
<213> ORGANISM: Artificial Sequence
<220> FEATURE:
<223> OTHER INFORMATION: Oligonucleotide primer corresponding to NADH
      dehydrogenase encoding mitochondrial DNA

<400> SEQUENCE: 79
tgacttctag caagcctcg                                                  19

<210> SEQ ID NO 80
<211> LENGTH: 23
<212> TYPE: DNA
<213> ORGANISM: Artificial Sequence
<220> FEATURE:
<223> OTHER INFORMATION: Oligonucleotide primer corresponding to NADH
      dehydrogenase encoding mitochondrial DNA

<400> SEQUENCE: 80
acaatctgat gttttggtta aac                                             23

<210> SEQ ID NO 81
<211> LENGTH: 22
<212> TYPE: DNA
<213> ORGANISM: Artificial Sequence
<220> FEATURE:
<223> OTHER INFORMATION: Oligonucleotide primer corresponding to NADH
      dehydrogenase encoding mitochondrial DNA

<400> SEQUENCE: 81
ctcatcctaa ccctactcct aa                                              22

<210> SEQ ID NO 82
<211> LENGTH: 19
<212> TYPE: DNA
<213> ORGANISM: Artificial Sequence
<220> FEATURE:
<223> OTHER INFORMATION: Oligonucleotide primer corresponding to NADH
      dehydrogenase encoding mitochondrial DNA

<400> SEQUENCE: 82
gcgatggcta ttgaggagt                                                  19

<210> SEQ ID NO 83
<211> LENGTH: 20
<212> TYPE: DNA
<213> ORGANISM: Artificial Sequence
<220> FEATURE:
<223> OTHER INFORMATION: Oligonucleotide primer corresponding to NADH
      dehydrogenase encoding mitochondrial DNA

<400> SEQUENCE: 83
gctaacccca ctaaaacact                                                 20

<210> SEQ ID NO 84
<211> LENGTH: 20
<212> TYPE: DNA
<213> ORGANISM: Artificial Sequence
<220> FEATURE:
<223> OTHER INFORMATION: Oligonucleotide primer corresponding to NADH
      dehydrogenase encoding mitochondrial DNA

<400> SEQUENCE: 84
ttcatatcat tggtcgtggt                                                 20

<210> SEQ ID NO 85
<211> LENGTH: 25
<212> TYPE: DNA
<213> ORGANISM: Artificial Sequence
<220> FEATURE:
<223> OTHER INFORMATION: Oligonucleotide primer corresponding to NADH
      dehydrogenase encoding mitochondrial DNA

<400> SEQUENCE: 85
tagtaccgtt aacttccaat taact                                              25

<210> SEQ ID NO 86
<211> LENGTH: 24
<212> TYPE: DNA
<213> ORGANISM: Artificial Sequence
<220> FEATURE:
<223> OTHER INFORMATION: Oligonucleotide primer corresponding to NADH
      dehydrogenase encoding mitochondrial DNA

<400> SEQUENCE: 86
tcataattta atgagtcgaa atca                                               24

<210> SEQ ID NO 87
<211> LENGTH: 21
<212> TYPE: DNA
<213> ORGANISM: Artificial Sequence
<220> FEATURE:
<223> OTHER INFORMATION: Oligonucleotide primer corresponding to NADH
      dehydrogenase encoding mitochondrial DNA

<400> SEQUENCE: 87
cagctatcca ttggtcttag g                                                  21

<210> SEQ ID NO 88
<211> LENGTH: 25
<212> TYPE: DNA
<213> ORGANISM: Artificial Sequence
<220> FEATURE:
<223> OTHER INFORMATION: Oligonucleotide primer corresponding to NADH
      dehydrogenase encoding mitochondrial DNA

<400> SEQUENCE: 88
tatttgaaga actgattaat gtttg                                              25

<210> SEQ ID NO 89
<211> LENGTH: 21
<212> TYPE: DNA
<213> ORGANISM: Artificial Sequence
<220> FEATURE:
<223> OTHER INFORMATION: Oligonucleotide primer corresponding to NADH
      dehydrogenase encoding mitochondrial DNA

<400> SEQUENCE: 89
agcattgttc gttacatggt c                                                  21

<210> SEQ ID NO 90
<211> LENGTH: 21
<212> TYPE: DNA
<213> ORGANISM: Artificial Sequence
<220> FEATURE:
<223> OTHER INFORMATION: Oligonucleotide primer corresponding to NADH
      dehydrogenase encoding mitochondrial DNA

<400> SEQUENCE: 90
ggcttggatt agcgtttaga a                                                  21

<210> SEQ ID NO 91

```
<211> LENGTH: 20
<212> TYPE: DNA
<213> ORGANISM: Artificial Sequence
<220> FEATURE:
<223> OTHER INFORMATION: Oligonucleotide primer corresponding to NADH
      dehydrogenase encoding mitochondrial DNA

<400> SEQUENCE: 91
tcatcctcgc cttagcatga                                              20

<210> SEQ ID NO 92
<211> LENGTH: 23
<212> TYPE: DNA
<213> ORGANISM: Artificial Sequence
<220> FEATURE:
<223> OTHER INFORMATION: Oligonucleotide primer corresponding to NADH
      dehydrogenase encoding mitochondrial DNA

<400> SEQUENCE: 92
ttttgatgtc attttgtgta agg                                          23

<210> SEQ ID NO 93
<211> LENGTH: 23
<212> TYPE: DNA
<213> ORGANISM: Artificial Sequence
<220> FEATURE:
<223> OTHER INFORMATION: Oligonucleotide primer corresponding to NADH
      dehydrogenase encoding mitochondrial DNA

<400> SEQUENCE: 93
caaactctaa cactatgctt agg                                          23

<210> SEQ ID NO 94
<211> LENGTH: 20
<212> TYPE: DNA
<213> ORGANISM: Artificial Sequence
<220> FEATURE:
<223> OTHER INFORMATION: Oligonucleotide primer corresponding to NADH
      dehydrogenase encoding mitochondrial DNA

<400> SEQUENCE: 94
atgtttgcgg tttcgatgat                                              20

<210> SEQ ID NO 95
<211> LENGTH: 20
<212> TYPE: DNA
<213> ORGANISM: Artificial Sequence
<220> FEATURE:
<223> OTHER INFORMATION: Oligonucleotide primer corresponding to NADH
      dehydrogenase encoding mitochondrial DNA

<400> SEQUENCE: 95
cattggcagc ctagcattag                                              20

<210> SEQ ID NO 96
<211> LENGTH: 26
<212> TYPE: DNA
<213> ORGANISM: Artificial Sequence
<220> FEATURE:
<223> OTHER INFORMATION: Oligonucleotide primer corresponding to NADH
      dehydrogenase encoding mitochondrial DNA

<400> SEQUENCE: 96
gattttattt taagtttgtt ggttag                                       26

<210> SEQ ID NO 97
<211> LENGTH: 19
```

```
<212> TYPE: DNA
<213> ORGANISM: Artificial Sequence
<220> FEATURE:
<223> OTHER INFORMATION: Oligonucleotide primer corresponding to NADH
      dehydrogenase encoding mitochondrial DNA

<400> SEQUENCE: 97
aaactcacag ccctcgctg                                                 19

<210> SEQ ID NO 98
<211> LENGTH: 24
<212> TYPE: DNA
<213> ORGANISM: Artificial Sequence
<220> FEATURE:
<223> OTHER INFORMATION: Oligonucleotide primer corresponding to NADH
      dehydrogenase encoding mitochondrial DNA

<400> SEQUENCE: 98
tatgtgatta ggagtagggt tagg                                           24

<210> SEQ ID NO 99
<211> LENGTH: 23
<212> TYPE: DNA
<213> ORGANISM: Artificial Sequence
<220> FEATURE:
<223> OTHER INFORMATION: Oligonucleotide primer corresponding to ATP
      synthetase subunits 8/6 encoding mitochondrial DNA

<400> SEQUENCE: 99
gcccactgta aagctaactt agc                                            23

<210> SEQ ID NO 100
<211> LENGTH: 22
<212> TYPE: DNA
<213> ORGANISM: Artificial Sequence
<220> FEATURE:
<223> OTHER INFORMATION: Oligonucleotide primer corresponding to ATP
      synthetase subunits 8/6 encoding mitochondrial DNA

<400> SEQUENCE: 100
tagtcggttg ttgatgagat at                                             22

<210> SEQ ID NO 101
<211> LENGTH: 17
<212> TYPE: DNA
<213> ORGANISM: Artificial Sequence
<220> FEATURE:
<223> OTHER INFORMATION: Oligonucleotide primer corresponding to ATP
      synthetase subunits 8/6 encoding mitochondrial DNA

<400> SEQUENCE: 101
agtcggttgt tgatgag                                                   17

<210> SEQ ID NO 102
<211> LENGTH: 23
<212> TYPE: DNA
<213> ORGANISM: Artificial Sequence
<220> FEATURE:
<223> OTHER INFORMATION: Oligonucleotide primer corresponding to ATP
      synthetase subunits 8/6 encoding mitochondrial DNA

<400> SEQUENCE: 102
ggcctacccg ccgcagtact gat                                            23

<210> SEQ ID NO 103
<211> LENGTH: 23
<212> TYPE: DNA
```

```
<213> ORGANISM: Artificial Sequence
<220> FEATURE:
<223> OTHER INFORMATION: Oligonucleotide primer corresponding to ATP
      synthetase subunits 8/6 encoding mitochondrial DNA

<400> SEQUENCE: 103
tgtaggtgtg ccttgtggta aga                                      23

<210> SEQ ID NO 104
<211> LENGTH: 22
<212> TYPE: DNA
<213> ORGANISM: Artificial Sequence
<220> FEATURE:
<223> OTHER INFORMATION: Oligonucleotide primer corresponding to ATP
      synthetase subunits 8/6 encoding mitochondrial DNA

<400> SEQUENCE: 104
attataggct ttcgctctaa ga                                       22

<210> SEQ ID NO 105
<211> LENGTH: 21
<212> TYPE: DNA
<213> ORGANISM: Artificial Sequence
<220> FEATURE:
<223> OTHER INFORMATION: Oligonucleotide primer corresponding to ATP
      synthetase subunits 8/6 encoding mitochondrial DNA

<400> SEQUENCE: 105
ccaaccaccc aactatctat a                                        21

<210> SEQ ID NO 106
<211> LENGTH: 22
<212> TYPE: DNA
<213> ORGANISM: Artificial Sequence
<220> FEATURE:
<223> OTHER INFORMATION: Oligonucleotide primer corresponding to ATP
      synthetase subunits 8/6 encoding mitochondrial DNA

<400> SEQUENCE: 106
atatgatagg catgtgattg gt                                       22

<210> SEQ ID NO 107
<211> LENGTH: 25
<212> TYPE: DNA
<213> ORGANISM: Artificial Sequence
<220> FEATURE:
<223> OTHER INFORMATION: Oligonucleotide primer corresponding to ATP
      synthetase subunits 8/6 encoding mitochondrial DNA

<400> SEQUENCE: 107
tagcattaac cttttaagtt aaaga                                    25

<210> SEQ ID NO 108
<211> LENGTH: 19
<212> TYPE: DNA
<213> ORGANISM: Artificial Sequence
<220> FEATURE:
<223> OTHER INFORMATION: Oligonucleotide primer corresponding to ATP
      synthetase subunits 8/6 encoding mitochondrial DNA

<400> SEQUENCE: 108
tcgttcattt tggttctca                                           19
```

DIAGNOSTIC METHOD BASED ON QUANTIFICATION OF EXTRAMITOCHONDRIAL DNA

CROSS-REFERENCE TO RELATED APPLICATIONS

This application is a Continuation-In-Part of U.S. application Ser. No. 09/097,889, filed Jun. 15, 1998 now U.S. Pat. No. 6,218,117, and of U.S. application Ser. No. 09/098,079, filed Jun. 15, 1998.

TECHNICAL FIELD

The present invention relates generally to diseases in which altered mitochondrial function, such as free radical mediated oxidative injury, leads to tissue degeneration and, more specifically, to compositions and methods for detecting predisposition to such diseases by quantifying extramitochondrial DNA.

BACKGROUND OF THE INVENTION

A number of degenerative diseases are thought to be caused by or be associated with alterations in mitochondrial function. These diseases include Alzheimer's Disease, diabetes mellitus, Parkinson's Disease, Huntington's disease, dystonia, Leber's hereditary optic neuropathy, schizophrenia, and myodegenerative disorders such as "mitochondrial encephalopathy, lactic acidosis, and stroke" (MELAS), and "myoclonic epilepsy ragged red fiber syndrome" (MERRF). Other diseases involving altered metabolism or respiration within cells may also be regarded as diseases associated with altered mitochondrial function.

Functional mitochondria contain gene products encoded by mitochondrial genes situated in mitochondrial DNA (mtDNA) and by extramitochondrial genes not situated in the circular mitochondrial genome. The 16.5 kb mtDNA encodes 22 tRNAs, two ribosomal RNAs (rRNA) and only 13 enzymes of the electron transport chain (ETC), the elaborate multi-complex mitochondrial assembly where, for example, respiratory oxidative phosphorylation takes place. The overwhelming majority of mitochondrial structural and functional proteins are encoded by extramitochondrial, and in most cases presumably nuclear genes. Accordingly, mitochondrial and extramitochondrial genes may interact directly or indirectly via gene products and their downstream intermediates, including metabolites, catabolites, substrates, precursors, cofactors and the like. Alterations in mitochondrial function, for example impaired electron transport activity, defective oxidative phosphorylation or increased free radical production, may therefore arise as the result of defective mtDNA, defective extramitochondrial DNA, defective mitochondrial or extramitochondrial gene products, defective downstream intermediates or a combination of these and other factors.

Mitochondria are the subcellular organelles that manufacture bioenergetically essential adenosine triphosphate (ATP) by oxidative phosphorylation. Defective mitochondrial activity, including failure at any step of the ETC, may result in the generation of highly reactive free radicals that have the potential of damaging cells and tissues. These free radicals may include reactive oxygen species (ROS) such as superoxide, peroxynitrite and hydroxyl radicals, and potentially other reactive species that may be toxic to cells. For example, oxygen free radical induced lipid peroxidation is a well established pathogenetic mechanism in central nervous system (CNS) injury, such as that found in a number of degenerative diseases, and in ischemia (i.e., stroke).

There are at least two deleterious consequences of exposure to reactive free radicals arising from mitochondrial dysfunction that adversely impact the mitochondria themselves. First, free radical mediated damage may inactivate one or more of the myriad proteins of the ETC. According to generally accepted theories of mitochondrial function, proper ETC respiratory activity requires maintenance of an electrochemical potential in the inner mitochondrial membrane by a coupled chemiosmotic mechanism. Free radical oxidative activity may dissipate this membrane potential, thereby preventing ATP biosynthesis and halting the production of a vital biochemical energy source. In addition, mitochondrial proteins such as cytochrome c and "apoptosis inducing factor" may leak out of the mitochondria after permeability transition and may induce the genetically programmed cell suicide sequence known as apoptosis or programmed cell death (PCD).

Second, free radical mediated damage may result in catastrophic mitochondrial collapse that has been termed "transition permeability". For example, rapid mitochondrial permeability transition likely entails changes in the inner mitochondrial transmembrane protein adenylate translocase that results in the formation of a "pore." In any event, because permeability transition is potentiated by free radical exposure, it may be more likely to occur in the mitochondria of cells from patients having mitochondria associated diseases that are chronically exposed to such reactive free radicals.

Altered mitochondrial function characteristic of the mitochondria associated diseases may also be related to loss of mitochondrial membrane electrochemical potential by mechanisms other than free radical oxidation, and such transition permeability may result from direct or indirect effects of mitochondrial genes, gene products or related downstream mediator molecules and/or extramitochondrial genes, gene products or related downstream mediators, or from other known or unknown causes.

Diabetes mellitus is a common, degenerative disease affecting 5 to 10 percent of the population in developed countries. The propensity for developing diabetes mellitus is reportedly maternally inherited, suggesting a mitochondrial genetic involvement. (Alcolado, J. C. and Alcolado, R., *Br. Med. J.* 302:1178–1180 (1991); Reny, S. L., *International J. Epidem.* 23:886–890 (1994)). Diabetes is a heterogenous disorder with a strong genetic component; monozygotic twins are highly concordant and there is a high incidence of the disease among first degree relatives of affected individuals.

At the cellular level, the degenerative phenotype that may be characteristic of late onset diabetes mellitus includes indicators of altered mitochondrial respiratory function, for example impaired insulin secretion, decreased ATP synthesis and increased levels of reactive oxygen species. Studies have shown that diabetes mellitus may be preceded by or associated with certain related disorders. For example, it is estimated that forty million individuals in the U.S. suffer from late onset impaired glucose tolerance (IGT). IGT patients fail to respond to glucose with increased insulin secretion. A small percentage of IGT individuals (5–10%) progress to insulin deficient on-insulin dependent diabetes (NIDDM) each year. Some of these individuals further progress to insulin dependent diabetes mellitus (IDDM). These forms of diabetes ellitus, NIDDM and IDDM, are associated with decreased release of insulin by pancreatic beta cells and/or a decreased end-organ response to insulin. Other symptoms of diabetes mellitus and conditions that precede or are associated with diabetes mellitus include obesity, vascular pathologies, peripheral and sensory neuropathies, blindness and deafness.

Parkinson's disease (PD) is a progressive, neurodegenerative disorder associated with altered mitochondrial function and characterized by the loss and/or atrophy of dopamine-containing neurons in the pars compacta of the substantia nigra of the brain. Like Alzheimer's Disease (AD), PD also afflicts the elderly. It is characterized by bradykinesia (slow movement), rigidity and a resting tremor. Although L-Dopa treatment reduces tremors in most patients for a while, ultimately the tremors become more and more uncontrollable, making it difficult or impossible for patients to even feed themselves or meet their own basic hygiene needs.

It has been shown that the neurotoxin 1-methyl-4-phenyl-1,2,3,6-tetrahydropyridine (MPTP) induces parkinsonism in animals and man at least in part through its effects on mitochondria. MPTP is converted to its active metabolite, MPP+, in dopamine neurons; it then becomes concentrated in the mitochondria. The MPP+ then selectively inhibits the mitochondrial enzyme NADH:ubiquinone oxidoreductase ("Complex I"), leading to the increased production of free radicals, reduced production of adenosine triphosphate, and ultimately, the death of affected dopamine neurons.

Mitochondrial Complex I is composed of 40–50 subunits; most are encoded by the nuclear genome and seven by the mitochondrial genome. Since parkinsonism may be induced by exposure to mitochondrial toxins that affect Complex I activity, it appears likely that defects in Complex I proteins may contribute to the pathogenesis of PD by causing a similar biochemical deficiency in Complex I activity. Indeed, defects in mitochondrial Complex I activity have been reported in the blood and brain of PD patients (Parker et al., *Am. J. Neurol.* 26:719–723, 1989).

Alzheimer's disease (AD) is a progressive neurodegenerative disorder that is characterized by loss and/or atrophy of neurons in discrete regions of the brain, and that is accompanied by extracellular deposits of β-amyloid and the intracellular accumulation of neurofibrillary tangles. It is a uniquely human disease, affecting over 13 million people worldwide. It is also a uniquely tragic disease. Many individuals who have lived normal, productive lives are slowly stricken with AD as they grow older, and the disease gradually robs them of their memory and other mental faculties. Eventually, they cease to recognize family and loved ones, and they often require continuous care until their eventual death.

There is evidence that defects in oxidative phosphorylation within the mitochondria are at least a partial cause of sporadic AD. The enzyme cytochrome c oxidase (COX), which makes up part of the mitochondrial electron transport chain (ETC), is present in normal amounts in AD patients; however, the catalytic activity of this enzyme in AD patients and in the brains of AD patients at autopsy has been found to be abnormally low. This suggests that the COX in AD patients is defective, leading to decreased catalytic activity that in some fashion causes or contributes to the symptoms that are characteristic of AD.

Focal defects in energy metabolism in the mitochondria, with accompanying increases in oxidative stress, may be associated with AD. It is well-established that energy metabolism is impaired in AD brain (Palmer et al., *Brain Res.* 645:338–42, 1994; Pappolla et al., *Am. J. Pathol.* 140:621–28, 1992; Jeandel et al., *Gerontol.* 35:275, 1989; Balazs et al.,*Neurochem Res.* 19:1131–37, 1994; Mecocci et al., *Ann. Neurol.* 36:747–751, 1994; Gsell et al., *J. Neurochem.* 64:1216–23, 1995). For example, regionally specific deficits in energy metabolism in AD brains have been reported in a number of positron emission tomography studies (Kuhl, et al., *J. Cereb. Blood Flow Metab.* 7:S406, 1987; Grady, et al., *J. Clin. Exp. Neuropsychol.* 10:576–96, 1988; Haxby et al.,*Arch. Neurol.* 47:753–60, 1990; Azari et al., *J. Cereb. Blood Flow Metab.* 13:438–47, 1993). Metabolic defects in the temporoparietal neocortex of AD patients apparently presage cognitive decline by several years. Skin fibroblasts from AD patients display decreased glucose utilization and increased oxidation of glucose, leading to the formation of glycosylation end products (Yan et al., *Proc. Nat. Acad. Sci.* USA 91:7787–91, 1994). Cortical tissue from postmortem AD brain shows decreased activity of the mitochondrial enzymes pyruvate dehydrogenase (Sheu et al., *Ann. Neurol.* 17:444–49, 1985) and a-ketoglutarate dehydrogenase (Mastrogiacomo et al., *J Neurochem.* 6:2007–14, 1994), which are both key enzymes in energy metabolism. Functional magnetic resonance spectroscopy studies have shown increased levels of inorganic phosphate relative to phosphocreatine in AD brain, suggesting an accumulation of precursors that arises from decreased ATP production by mitochondria (Pettegrew et al., *Neurobiol. of Aging* 15:117–32, 1994; Pettigrew et al., *Neurobiol. of Aging* 16:973–75, 1995). In addition, the levels of pyruvate, but not of glucose or lactate, are reported to be increased in the cerebrospinal fluid of AD patients, consistent with defects in cerebral mitochondrial electron transport chain (ETC) activity (Parnetti etal., *Neurosci. Lett.* 199:231–33, 1995).

Signs of oxidative injury are prominent features of AD pathology and, as noted above, reactive oxygen species (ROS) are critical mediators of neuronal degeneration. Indeed, studies at autopsy show that markers of protein, DNA and lipid peroxidation are increased in AD brain (Palmer et al., Brain Res. 645:338–42, 1994; Pappolla et al., Am. J. Pathol. 140:621–28, 1992; Jeandel et al., Gerontol. 35:275–82, 1989; Balazs et al., Arch. Neurol. 4:864, 1994; Mecocci et al., Ann. Neurol. 36:747–51, 1994; Smith et al., Proc. Nat. Acad. Sci. USA 88:10540–43, 1991). In hippocampal tissue from AD but not from controls, carbonyl formation indicative of protein oxidation is increased in neuronal cytoplasm, and nuclei of neurons and glia (Smith et al.,*Nature* 382:120–21, 1996). Neurofibrillary tangles also appear to be prominent sites of protein oxidation (Schweers et al., *Proc. Nat. Acad. Sci. USA* 92:8463, 1995; Blass et al., *Arch. Neurol.* 4:864, 1990). Under stressed and non-stressed conditions incubation of cortical tissue from AD brains taken at autopsy demonstrate increased free radical production relative to non-AD controls. In addition, the activities of critical antioxidant enzymes, particularly catalase, are reduced in AD (Gsell et al., *J. Neurochem.* 64:1216–23, 1995), suggesting that the AD brain is vulnerable to increased ROS production. Thus, oxidative stress may contribute significantly to the pathology of mitochondria associated diseases such as AD, where mitochondrial dysfunction and/or elevated ROS may be present.

One hallmark pathology of AD is the death of selected neuronal populations in discrete regions of the brain. Cell death in AD is presumed to be apoptotic because signs of programmed cell death (PCD) are seen and indicators of active gliosis and necrosis are not found. (Smale et al., *Exp. Neurolog.* 133:225–230, 1995; Cotman et al., *Molec. Neurobiol.* 10:19–45, 1995.) The consequences of cell death in AD, neuronal and synaptic loss, are closely associated with the clinical diagnosis of AD and are highly correlated with the degree of dementia in AD (DeKosky et al., *Ann. Neurology* 27:457–464, 1990).

Mitochondrial dysfunction is thought to be critical in the cascade of events leading to apoptosis in various cell types (Kroemer et al., *FASEB J.* 9:1277–87, 1995), and may be a cause of apoptotic cell death in neurons of the AD brain. Altered mitochondrial physiology may be among the earliest events in PCD (Zamzami et al., *J. Exp. Med.* 182:367–77, 1995; Zamzami et al., *J. Exp. Med.* 181:1661–72, 1995) and elevated reactive oxygen species (ROS) levels that result from such altered mitochondrial function may initiate the apoptotic cascade (Ausserer et al., *Mol. Cell. Biol.* 14:5032–42, 1994). In several cell types, including neurons, reduction in the mitochondrial membrane potential ($\Delta\Psi m$) precedes the nuclear DNA degradation that accompanies apoptosis. In cell-free systems, mitochondrial, but not nuclear, enriched fractions are capable of inducing nuclear apoptosis (Newmeyer et al., *Cell* 70:353–64, 1994). Perturbation of mitochondrial respiratory activity leading to altered cellular metabolic states, such as elevated intracellular ROS, may occur in mitochondria associated diseases and may further induce pathogenetic events via apoptotic mechanisms.

Oxidatively stressed mitochondria may release a preformed soluble factor that can induce chromosomal condensation, an event preceding apoptosis (Marchetti et al., *Cancer Res.* 56:2033–38, 1996). In addition, members of the Bcl-2 family of anti-apoptosis gene products are located within the outer mitochondrial membrane (Monaghan et al., *J. Histochem. Cytochem.* 40:1819–25, 1992) and these proteins appear to protect membranes from oxidative stress (Korsmeyer et al, *Biochim. Biophys. Act.* 1271:63, 1995). Localization of Bcl-2 to this membrane appears to be indispensable for modulation of apoptosis (Nguyen et al., *J. Biol. Chem.* 269:16521–24, 1994). Thus, changes in mitochondrial physiology may be important mediators of apoptosis. To the extent that apoptotic cell death is a prominent feature of neuronal loss in AD, mitochondrial dysfunction may be critical to the progression of this disease and may also be a contributing factor in other mitochondria associated diseases.

Regardless of whether a defect underlying a disease associated with altered mitochondrial function may have mitochondrial or extramitochondrial origins, and regardless of whether a defect underlying altered mitochondrial function has been identified, the present invention provides methods that are useful for determining the risk or presence of diseases associated with such altered mitochondrial function, and for identifying agents that are suitable for treating such diseases. In particular, as is elaborated herein below, the present invention provides compositions and methods for the detection of diseases associated with altered mitochondrial function by quantification of unusual mtDNA-like sequences not found in mitochondria and referred to as extramitochondrial DNA (exmtDNA), and other related advantages.

SUMMARY OF THE INVENTION

Briefly stated, the present invention is directed to compositions and methods useful for detecting mitochondria associated diseases and involving extramitochondrial DNA (exmtDNA) sequences that are highly homologous to mitochondrial DNA (mtDNA). In one aspect the invention provides a method for determining the risk for or presence of a disease associated with altered mitochondrial function in a first subject suspected of having or being at risk for having such a disease, by comparing a ratio r for each of a first and a second biological sample containing extramitochondrial DNA and mitochondrial DNA, the first biological sample being obtained from the first subject and the second sample being obtained from a second subject known to be free of a risk or presence of a disease associated with altered mitochondrial function, using the formula:

$$r = x/(x+y)$$

wherein x is the amount of extramitochondrial DNA in a sample, and y is the amount of mitochondrial DNA in the sample; and therefrom determining the risk or presence of the disease. In an embodiment of the invention, the ratio r is calculated by a method that comprises contacting a biological sample containing extramitochondrial DNA and mitochondrial DNA with an oligonucleotide primer having a nucleotide sequence that is complementary to a sequence present in the extramitochondrial DNA and present in the mitochondrial DNA, under conditions and for a time sufficient to allow hybridization of the primer to the extramitochondrial DNA and to the mitochondrial DNA; and detecting hybridization of the primer to the extramitochondrial DNA and to the mitochondrial DNA, in order to therefrom quantify the extramitochondrial DNA and the mitochondrial DNA.

In another embodiment, the ratio r is calculated by a method comprising contacting a sample containing amplified extramitochondrial DNA and-mitochondrial DNA with an oligonucleotide primer having a nucleotide sequence that is complementary to a sequence present in the amplified extramitochondrial DNA and present in the amplified mitochondrial DNA, under conditions and for a time sufficient to allow hybridization of the primer to the extramitochondrial DNA and to the mitochondrial DNA; and detecting hybridization of the primer to the extramitochondrial DNA and to the mitochondrial DNA, and therefrom quantifying the extramitochondrial DNA and the mitochondrial DNA. In another embodiment of this aspect of the invention the ratio r is calculated by a method comprising contacting a biological sample containing extramitochondrial DNA and mitochondrial DNA with an oligonucleotide primer having a nucleotide sequence that is complementary to a sequence present in the extramitochondrial DNA and present in the mitochondrial DNA, under conditions and for a time sufficient to allow hybridization of said primer to the extramitochondrial DNA and to the mitochondrial DNA; and detecting hybridization and extension of the primer to the extramitochondrial DNA to produce a first product and hybridization and extension of the primer to the mitochondrial DNA to produce a second product distinguishable from the first product, and therefrom quantifying the extramitochondrial DNA and the mitochondrial DNA.

In another embodiment of this aspect of the invention the ratio r is calculated by a method comprising contacting a sample containing amplified extramitochondrial DNA and mitochondrial DNA with an oligonucleotide primer having a nucleotide sequence that is complementary to a sequence present in the amplified extramitochondrial DNA and present in the amplified mitochondrial DNA, under conditions and for a time sufficient to allow hybridization of the primer to the extramitochondrial DNA and to the mitochondrial DNA; and detecting hybridization and extension of the primer to the extramitochondrial DNA to produce a first product and hybridization and extension of the primer to the mitochondrial DNA to produce a second product distinguishable from the first product, and therefrom quantifying the extramitochondrial DNA and the mitochondrial DNA.

In another embodiment of this aspect of the invention the biological sample is treated by heating it in water to lyse cells contained in the sample, and then extracting cellular DNA from the lysed cells using an aqueous DNA extraction procedure. In certain embodiments of the invention the sample comprises a crude buffy coat fraction of whole blood. In certain other embodiments of the invention, the method further comprises the step of determining the ApoE genotype of the first subject and correlating said genotype with the risk or presence of disease. In some embodiments of the invention, the disease associated with altered mitochondrial function may be Alzheimer's Disease, Huntington's Disease, Parkinson's Disease, dystonia, schizophrenia, non-insulin dependent diabetes mellitus, mitochondrial encephalopathy, lactic acidosis, and stroke, myoclonic epilepsy ragged red fiber syndrome, and Leber's hereditary optic neuropathy.

Another aspect of the invention provides a method for quantifying extramitochondrial DNA, comprising: contacting a sample containing extramitochondrial DNA with an oligonucleotide primer having a nucleotide sequence complementary to at least a portion of the extramitochondrial DNA under conditions and for a time sufficient to allow hybridization of the primer to the extramitochondrial DNA; and detecting hybridization of the primer to the extramitochondrial DNA, and therefrom quantifying the extramitochondrial DNA.

It is another aspect of the invention to provide a method for quantifying extramitochondrial DNA, comprising: contacting a sample containing extramitochondrial DNA with an oligonucleotide primer having a nucleotide sequence complementary to at least a portion of the extramitochondrial DNA under conditions and for a time sufficient to allow hybridization of the primer to the extramitochondrial DNA; and detecting hybridization and extension of the primer to the extramitochondrial DNA to produce a product, and therefrom quantifying the extramitochondrial DNA.

Another aspect of the invention provides a method for quantifying extramitochondrial DNA, comprising: contacting a sample containing amplified extramitochondrial DNA with an oligonucleotide primer having a nucleotide sequence complementary to at least a portion of the extramitochondrial DNA under conditions and for a time sufficient to allow hybridization of the primer to the extramitochondrial DNA; and detecting hybridization of the primer to the extramitochondrial DNA, therefrom quantifying the extramitochondrial DNA.

In yet another aspect of the invention, a method is provided for quantifying extramitochondrial DNA by contacting a sample containing amplified extramitochondrial DNA with an oligonucleotide primer having a nucleotide sequence complementary to at least a portion of the extramitochondrial DNA under conditions and for a time sufficient to allow hybridization of the primer to the extramitochondrial DNA; and detecting hybridization and extension of the primer to the extramitochondrial DNA to produce a product, and therefrom quantifying the extramitochondrial DNA.

In one embodiment the extramitochondrial DNA is amplified by polymerase chain reaction, transcriptional amplification systems or self-sustained sequence replication. In certain embodiments of the various aspects of the invention, a single oligonucleotide primer is used. In certain embodiments of the invention a primer extension assay is used. In certain embodiments of the invention, the step of detecting may be by polymerase chain reaction, primer extension assay, ligase chain reaction or restriction fragment length polymorphism analysis.

In certain embodiments of the invention, the amount of extramitochondrial DNA in a biological sample is quantified by determining the presence in the sample of a nucleotide sequence that may be SEQ ID NO: 1, a portion of SEQ ID NO:1, SEQ ID NO:3, a portion of SEQ ID NO:3, an extramitochondrial DNA sequence comprising a nucleic acid sequence that (i) corresponds to at least a portion of SEQ ID NO:2 and (ii) contains at least one nucleotide substitution of FIG. 4 at a corresponding nucleotide position, or an extramitochondrial DNA sequence comprising a nucleic acid sequence that (i) corresponds to at least a portion of SEQ ID NO:2 and (ii) contains at least one nucleotide deletion of FIG. 4 at a corresponding nucleotide position. In one embodiment the portion of the nucleotide sequence of SEQ ID NO:1 corresponds to a portion of the nucleotide sequence of SEQ ID NO:2 encoding a mitochondrial cytochrome c oxidase. In another embodiment the portion of SEQ ID NO:1 corresponds to a portion of a mitochondrial cytochrome c oxidase encoding sequence that may be portion of a cytochrome c oxidase 1 (CO1) encoding sequence or a portion of a cytochrome c oxidase 2 (CO2) encoding sequence. In still other embodiments, the portion of the nucleotide sequence of SEQ ID NO:1 corresponds to a portion of the nucleotide sequence of SEQ ID NO:2 encoding a mitochondrial ATP synthetase subunit. In other embodiments, the portion of SEQ ID NO:1 corresponds to a portion of a mitochondrial ATP synthetase subunit encoding sequence that may be a portion of a sequence encoding ATP synthetase subunit 6 or a portion of a sequence encoding ATP synthetase subunit 8.

In some embodiments the nucleotide sequence of SEQ ID NO:1 corresponds to a portion of SEQ ID NO:2 that may be a portion of a sequence encoding ND1, a sequence encoding a portion of ND2 or a sequence encoding a portion of CO3. In other embodiments, the portion of the nucleotide sequence of SEQ ID NO:3 corresponds to a portion of the nucleotide sequence of SEQ ID NO:2 encoding a mitochondrial ATP synthetase subunit, which in some embodiments may further be a portion of a sequence encoding ATP synthetase subunit 6 or a portion of a sequence encoding ATP synthetase subunit 8. In still other embodiments, the nucleotide sequence of SEQ ID NO:1 corresponds to a portion of the nucleotide sequence of SEQ ID NO:2 encoding a mitochondrial tRNA, while in yet other embodiments the portion of the nucleotide sequence of SEQ ID NO:3 corresponds to a portion of the nucleotide sequence of SEQ ID NO:2 encoding a mitochondrial tRNA.

In another aspect the invention provides an isolated nucleic acid comprising all or a portion of the nucleotide sequence of SEQ ID NO:1 or a complementary sequence thereto. In another aspect the invention provides an isolated nucleic acid comprising all or a portion of a nucleotide sequence of SEQ ID NO:1 or a complementary sequence thereto, wherein the sequence of the isolated nucleic acid differs by at least one nucleotide from the corresponding sequence of a nucleic acid comprising the nucleotide sequence of SEQ ID NO:2 or a complementary sequence thereto. In another aspect the invention provides an isolated nucleic acid comprising all or a portion of the nucleotide sequence of SEQ ID NO:3 or a complementary sequence thereto. In another aspect the invention provides an isolated nucleic acid comprising all or a portion of a nucleotide sequence of SEQ ID NO:3 or a complementary sequence thereto, wherein the sequence of the isolated nucleic acid differs by at least one nucleotide from the corresponding sequence of a nucleic acid comprising the nucleotide sequence of SEQ ID NO:2 or a complementary sequence thereto.

In another aspect the invention provides a method for determining the risk or presence of a disease associated with altered mitochondrial function in a subject suspected of having or being at risk for having such a disease, by quantifying the amount of extramitochondrial DNA and the amount of mitochondrial DNA in a biological sample from the subject, and therefrom determining the risk or presence of the disease. It is another aspect of the invention to provide a method for determining the risk or presence of a disease associated with altered mitochondrial function in a first subject suspected of having or being at risk for having such a disease, by comparing the amount of extramitochondrial DNA and the amount of mitochondrial DNA in a biological sample from the first subject to the amount of extramitochondrial DNA and the amount of mitochondrial DNA in a biological sample from a second subject, and therefrom determining the risk or presence of the disease. In another aspect the invention provides a method for determining the risk or presence of a disease associated with altered mitochondrial function in a first subject suspected of having or being at risk for having such a disease, by quantifying the amount of extramitochondrial DNA and the amount of mitochondrial DNA in a biological sample from the subject and comparing the amount of extramitochondrial DNA and the amount of mitochondrial DNA to the amount of extramitochondrial DNA and the amount of mitochondrial DNA in a biological sample from a second subject known to be free of a risk or presence of a disease associated with altered mitochondrial function, and therefrom determining the risk or presence of the disease.

Another aspect of the invention provides a method of regulating a telomere by administering to a subject a nucleic acid molecule comprising all or a portion of SEQ ID NO:1 or a complementary portion thereto. In one embodiment, the administered nucleic acid molecule comprises an exmtDNA sequence. In another aspect, the invention provides a method of regulating a telomere by administering to a subject a nucleic acid molecule comprising all or a portion of SEQ ID NO:3 or a complementary portion thereto.

Turning to another aspect, the invention provides a method of identifying an agent suitable for treating a disease associated with altered mitochondrial function, by comparing a ratio r from a sample obtained before contacting a biological source with a candidate agent to the ratio r from a sample obtained after contacting the biological source with the candidate agent, said ratio r calculated using the formula:

$$r=x/(x+y)$$

wherein x is the amount of extramitochondrial DNA in a sample, and y is the amount of mitochondrial DNA in the sample; and therefrom determining the suitability of said candidate agent for treating a disease associated with altered mitochondrial function. In one embodiment, the biological sample may be a crude buffy coat fraction of whole blood. In another embodiment, the biological sample is treated by heating in water to lyse cells contained in the sample, and then extracting cellular DNA from lysed cells using an aqueous DNA extraction procedure. In another embodiment, the ratio r is calculated by contacting a sample containing extramitochondrial DNA and mitochondrial DNA with an oligonucleotide primer having a nucleotide sequence that is complementary to a sequence present in the extramitochondrial DNA and present in the mitochondrial DNA, under conditions and for a time sufficient to allow hybridization of the primer to the extramitochondrial DNA and to the mitochondrial DNA; and detecting hybridization of the primer to the extramitochondrial DNA and to the mitochondrial DNA, and therefrom quantifying the extramitochondrial DNA and the mitochondrial DNA to calculate the ratio r.

In another embodiment of the invention, the ratio r is calculated by contacting a sample containing extramitochondrial DNA and mitochondrial DNA with an oligonucleotide primer having a nucleotide sequence that is complementary to a sequence present in the extramitochondrial DNA and present in the mitochondrial DNA, under conditions and for a time sufficient to allow hybridization of the primer to the extramitochondrial DNA and to the mitochondrial DNA; and detecting hybridization and extension of the primer to the extramitochondrial DNA to produce a first product and hybridization and extension of the primer to the mitochondrial DNA to produce a second product distinguishable from the first product, and therefrom quantifying the extramitochondrial DNA and the mitochondrial DNA to calculate the ratio. In another embodiment, the ratio r is calculated by contacting a sample containing amplified extramitochondrial DNA and mitochondrial DNA with an oligonucleotide primer having a nucleotide sequence that is complementary to a sequence present in said amplified extramitochondrial DNA and present in said amplified mitochondrial DNA, under conditions and for a time sufficient to allow hybridization of said primer to the extramitochondrial DNA and to the mitochondrial DNA; and detecting hybridization of the primer to the extramitochondrial DNA and to the mitochondrial DNA, and therefrom quantifying the extramitochondrial DNA and the mitochondrial DNA to calculate the ratio r.

In yet another embodiment, the ratio r is calculated by contacting a sample containing amplified extramitochondrial DNA and mitochondrial DNA with an oligonucleotide primer having a nucleotide sequence that is complementary to a sequence present in the amplified extramitochondrial DNA and present in the amplified mitochondrial DNA, under conditions and for a time sufficient to allow hybridization of said primer to the extramitochondrial DNA and to the mitochondrial DNA; and detecting hybridization and extension of the primer to the extramitochondrial DNA to produce a first product and hybridization and extension of the primer to the mitochondrial DNA to produce a second product distinguishable from said first product, and therefrom quantifying the extramitochondrial DNA and the mitochondrial DNA to calculate the ratio.

In another embodiment of the invention, comparing the ratio r from a sample obtained before contacting a biological source with a candidate agent to the ratio from a sample obtained after contacting the biological source with the candidate agent comprises determination of the presence in the sample of a nucleotide sequence of SEQ ID NO:1 or portion thereof, or a nucleotide sequence of SEQ ID NO:3 or a portion thereof, or an extramitochondrial DNA sequence comprising a nucleic acid sequence that (i) corresponds to at least a portion of SEQ ID NO:2 and (ii) contains at least one nucleotide substitution of FIG. 4 at a corresponding nucleotide position, or an extramitochondrial DNA sequence comprising a nucleic acid sequence that (i) corresponds to at least a portion of SEQ ID NO:2 and (ii) contains at least one nucleotide deletion of FIG. 4 at a corresponding nucleotide position. In another embodiment, the nucleotide sequence of SEQ ID NO:1 or a portion thereof corresponds to a mitochondrial cytochrome c oxidase encoding sequence of SEQ ID NO:2 or a portion thereof. In another embodiment, the mitochondrial cytochrome c oxidase encoding sequence of SEQ ID NO:2 or a portion thereof is a sequence encoding CO1 or a portion thereof, or a sequence encoding CO2 or a portion thereof. In another embodiment, the nucleotide sequence of SEQ ID NO:1 or portion thereof, or the nucleotide sequence of SEQ ID NO:3 or portion thereof corresponds to a mitochondrial ATP synthetase subunit encoding sequence of SEQ ID NO:2 or a portion thereof. In another embodiment, the mitochondrial ATP synthetase subunit encoding sequence of SEQ ID NO:2 or a portion thereof may be a sequence encoding ATP synthetase subunit 6 or a portion thereof, or a sequence encoding ATP synthetase subunit 8 or a portion thereof. In another embodiment, the nucleotide sequence of SEQ ID NO:1 corresponds to a sequence of SEQ ID NO:2 or a portion thereof that may be a sequence encoding a truncated NADH dehydrogenase subunit 1 or a portion thereof, a sequence encoding NADH dehydrogenase subunit 2 or a portion thereof or a sequence encoding truncated CO3 or a portion thereof.

In other embodiments of the invention, the disease associated with altered mitochondrial function may be Alzheimer's Disease, Huntington's Disease, Parkinson's Disease, dystonia, schizophrenia, non-insulin dependent diabetes mellitus, mitochondrial encephalopathy, lactic acidosis, and stroke, myoclonic epilepsy ragged red fiber syndrome, or Leber's hereditary optic neuropathy.

In another aspect, the invention provides a method of identifying an agent suitable for treating a subject suspected of being at risk for having a disease associated with altered mitochondrial function, by determining the apolipoprotein E genotype of the subject; comparing a ratio r in a biological sample obtained from the subject before contacting the sample with a candidate agent to the ratio r in a biological sample obtained from the subject after contacting the sample with a candidate agent, the ratio r calculated using the formula:

$$r=x/(x+y)$$

wherein x is the amount of extramitochondrial DNA in the sample, and y is the amount of mitochondrial DNA in the sample; and therefrom determining the suitability of said candidate agent for treating the disease associated with altered mitochondrial function. In another embodiment, the disease associated with altered mitochondrial function is Alzheimer's disease.

It is another aspect of the invention to provide a method of correlating a ratio r with the suitability of an agent for treating Alzheimer's disease in a subject, by determining a ratio r in a biological sample obtained from the subject, said ratio r calculated using the formula:

$$r=x/(x+y)$$

wherein x is the amount of extramitochondrial DNA in the sample, and y is the amount of mitochondrial DNA in the sample; contacting said subject with a candidate agent and evaluating the subject for alterations in the AD disease state, and therefrom correlating the suitability of the agent for treating AD in the subject with r. In another embodiment, the apolipoprotein E genotype of the subject is determined, and therefrom the suitability of the agent for treating AD in the subject is correlated with r and with the apolipoprotein E genotype.

These and other aspects of the present invention will become evident upon reference to the following detailed description and attached drawings. In addition, various references are set forth herein which describe in more detail certain aspects of this invention, and are therefore incorporated by reference in their entirety.

BRIEF DESCRIPTION OF THE DRAWINGS

FIG. 1 depicts the nucleotide sequence of SEQ ID NO:1.
FIG. 2 depicts the nucleotide sequence of SEQ ID NO:2.
FIG. 3 depicts the nucleotide sequence of SEQ ID NO:3.
FIG. 4 depicts human extramitochondrial DNA nucleotide substitutions and deletions relative to the corresponding human mtDNA sequence of SEQ ID NO:2.

DETAILED DESCRIPTION OF THE INVENTION

The present invention is directed generally to compositions and methods for diagnosing the risk or presence of a disease associated with altered mitochondrial function in a subject, and to compositions and methods for the identification of agents that may be suitable for treating a disease associated with altered mitochondrial function. The invention utilizes a ratio, r, that may be useful for pharmacogenomic purposes, for example to stratify patient populations according to the suitability of particular therapeutic agents for use in such populations. The ratio r is the ratio of the amount of exmtDNA in a biological sample relative to the sum of the amount of exmtDNA plus mtDNA in the sample. As expressed quantitatively, the ratio r may be calculated using the formula:

$$r=x/(x+y)$$

wherein
x is the amount of exmtDNA in a sample, and
y is the amount of mtDNA in the sample.

In various aspects of the invention, as elaborated more fully herein, quantification of x and y provide, through calculation of r, parameters useful in diagnosis of a disease associated with altered mitochondrial function and in screening assays for agents that may be suitable for the treatment of such a disease.

As discussed above, "altered mitochondrial function" may refer to any condition or state, including those that accompany a disease, where any structure or activity that is directly or indirectly related to a mitochondrial function has been changed. Altered mitochondrial function may have its origin in extramitochondrial structures or events as well as in mitochondrial structures or events, in direct interactions between mitochondrial and extramitochondrial genes and/or their gene products, or in structural or functional changes that occur as the result of interactions between intermediates that may be formed as the result of such interactions, including metabolites, catabolites, substrates, precursors, cofactors and the like.

Also as discussed above, altered mitochondrial function may include (but need not be limited to) altered respiratory or metabolic activity in some or all cells of a biological source. For example, markedly impaired ETC activity may be an example of altered mitochondrial function, as may be generation of increased ROS or defective oxidative phosphorylation. As further examples, altered mitochondrial membrane potential, induction of apoptotic pathways and formation of atypical chemical and biochemical crosslinked species within a cell, whether by enzymatic or non-enzymatic mechanisms, may all be regarded as indicative of altered mitochondrial function. Without wishing to be bound by theory, alterations in the ratio r are believed to reflect chemical changes within affected cells that quantitatively influence recoveries of exmtDNA and/or mtDNA. For example, biochemical crosslinking events may result in the formation of DNA aggregates, DNA adducts or other molecular species that affect DNA recoveries following extraction procedures.

According to the present invention, alterations in the ratio r as defined above provide a novel and useful parameter for diagnosing the risk or presence of a disease associated with altered mitochondrial function in a subject, and for identifying agents that may be suitable for treating a disease associated with altered mitochondrial function. As discussed above, a number of diseases, including several degenerative diseases, are associated with alterations in mitochondrial function. Further, detection of an appropriate parameter of altered mitochondrial function can provide preclinical evidence for a risk of or predisposition to a disease.

Determination of the ratio r involves quantification of exmtDNA (x) and mtDNA (y) that may be based on strong but not necessarily absolute nucleotide sequence conservation when corresponding portions of mtDNA and exmtDNA are compared, as discussed herein. In most preferred embodiments of the invention, determination of r is accomplished by detecting minor nucleotide sequence differences in highly conserved mtDNA and exmtDNA regions, as elaborated below. The invention provides compositions and methods that include the use of nucleic acid molecules, or portions thereof, having nucleotide sequences that are found in the human mtDNA sequence SEQ ID NO:2 (Anderson et al., Nature 290:457, 1981) and fragments of SEQ ID NO:2 that are suitable for use as oligonucleotide primers in nucleic acid primer extension or amplification techniques, as hybridization probes for the detection of complementary nucleotide sequences in a sample or for any number of additional uses that are well known to those familiar with the art. ExmtDNA may be nuclear DNA, including chromosomal and non-chromosomal DNA, or non-nuclear extramitochondrial DNA that may be from any subcellular compartment, provided it is not mtDNA.

Nucleic acid sequences within the scope of the invention include isolated DNA and RNA sequences that specifically hybridize under conditions of moderate or high stringency to exmtDNA nucleotide sequences, including exmtDNA sequences disclosed herein or fragments thereof, and their complements. As used herein, conditions of moderate stringency, as known to those having ordinary skill in the art, and as defined by Sambrook et al., *Molecular Cloning: A Laboratory Manual*, 2nd Ed. Vol. 1, pp. 1.101–1.104, Cold Spring Harbor Laboratory Press (1989), include use of a prewashing solution for the nitrocellulose filters 5×SSC, 0.5% SDS, 1.0 mM EDTA (pH 8.0), hybridization conditions of 50% formamide, 6×SSC at 42° C. (or other similar hybridization solution), and washing conditions of about 50–60° C., 0.5×SSC, 0.1% SDS. Conditions of high stringency are defined as hybridization conditions as above, and with washing at 60–68° C., 0.2×SSC, 0.1% SDS. In other embodiments, hybridization to an exmtDNA nucleotide sequence may be at normal stringency, which is approximately 25–30° C. below Tm of the native duplex (e.g., 5×SSPE, 0.5% SDS, 5×Denhardt's solution, 50% formamide, at 42° C. or equivalent conditions), at low stringency hybridizations, which utilize conditions approximately 40° C. below Tm, or at high stringency hybridizations, which utilize conditions approximately 10° C. below Tm. The skilled artisan will recognize that the temperature, salt concentration; and chaotrope composition of hybridization and wash solutions may be adjusted as necessary according to factors such as the length and nucleotide base composition of the probe. (See also, e.g., Ausubel et al., *Current Protocols in Molecular Biology*, Greene Publishing, 1987.)

An "isolated nucleic acid molecule" refers to a polynucleotide molecule in the form of a separate fragment or as a component of a larger nucleic acid construct, that has been separated from its source cell (including the chromosome it normally resides in) at least once, preferably in a substantially pure form. Isolated nucleic acids may be nucleic acids having particular disclosed nucleotide sequences or may be regions, portions or fragments thereof. Those having ordinary skill in the art are able to prepare isolated nucleic acids having the complete nucleotide sequence, or the sequence of any portion of a particular isolated nucleic acid molecule, when provided with the appropriate nucleic acid sequence information as disclosed herein. Nucleic acid molecules may be comprised of a wide variety of nucleotides, including DNA, RNA, nucleotide analogues such as phosphorothioates or peptide nucleic acids, or other analogues with which those skilled in the art will be familiar, or some combination of these.

The present invention, as described herein, provides exmtDNA sequences and isolated exmtDNA nucleic acid molecules. exmtDNA may be isolated from genomic DNA, typically by first generating an appropriate DNA library through techniques for constructing libraries that are known in the art (see Sambrook et al., *Molecular Cloning: A Laboratory Manual*, Cold Spring Harbor Press, 1989) or purchased from commercial sources (e.g., Clontech, Palo Alto, Calif.). Briefly, genomic DNA libraries can be constructed in chromosomal vectors, such as YACs (yeast artificial chromosomes), bacteriophage vectors, such as pBeloBAC11, λEMBL3, λgt10, cosmids, or plasmids. Alternatively, isolated exmtDNA may be prepared by preferentially amplifying exmtDNA sequences present in biological samples using, for example, DNA amplification methodologies such as PCR or other amplification techniques that are well known in the art, with suitable oligonucleotide primers complementary to exmtDNA sequences as disclosed herein.

In one embodiment, known mtDNA sequences derived from SEQ ID NO:2 (Anderson et al., *Nature* 290:457, 1981) may be utilized to design oligonucleotide hybridization probes suitable for screening genomic libraries. Preferably, such oligonucleotide probes are 18–30 bases in length and have sequences that, under the hybridization conditions selected, hybridize to complementary exmtDNA sequences lacking nucleotide substitutions, insertions or deletions ("mutations") relative to the corresponding region of the mtDNA sequence of SEQ ID NO:2.

Portions of an exmtDNA sequence and the mtDNA sequence of SEQ ID NO:2 are regarded as "corresponding" nucleic acid sequences, regions, fragments or the like, based on the convention for numbering mtDNA nucleic acid positions according to SEQ ID NO:2 (Anderson et al., *Nature* 290:457, 1981), wherein an exmtDNA sequence is aligned with the mtDNA sequence of SEQ ID NO:2 such that at least 70%, preferably at least 80% and more preferably at least 90% of the nucleotides in a given sequence of at least 20 consecutive nucleotides of a sequence are identical. In certain preferred embodiments, an exmtDNA sequence is greater than 95% identical to a corresponding mtDNA sequence. In certain particularly preferred embodiments, an exmtDNA sequence is identical to a corresponding mtDNA sequence. Those oligonucleotide probes having sequences that are identical in corresponding regions of mtDNA and exmtDNA may be identified and selected following hybridization target DNA sequence analysis, to verify the absence of mutations in the target exmtDNA sequence relative to the primer mtDNA-derived sequence.

To facilitate hybridization detection, the oligonucleotide may be conveniently labeled, generally at the 5' end, with a reporter molecule, such as a radionuclide, e.g., $^{32}P$, enzymatic label protein label, fluorescent label, biotin or other suitable labeling moieties known in the art. Such libraries are then generally plated as phage or colonies, depending upon the vector used. Subsequently, a plate replica to which the colonies or phage have been transferred, such as a nitrocellulose or nylon membrane or the like, is probed to identify candidate clones that contain the exmtDNA sequence. Such candidates may be verified as containing exmtDNA by any of various means including, for example, DNA sequence analysis or hybridization with a second, non-overlapping probe selected as described above to hybridize with target exmtDNA sequences lacking nucleotide substitutions, deletions or insertions relative to the corresponding portion of the mtDNA sequence of SEQ ID NO:2.

Once a library is identified as containing exmtDNA, the exmtDNA can be isolated by amplification. Briefly, when using genomic library DNA as a template, amplification primers are designed based upon known mtDNA sequences (SEQ ID NO:2) and primer "walking" is used to select primers that anneal to exmtDNA regions that are identical to mtDNA sequences. The primers preferably have a GC content of about 50% and contain restriction sites to facilitate cloning. Primers do not have self-complementary sequences, nor do they contain complementary sequences at their 3' end (to prevent primer-dimer formation). The primers are annealed to genomic DNA and sufficient amplification cycles are performed to yield a product readily visualized by gel electrophoresis and staining. The amplified fragment is purified and inserted into a vector, such as λgt10 or pBS(M13+), and propagated. Confirmation of the nature of the fragment is obtained by DNA sequence analysis.

As an example of detection of mtDNA-like sequences in a DNA library, an oligonucleotide having a nucleotide sequence present in a portion of any human mtDNA gene, preferably one of the human mtDNA encoded genes NADH dehydrogenase subunit 1 (ND1), NADH dehydrogenase subunit 2 (ND2), NADH dehydrogenase subunit 3 (ND3), NADH dehydrogenase subunit 4 (ND4), NADH dehydrogenase subunit 4L (ND4L), NADH dehydrogenase subunit 5 (ND5), NADH dehydrogenase subunit 6 (ND6), $tRNA^{Lys}$, $tRNA^{Ile}$, $tRNA^{Gln}$, $tRNA^{Met}$, $tRNA^{Cys}$, $tRNA^{Tyr}$, $tRNA^{Asp}$ or cytochrome c oxidase 3 (CO3) and more preferably one of the human mtDNA encoded genes CO1, CO2, ATPase 8 or ATPase 6, may be labeled and used as a probe on a human genomic DNA library. An initial hybridization at normal stringency may yield candidate clones or fragments. If no hybridization is initially observed, varying degrees of stringency may be used. (See Sambrook et al., Ausubel et al., supra, and other well-known sources for stringency conditions.) Where it is advantageous to use oligonucleotide primers according to the present invention, such primers may be 10–60 nucleotides in length, preferably 15–35 nucleotides and still more preferably 18–30 nucleotides in length. Primers as described above for use in isolating exmtDNA from genomic DNA may also be useful in the present invention for quantifying mtDNA and exmtDNA by any of a variety of techniques well known in the art for determining the amount of specific nucleic acid target sequences present in a sample based on specific hybridization of a primer to the target sequence. Optionally, in certain of these techniques, hybridization precedes nucleotide polymerase catalyzed extension of the primer using the strand containing the target sequence as a template, and/or ligation of oligonucleotides hybridized to adjacent target sequences, and embodiments of the invention using primer extension are particularly preferred. For examples of references on such quantitative detection techniques, including those that may be used to detect nucleotide insertions, substitutions or deletions in a portion of an exmtDNA sequence site near an oligonucleotide primer target hybridization site that corresponds to a portion of the mtDNA sequence of SEQ ID NO:2, and further including those that involve primer extension, see U.S. Pat. No. 5,760,205 and the references cited therein, all of which are hereby incorporated by reference, and see also, for example, Botstein et al. (*Am. J. Hum. Gen.* 32:314, 1980), Gibbs et al. (*Nucl. Ac. Res.* 17:2437, 1989), Newton et al. (*Nucl. Ac. Res.* 17:2503, 1989), Grossman et al. (*Nucl. Ac. Res.* 22:4527, 1994), and Saiki et al. (*Proc. Nat. Acad. Sci.* 86:6230, 1989), all of which are hereby incorporated by reference. A particularly useful method for this purpose is the primer extension assay disclosed by Fahy et al. (*Nucl. Acids Res.* 25:3102. 1997) and by Ghosh et al. (*Am. J. Hum. Genet.* 58:325, 1996), both of which references are hereby incorporated in their entireties, as is Krook et al. (*Hum. Molec. Genet.* 1:391, 1995) which teaches modification of primer extension reactions to detect multiple nucleotide substitutions, insertions, deletions or other mutations. Other examples of useful techniques for quantifying the presence of specific nucleic acid target sequences in a sample include but need not be limited to labeled probe hybridization to the target nucleic acid sequences with or without first partially separating target nucleic acids from other nucleic acids present in the sample.

Examples of other useful techniques for determining the amount of specific nucleic acid target sequences present in a sample based on specific hybridization of a primer to the target sequence include specific amplification of target nucleic acid sequences and quantification of amplification products, including but not limited to polymerase chain reaction (PCR, Gibbs et al., *Nucl. Ac. Res.* 17:2437, 1989), transcriptional amplification systems, strand displacement amplification and self-sustained sequence replication (3SR, Ghosh et al, in Molecular Methods for Virus Detection, 1995 Academic Press, NY, pp. 287–314), the cited references for which are hereby incorporated in their entireties. Examples of other useful techniques include ligase chain reaction, single stranded conformational polymorphism analysis, Q-beta replicase assay, restriction fragment length polymorphism (RFLP, Botstein et al., *Am. J. Hum. Gen.* 32:314, 1980) analysis and cycled probe technology, as well as other suitable methods that will be known to those familiar with the art.

In a particularly preferred embodiment of the invention, primer extension is used to quantify exmtDNA and mtDNA present in a biological sample. (Ghosh et al., *Am. J. Hum. Genet.* 58:325, 1996) This embodiment may offer certain advantages by permitting both exmtDNA and mtDNA to be simultaneously quantified using a single oligonucleotide primer capable of hybridizing to a complementary nucleic acid target sequence that is present in a defined region of mtDNA and in a corresponding region of a exmtDNA sequence. Without wishing to be bound by theory, the use of a single primer for quantification of exmtDNA and of mtDNA is believed to avoid uncertainties associated with potential disparities in the relative hybridization properties of multiple primers and may offer other advantages. Where such a target sequence is situated adjacent to an exmtDNA nucleotide sequence position that is a nucleotide substitution, insertion or deletion relative to the corresponding mtDNA sequence position, primer extension assays may be designed such that oligonucleotide extension products of primers hybridizing to mtDNA are of different lengths than oligonucleotide extension products of primers hybridizing to exmtDNA. Accordingly, the amount of exmtDNA in a sample and the amount of mtDNA in the sample may be determined by quantification of distinct extension products that are separable on the basis of sequence length or molecular mass, for purposes of calculating the ratio r as described above.

Sequence length or molecular mass of primer extension assay products may be determined using any known method for characterizing the size of nucleic acid sequences with which those skilled in the art are familiar. In a preferred embodiment, primer extension products are characterized by gel electrophoresis. In another preferred embodiment, primer extension products are characterized by mass spectrometry (MS), which may further include matrix assisted laser desorption ionization/time of flight (MALDI-TOF) analysis or other MS techniques known to those having skill in the art. See, for example, U.S. Pat. Nos. 5,622,824, 5,605,798 and 5,547,835, all of which are hereby incorporated by reference in their entireties. In another preferred embodiment, primer extension products are characterized by liquid or gas chromatography, which may further include high performance liquid chromatography (HPLC), gas chromatography-mass spectrometry (GC-MS) or other well known chromatographic methodologies.

Any exmtDNA sequence or portion of an exmtDNA sequence that corresponds to the human mtDNA sequence of SEQ ID NO:2 or a portion thereof or several portions thereof may be useful in this embodiment of the invention. Examples of human exmtDNA sequences that are useful in this and other embodiments of the invention are disclosed in SEQ ID NO:1 in SEQ ID NO:3 and in SEQ ID NO:4. Nucleotide positions at which exmtDNA and mtDNA differ are provided in FIG. 4, in which are presented the identities of nucleotides at particular sequence positions in the human mtDNA genome (SEQ ID NO:2) and the corresponding positions in exmtDNA of SEQ ID NOS:1, 3 and 4, and in other specific exmtDNA regions corresponding to the human mtDNA encoded genes NADH dehydrogenase subunit 1 (ND1), NADH dehydrogenase subunit 2 (ND2), NADH dehydrogenase subunit 3 (ND3), NADH dehydrogenase subunit 4 (ND4), NADH dehydrogenase subunit 4L (ND4L), NADH dehydrogenase subunit 5 (ND5), NADH dehydrogenase subunit 6 (ND6), $tRNA^{Lys}$, $tRNA^{Ile}$, $tRNA^{Gln}$, $tRNA^{Met}$, $tRNA^{Cys}$, $tRNA^{Tyr}$, $tRNA^{Asp}$ or cytochrome c oxidase 3 (CO3). These exmtDNA nucleotide sequences that correspond to the human mtDNA sequence of SEQ ID NO:2 and that differ from SEQ ID NO:2 by the specific nucleotide substitution or deletion provided in FIG. 4 for an indicated nucleotide position number (using the numbering system of Anderson et al., 1981 Nature 290:457) were determined as provided herein by sequence analysis of SEQ ID NOS: 1, 3 or of SEQ ID NO:4 or of cloned PCR amplicons generated as described herein using oligonucleotide primer sets disclosed in Tables 1–3.

Portions of SEQ ID NO:2 that include nucleic acid sequences encoding the mitochondrial ETC enzymes cytochrome c oxidase 1 (CO 1), cytochrome c oxidase 2 (CO 2), ATP synthetase subunit 8 (ATPase 8) and ATP synthetase subunit 6 (ATPase 6) may be particularly useful, and in preferred embodiments of the invention these sequences comprise isolated nucleic acid molecules that have nucleotide sequences identical or complementary to corresponding nucleic acid sequences present in exmtDNA of SEQ ID NO:1 and/or SEQ ID NO:3 and/or SEQ ID NO:4. Portions of SEQ ID NO:2 that include nucleic acid sequences encoding the mitochondrial tRNAs, including mitochondrial isoleucyl, glutaminyl, methionyl, aspartyl, cysteinyl, tyrosinyl and lysyl tRNAs may also be particularly useful. Also particularly useful in preferred embodiments of the invention are sequences comprising isolated nucleic acid molecules that have nucleotide sequences identical or complementary to corresponding nucleic acid sequences present in exmtDNA of SEQ ID NO:1 and/or of SEQ ID NOS:3 and/or 4, and/or to corresponding regions of SEQ ID NO:2 having the specific nucleotide substitutions or deletions identified at the indicated corresponding mtDNA nucleotide position in FIG. 4, or any portion or fragment thereof.

FIG. 4 shows nucleotides present in human mtDNA of SEQ ID NO:2 (Anderson et al., 1981 Nature 290:457) at the indicated nucleotide position number, and also shows single base substitutions or deletions, which substitutions and deletions are provided by the instant invention., at the corresponding nucleotide position number in human exmtDNA sequences. The "gene" column refers to the mtDNA encoded gene region in which the indicated mtDNA nucleotide position numbers are present: "COI", "COII" and COIII" refer, respectively, to cytochrome c oxidase subunits I (COX I), II (COX II) and III (COX III); "ATPase" refers to ATP synthetase (also commonly referred to as ATP synthase); "ND" refers to NADH dehydrogenase (also known as NADH:ubiquinone oxidoreductase or mitochondrial electron transport chain Complex I); and genes encoding tRNA specific for the amino acid indicated by the well known three letter code are appropriately labeled.

The "fragment" column in FIG. 4 refers either (i) to cloned and sequenced exmtDNA containing the indicated nucleotide substitutions and deletions relative to the corresponding positions in human mtDNA, wherein "5.8 kb pg" refers to SEQ ID NO:1 and "519 bp pg" refers to SEQ ID NO:3; or alternatively, (ii) identifies oligonucleotide primer sets from Table 1 (COX I, II and III), Table 2 (ND 1–4, 4L, 5 and 6), or Table 3 (ATP synthetase subunits 8 and 6) that were used to PCR amplify cellular DNA as described herein, using a two-digit number with a letter code (A=alternate, i.e., an alternate primer complementary to an overlapping and/or adjacent region of human mtDNA [SEQ ID NO:2] relative to a first primer having the same two-digit number and orientation—such alternates are included to provide means for PCR amplifying a particular human exmtDNA region containing one or more substitutions or deletions listed in FIG. 4, where under certain conditions one member of the primer pair comprising the first primer and its alternate may be incapable of duplex formation with an exmtDNA target sequence due to an uncharacterized sequence variation, for example a mutation such as a point mutation, in the target sequence. Typically, an alternate primer will be designed to anneal to an exmtDNA target sequence that commences at a nucleotide corresponding to a nucleotide position in human mtDNA situated within 1–100 nucleotides of the position where the first primer anneals, preferably within 1–50 nucleotides, more preferably within 1–30 nucleotides and still more preferably within 1–15 nucleotides. F=forward orientation; R=reverse orientation.)

TABLE I

OLIGONUCLEOTIDE PRIMERS CORRESPONDING TO CYTOCHROME C OXIDASE ENCODING MTDNA SEQUENCES

| SEQ. ID. NO. | PRIMER | GENE | NUCLEOTIDE POSITION (5', light strand) | PRIMER SEQUENCE 5'→3' |
|---|---|---|---|---|
| 14 | 11F | CO I | 5864 | GTCCAATGCTTCACTCAGCCA |
| 15 | 11FA | CO I | 5859 | TTACAGTCCAATGCTTCACTC |
| 16 | 11R | CO I | 6177 | TATGCGGGGAAACGCCAT |
| 17 | 11RA | CO I | 6180 | TGTTTATGCGGGGAAACGC |
| 18 | 12F | CO I | 6138 | GGCAACTGACTAGTTCCCCTA |
| 19 | 12FA | CO I | 6125 | AATCGGAGGCTTTGGCAACTG |
| 20 | 12R | CO I | 6425 | GTTTGGTATTGGGTTATGGCA |
| 21 | 12RA | CO I | 6422 | TGGTATTGGGTTATGGCAGGG |
| 22 | 13F | CO I | 6383 | GGCCATCAATTTCATCACAA |
| 23 | 13FA | CO I | 6358 | TAGCAGGTGTCTCCTCTATCTT |
| 24 | 13R | CO I | 6697 | ATACCTATGTATCCAAATGGTTCTT |
| 25 | 13RA | CO I | 6699 | CCATACCTATGTATCCAAATGGTTC |
| 26 | 14F | CO I | 6657 | GGAATAATCTCCCATATTGTAACTT |
| 27 | 14R | CO I | 6945 | CAGGCCACCTACGGTGAA |
| 28 | 14RA | CO I | 6947 | GTCAGGCCACCTACGGTG |
| 29 | 15F | CO I | 6914 | AGTGCTCTGAGCCCTAGGAT |
| 30 | 15FA | CO I | 6902 | ATGATCTGCTGCAGTGCTCT |
| 31 | 15R | CO I | 7193 | ATTCCGGATAGGCCGAGA |
| 32 | 16F | CO I | 7159 | TCGGCGTAAATCTAACTTTCTT |
| 33 | 16R | CO I | 7451 | GGGGTTCGATTCCTTCCTT |
| 34 | 16RA | CO I | 7472 | TTGGCTTGAAACCAGCTTT |
| 35 | 21F | CO II | 7546 | TTGTCAAAGTTAAATTATAGGCTA |
| 36 | 21FA | CO II | 7548 | GTCAAAGTTAAATTATAGGCTAAA |
| 37 | 21R | CO II | 7832 | ACCTCGTCTGTTATGTAAAGGAT |
| 38 | 21RA | CO II | 7834 | TGACCTCGTCTGTTATGTAAAGG |
| 39 | 22F | CO II | 7792 | CGCCATCATCCTAGTCCTCA |
| 40 | 22R | CO II | 8050 | ATGAGTGCAAGACGTCTTGTGAT |
| 41 | 23F | CO II | 8003 | AATCGAGTAGTACTCCCGATTGA |
| 42 | 23FA | CO II | 8007 | GAGTAGTACTCCCGATTGAAGCC |
| 43 | 23R | CO II | 8286 | GTTAGCTTTACAGTGGGCTCTAGA |
| 44 | 23RA | CO II | 8287 | AGTTAGCTTTACAGTGGGCTCTAG |
| 45 | 31F | CO III | 9171 | ACTTCTAGTAAGCCTCTACCTGCA |
| 46 | 31FA | CO III | 9173 | TTCTAGTAAGCCTCTACCTGCACG |
| 47 | 31R | CO III | 9447 | AGGTAATAAATAGGATTATCCCGTA |
| 48 | 31RA | CO III | 9443 | AATAAATAGGATTATCCCGTATCGA |
| 49 | 32F | CO III | 9416 | CCACACACCACCTGTCCAA |
| 50 | 32FA | CO III | 9415 | ACCACACACCACCTGTCCA |
| 51 | 32R | CO III | 9741 | AAGGGAGACTCGAAGTACTCTGA |
| 52 | 33F | CO III | 9712 | TGGGTCTCTATTTTACCCTCCTA |
| 53 | 33FA | CO III | 9698 | TATTACAATTTTACTGGGTCTCT |
| 54 | 33R | CO III | 10010 | ACTAGTTAATTGGAAGTTAACGGTA |

TABLE 2

OLIGONUCLEOTIDE PRIMERS CORRESPONDING TO NADH DEHYDROGENASE ENCODING MTDNA SEQUENCES

| SEQ. ID. NO. | PRIMER | GENE | NUCLEOTIDE POSITION (5', light strand) | PRIMER LENGTH | PRIMER SEQUENCE 5'→3' |
|---|---|---|---|---|---|
| 55 | 61F | ND1 | 3281 | 23 | GAGGTTCAATTCCTCTTCTTAAC |
| 56 | 61R | ND1 | 3631 | 22 | TTGAGTAAACGGCTAGGCTAGA |
| 57 | 62F | ND1 | 3589 | 20 | CTGGTCAACCTCAACCTAGG |
| 58 | 62R | ND1 | 3946 | 16 | GGCCTGCGGCGTATTC |
| 59 | 63F | ND1 | 3908 | 17 | CCGAAGGGGAGTCCGAA |
| 60 | 63R | ND1 | 4270 | 25 | ATCAAAGTAACTCTTTTATCAGACA |
| 61 | 71F | ND2 | 4447 | 20 | TTGGTTATACCCTTCCCGTA |
| 62 | 71R | ND2 | 4769 | 26 | CTATTCCTAGTTTTATTGCTATAGCT |
| 63 | 72F | ND2 | 4699 | 22 | ACAATATACTCTCCGGACAATG |
| 64 | 72R | ND2 | 5054 | 23 | GAATGGTTATGTTAGGGTTGTAC |
| 65 | 73F | ND2 | 4990 | 22 | AGCTACGCAAAATCTTAGCATA |
| 66 | 73R | ND2 | 5311 | 19 | AGGGTGATGGTGGCTATGA |
| 67 | 74F | ND2 | 5234 | 15 | CCCGCTAACCGGCTT |
| 68 | 74R | ND2 | 5536 | 18 | AGGGCTTTGAAGGCTCTT |
| 69 | 81F | ND4L | 10433 | 25 | TTTCGACTCATTAAATTATGATAAT |
| 70 | 81R | ND4L | 10782 | 25 | CATGTCAGTGGTAGTAATATAATTG |
| 71 | 82F | ND4 | 10718 | 22 | CACATATGGCCTAGACTACGTA |

TABLE 2-continued

OLIGONUCLEOTIDE PRIMERS CORRESPONDING TO NADH DEHYDROGENASE ENCODING MTDNA SEQUENCES

| SEQ. ID. NO. | PRIMER | GENE | NUCLEOTIDE POSITION (5', light strand) | PRIMER LENGTH | PRIMER SEQUENCE 5'->3' |
|---|---|---|---|---|---|
| 72 | 82R | ND4 | 11060 | 23 | ATAATTAAGGAGATTTGTAGGGA |
| 73 | 83F | ND4 | 10999 | 19 | CCAACGCCACTTATCCAGT |
| 74 | 83R | ND4 | 11342 | 25 | AAGCTATTGTGTAAGCTAGTCATAT |
| 75 | 84F | ND4 | 11275 | 25 | CTCACTAAACATTCTACTACTCACT |
| 76 | 84R | ND4 | 11618 | 21 | GTGGCTGATTGAAGAGTATGC |
| 77 | 85F | ND4 | 11554 | 24 | CCTATGAGGCATAATTATAACAAG |
| 78 | 85R | ND4 | 11894 | 22 | ACGTGGTTACTAGCACAGAGAG |
| 79 | 86F | ND4 | 11834 | 19 | TGACTTCTAGCAAGCCTCG |
| 80 | 86R | ND4 | 12147 | 23 | ACAATCTGATGTTTTGGTTAAAC |
| 81 | 91F | ND6 | 14119 | 22 | CTCATCCTAACCCTACTCCTAA |
| 82 | 91R | ND6 | 14442 | 19 | GCGATGGCTATTGAGGAGT |
| 83 | 92F | ND6 | 14384 | 20 | GCTAACCCCACTAAAACACT |
| 84 | 92R | ND6 | 14693 | 20 | TTCATATCATTGGTCGTGGT |
| 85 | 75F | ND3 | 10007 | 25 | TAGTACCGTTAACTTCCAATTAACT |
| 86 | 75R | ND3 | 10430 | 24 | TCATAATTTAATGAGTCGAAATCA |
| 87 | 93F | ND5 | 12281 | 21 | CAGCTATCCATTGGTCTTAGG |
| 88 | 93R | ND5 | 12671 | 25 | TATTTGAAGAACTGATTAATGTTTG |
| 89 | 94F | ND5 | 12612 | 21 | AGCATTGTTCGTTACATGGTC |
| 90 | 94R | ND5 | 12944 | 21 | GGCTTGGATTAGCGTTTAGAA |
| 91 | 95F | ND5 | 12881 | 20 | TCATCCTCGCCUAGCATGA |
| 92 | 95R | ND5 | 13212 | 23 | TTTTGATGTCATUTGTGTAAGG |
| 93 | 96F | ND5 | 13156 | 23 | CAAACTCTAACACTATGCTTAGG |
| 94 | 96R | ND5 | 13519 | 20 | ATGTTTGCGGTTTCGATGAT |
| 95 | 97F | ND5 | 13458 | 20 | CATTGGCAGCCTAGCATTAG |
| 96 | 97R | ND5 | 13855 | 26 | GATTTTATTTTAAGTTTGTTGGTTAG |
| 97 | 98F | ND5 | 13795 | 19 | AAACTCACAGCCCTCGCTG |
| 98 | 98R | ND5 | 14124 | 24 | TATGTGATTAGGAGTAGGGTTAGG |

TABLE 3

OLIGONUCLEOTIDE PRIMERS CORRESPONDING TO ATP SYNTHETASE SUBUNITS 8/6 ENCODING MTDNA SEQUENCES

| SEQ. ID. NO. | PRIMER | GENE | NUCLEOTIDE POSITION (5', light strand) | PRIMER LENGTH | PRIMER SEQUENCE 5'->3' |
|---|---|---|---|---|---|
| 99 | 41F | ATPase 8 | 8292 | 23 | GCCCACTGTAAAGCTAACTTAGC |
| 100 | 41R | ATPase 8 | 8631 | 22 | TAGTCGGTTGTTGATGAGATAT |
| 101 | 41RA | ATPase 8 | 8632 | 17 | AGTCGGTTGTTGATGAG |
| 102 | 42F | ATPase 6 | 8572 | 23 | GGCCTACCCGCCGCAGTACTGAT |
| 103 | 42R | ATPase 6 | 8909 | 23 | TGTAGGTGTGCCTTGTGGTAAGA |
| 104 | 43F | ATPase 6 | 8866 | 22 | ATTATAGGCTTTCGCTCTAAGA |
| 105 | 43FA | ATPase 6 | 8806 | 21 | CCAACCACCCAACTATCTATA |
| 106 | 43R | ATPase 6 | 9214 | 22 | ATATGATAGGCATGTGATTGGT |
| 107 | 26F | ATPase 8 | 8311 | 25 | TAGCATTAACCTTTTAAGTTAAAGA |
| 108 | 26R | ATPase 8 | 8516 | 19 | TCGTTCATTTTGGTTCTCA |

As described herein, the present invention provides compositions and methods related to novel exmtDNA sequences that may differ from human mtDNA sequences at one or more nucleotide positions as disclosed in FIG. 4, such as, for ample, the exmtDNA sequences of SEQ ID NOS:1, 3 and 4. Details for obtaining SEQ ID NO:1 are provided below in the Examples. Those having ordinary skill in the art can also readily obtain other isolated exmtDNA sequences using well known methodologies including those provided herein and in the cited references, and further including the use of the oligonucleotide primers provided in Tables 1–3 and in the Examples. Databases (e.g., GenBank, EMBL) and methods for nucleic acid sequence analysis are also well known in the art, for example, similarity between two sequences may be readily determined using well known computer programs such as the BLAST algorithm (Altschul, *J. Mol. Biol.* 219:555–565, 1991; Henikoff and Henikoff, *Proc. Natl. Acad. Sci. USA* 89:10915–10919, 1992), which is available at the NCBI website http://www/ncbi.nlm.nih.gov/cgi-bin/ BLAST). Default parameters may be used. Examples of other useful computer algorithms are those used in programs such as Align and FASTA, which may be accessed, for example, at the Genestream internet website of the Institut de Genetique Humaine, Montpellier, France (www2.igh.cnrs.fr/home.eng.html) and used with default parameters.

For instance, exmtDNA sequences present in SEQ ID NOS:3 or 4 that correspond to specific regions of SEQ ID NO:2 can be readily identified, and appropriate primers selected based on the sequences provided in Tables 1–3 and the exmtDNA nucleotide substitutions and deletions relative to the corresponding human mtDNA sequence (SEQ ID NO:2) provided in FIG. 4. For example, SEQ ID NO:3 may be derived from, or detected in, a suitable biological sample using primer set 26 and/or primer set 41 as provided in Table 3, and methodologies essentially as provided in U.S. Pat. No. 5,840,493 (and references cited therein), which is hereby incorporated by reference. As another example, such an approach applied to a biological sample comprising a cloned human peripheral blood leukocyte derived genomic DNA library (Clontech, Palo Alto, Calif., catalog number HL1111j) probed with a nucleotide sequence corresponding to the region of SEQ ID NO:2 encoding ATP synthase subunit 8 may provide SEQ ID NO:4, portions of which may be useful in the subject invention compositions and methods. From the disclosure herein, as will be readily apparent to those having ordinary skill in the art, the nucleotide sequence from position 215–733 in SEQ ID NO:4 corresponds to SEQ ID NO:3, and both SEQ ID NOS:3 and 4 correspond to a portion of SEQ ID NO:2 that differs from SEQ ID NO:2 by having specific nucleotide substitutions disclosed in FIG. 4. The nucleotide sequences in SEQ ID NO:4 from positions 1–214 and 734–1263, conversely, do not correspond to mtDNA sequences of SEQ ID NO:2 and further may represent novel nucleic acid sequences. Sequence analysis (e.g., using online databases and algorithms as described above) of nucleotides 734–1263 suggests that nucleotides 963–1105 encode an exon of a human carboxypeptidase-N "L" subunit and that nucleotides 734–962 represent novel intron sequences within the carboxypeptidase-N gene, with nucleotides 1106–1263 representing additional novel (and probably non-coding) sequences as well. The exmtDNA sequence of nucleotides 215–733 thus may be present in human genomic DNA as a mtDNA-like pseudogene situated within intronic DNA.

In another particularly preferred embodiment of the invention, DNA in a biological sample containing exmtDNA and/or mtDNA is first amplified by methodologies well known in the art and described above, such that the amplification products may be used as templates in a method for quantifying the amount of exmtDNA and mtDNA present in the sample. Accordingly, it may be desirable to employ oligonucleotide primers that are complementary to target sequences that are identical in, and common to, mtDNA and exmtDNA, for example PCR amplification templates and primers prepared according to Fahy et al. (*Nucl. Acids Res.*, 25:3102, 1997) and Davis et al. (*Proc. Nat. Acad. Sci. USA* 94:4526, 1997; see also Hirano et al., *Proc. Nat. Acad. Sci. USA* 94:14894, 1997, and Wallace et al., *Proc. Nat. Acad. Sci. USA* 94:14900, 1997.)

Biological samples containing exmtDNA and mtDNA may comprise any tissue or cell preparation in which exmtDNA and mtDNA may be present. Biological samples may be provided by obtaining a blood sample, biopsy specimen, tissue explant, organ culture or any other tissue or cell preparation from a subject or a biological source. The subject or biological source may be a human or non-human animal, a primary cell culture or culture adapted cell line including but not limited to genetically engineered cell lines that may contain chromasomally integrated or episomal recombinant nucleic acid sequences, immortalized or immortalizable cell lines, somatic cell hybrid or cytoplasmic hybrid "cybrid" cell lines, differentiated or differentiatable cell lines, transformed cell lines and the like. In certain preferred embodiments of the invention, the subject or biological source may be suspected of having or being at risk for having a disease associated with altered mitochondrial function, and in certain preferred embodiments of the invention the subject or biological source may be known to be free of a risk or presence of such as disease.

In certain other preferred embodiments where it is desirable to determine whether or not a subject or biological source falls within clinical parameters indicative of Alzheimer's disease (AD), signs and symptoms of AD that are accepted by those killed in the art may be used to so designate a subject or biological source, for example clinical signs referred to in McKhann et al. (*Neurology* 34:939, 1984, National Institute of Neurology, Communicative Disorders and Stroke and Alzheimer's Disease and Related Disorders Association Criteria of Probable AD, NINCDS-ADRDA) and references cited therein, or other means known in the art for diagnosing AD.

In certain aspects of the invention, biological samples containing mtDNA and exmtDNA may be obtained from the subject or biological source before and after contacting the subject or biological source with a candidate agent, for example to identify a candidate agent capable of effecting a change in the value of the ratio r, defined above, relative to the value of r before exposure of the subject or biological source to the agent.

In a most preferred embodiment of the invention, the biological sample containing mtDNA and exmtDNA may comprise a crude buffy coat fraction of whole blood, which is known in the art to comprise further a particulate fraction of whole blood enriched in white blood cells and platelets and substantially depleted of erythrocytes. Those familiar with the art will know how to prepare such a buffy coat fraction, which may be prepared by differential density sedimentation of blood components under defined conditions, including the use of density dependent separation media, or by other methods.

In another most preferred embodiment of the invention, the amount of exmtDNA and mtDNA in a biological sample may be quantified by first heating the sample in water to lyse cells contained therein, and then extracting cellular DNA from the lysed cells using an aqueous DNA extraction procedure. "Heating" may involve treating the cells for various times, typically 1–120 minutes, at a high temperature that is at least 80° C., preferably at least 90° C., more preferably at least 95° C. and most preferably in a boiling water bath. Based on the compositions and methods disclosed in the present application, the ordinarily skilled artisan will be able to readily determine optimal times and temperatures for heating samples to practice the invention without undue experimentation. As used herein, an "aqueous DNA extraction" method refers to preparation of DNA from such a boiled cell lysate without subjecting the lysate to sodium dodecylsulfate(SDS)/proteinase K treatments and/or without fractionating the lysate using a phenol-chloroform two-phase separation extraction step. Those skilled in the art will be familiar with various standard procedures for preparing and handling DNA without the use of SDS/proteinase K and/or phenol-chloroform.

According to certain embodiments of the invention, the particular cell type or tissue type from which a biological sample is obtained may influence qualitative or quantitative aspects of the exmtDNA and/or mtDNA contained therein relative to exmtDNA and/or mtDNA obtained from distinct cell or tissue types of a common biological source. As described above, some diseases associated with altered mitochondrial function may manifest themselves in particular cell or tissue types. For example, AD is primarily a neurodegenerative disease that particularly effects changes in the central nervous system (CNS). It is therefore within the contemplation of the invention to quantify exmtDNA and mtDNA in biological samples from different cell or tissue types as may render the advantages of the invention most useful for a particular disease associated with altered mitochondrial function, and the relevant cell or tissue types will be known to those familiar with such diseases.

In order to determine whether a mitochondrial alteration may contribute to a particular disease state, it may be useful to construct a model system for diagnostic tests and for screening candidate therapeutic agents in which the nuclear genetic background may be held constant while the mitochondrial genome is modified. It is known in the art to deplete mitochondrial DNA from cultured cells to produce $\rho^0$ cells, thereby preventing expression and replication of mitochondrial genes and inactivating mitochondrial function. See, for example, International Publication Number WO 95/26973, which is hereby incorporated by reference in its entirety, and references cited therein. It is further known in the art to repopulate such $\rho^0$ cells with mitochondria derived from foreign cells in order to assess the contribution of the donor mitochondrial genotype to the respiratory phenotype of the recipient cells. Such cytoplasmic hybrid cells, containing genomic and mitochondrial DNAs of differing biological origins, are known as cybrids. "$\rho^0$ cells" are cells essentially completely depleted of mtDNA, and therefore have no functional mitochondrial respiration/electron transport activity. Such absence of mitochondrial respiration may be established by demonstrating a lack of oxygen consumption by intact cells in the absence of glucose, and/or by demonstrating a lack of catalytic activity of electron transport chain enzyme complexes having subunits encoded by mtDNA, using methods well known in the art. (See, e.g., Miller et al., *J. Neurochem.* 67:1897–1907, 1996.) That cells have become $\rho^0$ cells may befurther established by demonstrating that no mtDNA sequences are detectable within the cells. For example, using standard techniques well known to those familiar with the art, cellular mtDNA content may be measured using slot blot analysis of 1 µg total cellular DNA probed with a mtDNA-specific oligonucleotide probe radiolabeled with, e.g., $^{32}P$ to a specific activity $\geq 900$ Ci/gm. Under these conditions $\rho^0$ cells yield no detectable hybridizing probe signal. Alternatively, any other method known in the art for detecting the presence of mtDNA in a sample may be used that provides comparable sensitivity. "Mitochondrial DNA depleted" cells ("mtDNA depleted cells") are cells substantially but not completely depleted of functional mitochondria and/or mitochondrial DNA, by any method useful for this purpose. MtDNA depleted cells are preferably at least 80% depleted of mtDNA as measured using the slot blot assay described above for the determination of the presence of $\rho^0$ cells, and more preferably at least 90% depleted of mtDNA. Most preferably, mtDNA depleted cells are depleted of >95% of their mtDNA.

Mitochondria to be transferred to construct model systems in accordance with the present invention may be isolated from virtually any tissue or cell source. Cell cultures of all types may potentially be used, as may cells from any tissue. However, fibroblasts, brain tissue, myoblasts and platelets are preferred sources of donor mitochondria. Platelets are the most preferred, in part because of their ready abundance, and their lack of nuclear DNA. This preference is not meant to constitute a limitation on the range of cell types that may be used as donor sources.

For example, platelets may be isolated by an adaptation of the method of Chomyn (*Am. J. Hum. Genet.* 54:966–974, 1994). However, it is not necessary that this particular method be used. Other methods are easily substituted. For instance, if nucleated cells are used, cell enucleation and isolation of mitochondria isolation can be performed as described by Chomyn et al., *Mol. Cell. Biol.* 11:2236–2244, 1991. Human tissue from a subject suspected of having or being at risk for having a disease associated with altered mitochondrial function, or from a subject known to be free of a risk or presence of such a disease, may be the source of donor mitochondrial DNA.

After preparation of mitochondria by isolation of platelets or enucleation of donor cells, the mitochondria may be transplanted into $\rho^0$ cells or mtDNA depleted cells using any known technique for introducing an organelle into a recipient cell, including but not limited to polyethylene glycol (PEG) mediated cell membrane fusion, cell membrane permeabilization, cell-cytoplast fusion, virus mediated membrane fusion, liposome mediated fusion, particle mediated cellular uptake, microinjection or other methods known in the art. For example by way of illustration and not limitation, mitochondria donor cells ($\sim 1 \times 10^7$) are suspended in calcium-free Dulbecco's modified Eagle (DME) medium and mixed with $\rho^0$ cells ($\sim 0.5 \times 10^6$) in a total volume of 2 ml for 5 minutes at room temperature. The cell mixture is pelleted by centrifugation and resuspended in 150 µl PEG (PEG 1000, J.T. Baker, Inc., 50% w/v in DME). After 1.5 minutes, the cell suspension is diluted with normal $\rho^0$ cell medium containing pyruvate, uridine and glucose, and maintained in tissue culture plates. Medium is replenished daily, and after one week medium lacking pyruvate and uridine is used to inhibit growth of unfused $\rho^0$ cells. These or other methods known in the art may be employed to produce cytoplasmic hybrid, or "cybrid", cell lines.

As a non-limiting example, cybrid model systems may be useful for diagnosing a patient suspected of having or being at risk for a disease associated with altered mitochondrial function. According to this example, the patient's mitochondria are used to construct cybrid cells as described above. These cybrid cells may then be propagated in vitro and used to provide a biological sample for the determination of the ratio r, which can be compared to an r value calculated from samples of a control cybrid cell line constructed with mitochondria from a subject known to be free of disease. Where it may be desirable to compare the influence upon r of mitochondria from different sources, both cybrid cell lines may be constructed from the same $\rho^0$ cell line to provide a constant background environment. These and similar uses of model systems according to the invention for determining the risk for or presence of a disease associated with altered mitochondrial function will be appreciated by those familiar with the art and are within the scope and spirit of the invention.

As another non-limiting example, cybrid model systems may be useful for identifying agents suitable for treating a disease associated with altered mitochondrial function. According to this example, a cybrid cell line may be a biological source in which the ratio r is calculated as described above, before and after cybrid cells are contacted with a candidate agent for treating disease. Such a cybrid cell line may be used to screen candidate agents by identifying those agents capable of effecting a change in the value of r relative to the value of r before exposure to the agent. The present invention thus provides model systems for selecting therapeutic agents that may be suitable for the treatment of diseases associated with altered mitochondrial function. These and similar uses of model systems according to the invention for the screening and identification of agents that influence the ratio r defined above, will be appreciated by those familiar with the art and are within the scope and spirit of the invention.

In addition, although the present invention is directed primarily towards model systems for diseases in which the mitochondria have metabolic alterations, it is not so limited. Conceivably there are disorders wherein mitochondria contain structural or morphological defects or anomalies, and the model systems of the present invention are of value, for example, to find drugs that can address that particular aspect of the disease. Also, there are certain individuals that have or are suspected of having extraordinarily effective or efficient mitochondrial function, and the model systems of the present invention may be of value in studying such mitochondria. Moreover, it may be desirable to put known normal mitochondria into cell lines having disease characteristics, in order to rule out the possibility that mitochondrial alterations contribute to pathogenesis. All of these and similar uses are within the scope of the present invention, and the use of the phrase "mitochondrial alteration" herein should not be construed to exclude such embodiments.

According to the present invention, a ratio r as defined herein is determined in a biological sample, for example by calculation following quantification of mtDNA and exmtDNA using a technique based on specific oligonucleotide hybridization to a target sequence. This hybridization may be optionally followed by target template directed extension, such as in primer extension assays described herein. For certain diseases associated with altered mitochondrial function, calculation of r may have diagnostic usefulness. For example, where other clinical indicators of a disease associated with altered mitochondrial function are known, values for r in subjects known to be free of a risk or presence of such disease based on the absence of these indicators may be determined to establish a control range for r. The ratio may also be calculated in biological samples obtained from subjects suspected of having or being at risk for having a disease associated with altered mitochondrial function, and compared to the control range of r values determined in disease free subjects. Those having familiarity with the art will appreciate that there may be any number of variations on the particular subjects, biological sources and bases for comparing r values that are useful beyond those that are expressly presented herein, and these additional uses are within the scope and spirit of the invention.

For instance, determination of r in may take the form of a diagnostic assay performed on whole blood collected from a subject by routine venous blood draw, on buffy coat cells prepared from blood or on biological samples that are other cells, organs or tissue from a subject. Alternatively, in certain situations it may be desirable to construct cybrid cell lines using mitochondria from either control subjects or subjects suspected of being at risk for a disease associated with altered mitochondrial function. Such cybrids may be used to determine r for diagnostic purposes, or as biological sources for screening assays to identify agents that may be suitable for treating disease based on their ability to change the r value obtained from treated cells. In one embodiment of this aspect of the invention, therapeutic agents or combinations of agents that are tailored to effectively treat an individual patient's particular disease may be identified by routine screening of candidate agents on cybrid cells constructed with the patient's mitochondria.

The present invention provides compositions and methods that are useful in pharmacogenomics, for the classification and/or stratification of a subject or a patient population, for instance correlation of one or more traits in a subject with indicators of the responsiveness to, or efficacy of, a particular therapeutic treatment. In one aspect of the invention, measurement of r in a biological sample from a subject is combined with identification of the subject's apolipoprotein E (APOE) genotype to determine the risk for, or presence of, Alzheimer's disease (AD) in the subject. The apolipoprotein E type 4 allele (APOE-$\epsilon$4) allele is a genetic susceptibility factor for sporadic AD and confers a two fold risk for AD (Corder et al., *Science* 261:921, 1993; see also "National Institute on Aging/Alzheimer's Association Working Group Consensus Statement," *Lancet* 347:1091, 1996 and references cited therein, all of which are hereby incorporated by reference in their entireties.). Accordingly, in a preferred embodiment of the invention, the method for determining the risk for or presence of AD in a subject by comparing r values will further comprise determining the APOE genotype of the subject suspected of being at risk for AD. By using the combination of the methods for determining r, as disclosed herein, and methods known in the art for determining APOE genotype, an enhanced ability to detect the relative risk for AD is provided by the instant invention along with other related advantages. Similarly, where APOE genotype and risk for AD are correlated, the present invention provides advantageous methods for identifying agents suitable for treating AD where such agents affect r in a biological source.

As described herein, determination of r may be used to stratify an AD patient population. Accordingly, in another preferred embodiment of the invention, determination of r in a biological sample from an AD subject may provide a useful correlative indicator for that subject. An AD subject so classified on the basis of an r value may then be monitored using AD clinical parameters referred to above, such that correlation between r value and any particular clinical score used to evaluate AD may be monitored. For example, stratification of an AD patient population according to r values may provide a useful marker with which to correlate the efficacy of any candidate therapeutic agent being used in AD subjects. In a further preferred embodiment of this aspect of the invention, determination of r in concert with determination of an AD subject's APOE genotype may also be useful. These and related advantages will be appreciated by those familiar with the art.

In another aspect, the invention provides exmtDNA sequences that may be useful in the detection or regulation of telomeric events that are related to diseases, including diseases associated with altered mitochondrial function, or in the identification of agents that are suitable for the treatment of such diseases. Dynamic processes in the telomeric regions of chromosomes that involve specific nucleic acid sequences, and in particular that may involve particular nucleotide polymerase and nuclease activities, have been implicated in chromosomal events that may be related to cellular and molecular mechanisms of disease. See, for example, Fossel, *J. Amer. Med. Assoc.* 279:1732 (1998); LaBranche et al., *Nat. Genet.* 19:199 (1998); Shay. *Cancer*

J. Sci. Am. 4:526 (1998); Nowak et al., *Cancer. J. Sci. Am.* 4:148 (1998); Iwama et al., *Hum. Genet.* 102:397 (1998), all of which are hereby incorporated by reference. In one embodiment of the invention, nucleic acid sequences are provided that may be used to monitor telomeric events, including but not limited to telomerase activity. As disclosed herein, nucleic acids having exmtDNA sequences may be used to increase or decrease telomeric processes, for instance by destabilizing or stabilizing telomers. Without wishing to be bound by theory, because telomeric structure is related to cellular growth potential and/or senescence, nucleic acid based intervention in regulation of telomeric structure may provide effective means for the detection or treatment of related disease processes. The present invention provides identification of human exmtDNA sequences in human chromosomal telomeric regions, and other related advantages.

The following examples are offered by way of illustration, and not by way of limitation.

EXAMPLES

Example 1

Cloning of exmtDNA from Peripheral Blood Lymphocyte Genomic DNA Library

Peripheral blood lymphocytes were separated from the peripheral blood mononuclear cell fraction of freshly drawn venous blood from healthy human volunteers and the DNA extracted by standard techniques. Plasmid isolation, production of competent cells, transformation and manipulations using cloning vectors were performed essentially as described (Sambrook et al., *Molecular Cloning, a Laboratory Manual*, Cold Spring Harbor Laboratory Press, Cold Spring Harbor, N.Y., 1989). The human lymphocyte DNA was partially digested with HindIII and inserted into the pBeloBAC11 vector (Genome Systems, Inc., St. Louis, Mo. with insert sizes ranging from 50 kb to over 240 kb to create a human genomic library. This library was screened by PCR using the following primers, which are complementary to mtDNA sequences in the COI encoding region of SEQ ID NO:2 but have single-base substitutions at the 3' end. Details of PCR reaction conditions are provided in U.S. Pat. No. 5,565,323, which is hereby incorporated by reference, using 30 cycles instead of 25 cycles at 95° C. and with a single reaction being performed instead of five separate reactions.

5'-CCTTACACCTAGCAGGTA SEQ ID NO:5

5'-ACGCCGATGAATATGATAGC SEQ ID NO:6

A single positive clone was identified having a genomic DNA insert that included exmtDNA and was expanded, with the DNA then being purified using Magnum KB-100 columns (Genome Systems, St. Louis, Mo.). Portions of the insert were amplified with internal PCR primers complementary to human mtDNA sequences (Anderson et al., *Nature* 290:456, 1981) and sequenced using Prism DyeDeoxy terminator chemistry (Perkin-Elmer, Foster City, Calif.) according to the manufacturer's instructions. Sequence information at the junctions of exmtDNA and adjoining non-mtDNA in the positive pBeloBAC clone was obtained using the BigDye Terminator cycle sequencing kit (Perkin-Elmer) according to the supplier's recommendations. The products of sequencing reactions were purified by ethanol precipitation or by using CentriSep spin columns (Princeton Separations, Princeton, N.J.), then electrophoretically separated using an Applied Biosystems Model 373A DNA sequencing system (Applied Biosystems Division of Perkin-Elmer, Foster City, Calif.). Sequence Navigator software (Applied Biosystems) was used to analyze exmtDNA sequence data, and nucleotide insertions, deletions or substitutions were identified by comparing exmtDNA sequences to published human mtDNA sequence data. (SEQ ID NO:2, Anderson et al., *Nature* 290:456, 1981).

The insert contained the 5,840 base pair contiguous exmtDNA sequence of SEQ ID NO:1 (nucleotide positions 445–6284 in FIG. 1), which corresponded to and exhibited 98% sequence homology with nucleotide positions 3914–9755 of the human mtDNA sequence of SEQ ID NO:2. There were 89 nucleotide positions at which substitutions or deletions (2) were detected, as indicated in FIG. 4. The complete ~5.8 kb exmtDNA sequence is in a single reading frame relative to the corresponding region of the human mitochondrial genome (SEQ ID NO:2) with the exception of a two base pair deletion at nucleotide positions 8196–8197. Starting at the 5' terminus (nt 445 in FIG. 1) and proceeding in the 3' direction, the exmtDNA sequence includes DNA sequences corresponding, in order, to a truncated ND1 gene, complete ND2 and CO1 genes, a CO2 gene with the above noted two base pair deletion, complete ATP synthetase subunit 8 and ATP synthetase subunit 6 genes, interspersed tRNA genes (as indicated in FIG. 4) and a truncated CO3 gene of the published human mtDNA sequence of SEQ ID NO:2 (Anderson et al., *Nature* 290:456, 1981). The non-mitochondrial DNA sequences on either side of the 5,840 base pair exmtDNA sequence (nucleotides 1–444 and 6285–6691) did not display homology to any nuclear DNA sequences listed in the GenBank database.

Example 2

Detection of exmtDNA in Rho-0 Cells

In order to verify that presumptive exmtDNA sequences originated from nuclear and not mitochondrial DNA present in the DNA preparation from which the human genomic library was constructed, two established cell lines were depleted of mtDNA using ethidium bromide to generate $\rho^0$ cells (Miller et al., *J. Neurochem.* 67:1897, 1996) and assayed for the presence of exmtDNA sequences. Briefly, $\rho$0118/5 and 064/5 SH-SY5Y neuroblastoma cells and 0A431 epidermal carcinoma cells were produced and maintained as described (Miller et al., 1996). Cells were harvested and DNA was extracted with DNAzol (Molecular Research Center, Inc., Cincinnati, Ohio) according to the manufacturer's instructions. The recovered DNA was amplified by PCR and analyzed by primer extension assay using primers specific for a sequence within the mitochondrial COXI gene region containing the nucleotide at position 7146 of the mtDNA sequence (SEQ ID NO:2), which corresponds to a nucleotide substitution in the exmtDNA sequence. (FIG. 4 and SEQ ID NO:1) PCR primers and reaction conditions and primer extension assays were as described in Fahy et al. (*Nucl. Acids Res.* 25:3102, 1997), which is hereby incorporated by reference in its entirety. Primer extension products corresponding to a region of the exmtDNA sequence of SEQ ID NO:1 and including a nucleotide corresponding to the guanosine residue at position 7146 or its complement were detected in $\rho^0$ cells that contained no detectable mtDNA as described herein and in Miller et al. (*J. Neurochem* 67:1897, 1996).

Example 3

Absence of Detectable Transcripts of exmtDNA Sequences in RT-PCR Assay

The reverse transcription-polymerase chain reaction (RT-PCR; Rappolee et al., *Science* 241:708, 1991; Chelly et al., Nature 333:858, 1988; Brenner et al., BioTechniques 7:1096, 1989) technique was employed to determine whether the novel 5.8 kb exmtDNA sequence cloned from a human genomic DNA library is transcribed. The buffy coat fraction of freshly drawn human venous blood was prepared using Accuspin devices (Sigma, St. Louis, Mo.) according to the manufacturer's instructions and total RNA was extracted from isolated buffy coat cells with Trizol reagent (GibcoBRL, Bethesda, Md.) as recommended by the supplier. First strand cDNA was synthesized from poly-A+ mRNA using the SuperScript™ preamplification system (GibcoBRL) with oligo(dT) as primer according to the manufacturer's instructions. PCR was conducted using this cDNA as template and primers complementary to portions of the initochondrial cytochrome c oxidase subunit 2 (COII, COX2) mtDNA sequence (SEQ ID NO:2) as described in Fahy et al. (Nucl. Ac. Res. 25:3102, 1997). The corresponding region of exmtDNA (SEQ ID NO:1) contains nucleotide substitutions at positions 7650 and 7868, relative to mtDNA (FIG. 4). Amplicons were purified and analyzed by the primer extension assay as described in Fahy et al. such that readily distinguishable products are predicted depending on whether or not the primer has hybridized to a target sequence adjacent to a sequence having the substitutions. Based on quantitative analysis of fluorescent band intensities of the primer extension products, mRNA encoding human COII gene products of mtDNA (SEQ ID NO:2) was detectable, but no mRNA encoding products from the corresponding exmtDNA region of SEQ ID NO:1 was detected, indicating that the exmtDNA sequence is not expressed.

Example 4

Primer Extension Assay to Quantify exmtDNA and mtDNA

A competitive primer extension approach was used to simultaneously detect both mtDNA and exmtDNA sequences with a fluorophor-labeled primer and a selected mix of deoxynucleotides (dNTPs) and dideoxynucleotides (ddNTPs). The exmtDNA and mtDNA compete as templates in the primer extension reaction and are distinguished by differential extension of the primer. Thus, to determine the relative quantities of defined portions of mtDNA (SEQ ID NO:2) and exmtDNA (SEQ ID NO:1) using the nucleotide substitution at position 7650 (FIG. 4) with the nucleotide combination of dATP, dTTP and ddGTP, the primer is extended by one base when the template is mtDNA. When exmtDNA is present as template, the primer is extended by three bases. The proportion of numtDNA in relation to mtDNA is estimated by comparing the ratio of fluorescence intensities of the gel-separated extension products with a standard curve generated from known mtDNA/numtDNA mixtures. (Fahy et al., Nucl. Ac. Res. 25:3102, 1997)

Thermo Sequenase™, dNTPs and ddNTPs were purchased from Amersham (Cleveland, Ohio). Calf intestine alkaline phosphatase and biochemical reagents were obtained from Boehringer Mannheim (Indianapolis, Ind.) and QIAquick PCR purification kits from Qiagen (Chatsworth, Calif.). Accuspin™ Tubes and HISTO-PAQUE® 1077 were purchased from Sigma (St. Louis, Mo.) and EDTA vacutainers from Beckton Dickinson (San Jose, Calif.). UlTma™ DNA polymerase, AmpliTaq® DNA polymerase and reagents for DNA synthesis were purchased from Perkin Elmer (Foster City, Calif.). Oligonucleotides were synthesized on an Applied Biosystems 394 DNA/RNA synthesizer (Perkin Elmer) using standard phosphoramidite chemistry. 5' Fluorescein-labeled oligonucleotide primers were obtained by using the 6-FAM Amidite reagent in the last step of the automated synthesis. Tritylated and fluorescein-labeled oligonucleotides were purified by reverse phase chromatography using an acetonitrile gradient in 0.1 M triethylammonium acetate, pH 6.8 running buffer. The oligonucleotides migrated as single bands on a 15% denaturing polyacrylamide gel. The homogeneity of the fluorescein-labeled oligonucleotides was independently assessed by electrophoresis on an Applied Biosystems Model 373 Sequencing System.

After IRB approval and informed consent, fresh venous blood samples were drawn from 837 patients with clinical diagnosis of probable Alzheimer's disease (AD mean age= 74.7±1.1 years) and 191 controls (67±1 years; cognitively normal age-matched N=114; cortico-basal ganglionic degeneration N=2; Pick's disease N=1; Parkinson's disease N=24; non-insulin dependent diabetes mellitus N=29; insulin dependent diabetes mellitus N=6; Leigh's syndrome, N=2, Machado Joseph Disease N=2; idiopathic renal glycosuria N=1; progressive supranuclear palsy N=1; sporadic amyotropic lateral sclerosis N=6; familial sporadic amyotropic lateral sclerosis N=1; familial Alzheimer's disease N=2). AD patients met the National Institute of Neurological, Communicative Disorders and Stroke and Alzheimer's Diseases and Related Disorders Association (NINCDS-ADRDA) criteria of probable Alzheimer's disease (McKhann et al., Neurology 34:939, 1984).

Blood samples were collected in EDTA vacutainers and kept at 4° C. for no more than 24 h. The platelet/white blood cell fraction was isolated with Accuspin™ Tubes (Sigma Diagnostics, St. Louis, Mo.) using the following procedure. Three ml of HISTOPAQUE® 1077 (Sigma) were added to the upper chamber of each Accuspin™ Tube and the device was centrifuged at 1000 g for 30 s. Two to three ml of blood were then introduced into the upper chamber and separated by centrifugation at 1000 g for 10 min at room temperature. After centrifugation, the plasma and white blood cell layers were transferred to a new tube and the white blood cells were sedimented by centrifugation at 7,000 g for 10 min. The white cell pellet was resuspended in 0.4 ml of a solution containing 0.9% sodium chloride/1mM EDTA and stored at −80° C. until use.

Frozen white blood cells (0.2 mL) were thawed and were sedimented by centrifugation at 12,000 g for 5 min. The white cell pellet was washed twice with 0.6 ml of Dulbecco's Phosphate Buffered Saline (PBS; GibcoBRL, Bethesda, Md.) and resuspended in 0.2 ml of water. The cells were lysed by incubation in a boiling water bath for 10 min. After cooling to room temperature, the cellular debris was sedimented by centrifugation at 14,000 g for 2 min. The supernatant was transferred to a new vial and the approximate concentration of the crude DNA preparation was estimated from its $A_{260}$ absorbance. The DNA sample was stored at −80° C.

Primer extension reaction templates were prepared by PCR amplification of cellular DNA. The reactions were carried out in a total volume of 50 μl using the primer pair sets described below. Following amplification, the PCR products were analyzed by electrophoresis on a 0.8% agarose gel. Reactions for analyzing exmtDNA to mtDNA ratios contained ~1 μg of cellular DNA, 2.5 U of AmpliTaq® DNA polymerase, 20 pmol each of the light strand primer

5'-CATGCAGCGCAAGTAGGTCTACAAGAC-3' [SEQ ID NO:7]

and the heavy strand primer

5'-TGTTATGTAAAGGATGCGTAGGGATGG-3' [SEQ ID NO:8]

and 10 nmol of each dNTP in PCR buffer (10 mM Tris. HCl, pH 8.3, 50 mM KCl, 2 mM $MgCl_2$). After an initial denaturation step at 95° C. for 10 s in a Gene Amp PCR System 9600 thermal cycler (Perkin Elmer), amplification was carried out for 30 cycles under the following conditions: 95° C. for 1 min, 60° C. for 1 min, 72° C. for 1 min. After the last cycle, reaction tubes were kept at 72° C. for 4 min to ensure extension of incomplete strands to the full length 255 base pair size product.

Residual nucleotides that persisted after the PCR reaction were dephosphorylated by adding 1 unit of calf intestine alkaline phosphatase (CAP) in 5 μL of 10×CAP buffer (100 mM Tris. HCl, pH 8.3, 10 mM $MgCl_2$, 10 mM $ZnCl_2$) to the PCR reaction mixture and incubating for 30 min at 37° C. in thermal cycler. Then 1.1 μL of 0.25 M EDTA, pH 8.0 was added and the alkaline phosphatase was denatured at 75° C. for 10 min.

Double-stranded PCR products were separated from primers, nucleosides and enzymes using QIAquick™ columns (Qiagen, Chatsworth, Calif.) and the buffers provided by the manufacturer. Thus, 250 μl of buffer PB were added to the PCR reaction mixture and mixed. A Qiaquick™ spin column (Qiagen) was placed in a 2 ml collection tube and the sample was loaded. The sample was centrifuged for 30–60 s at 14000 g and the flow through was discarded. The adsorbed PCR product was washed with 750 μl of buffer PE, and eluted with 50 μl of 10 mM Tris. HCl, pH 8.5. The purified product solution was dried in a Savant SpeedVac Concentrator and then reconstituted in 20 μl of water.

The fluorescein-labeled primer for analysis of the AD-associated mutation at nucleotide position 7650 was
TATGAGGGCGTGATCATGAAAG [SEQ ID NO:9]
using dATP and dTTP plus dideoxyGTP (ddGTP) to generate primer extension products of 23 and 25 nucleotides in length from mtDNA and exmtDNA templates, respectively.

Stock solutions of each dNTP and ddNTP were prepared by mixing equimolar amounts of the nucleotides with $MgCl_2$ and diluting the mixture to the desired concentration with 10 mM Tris, 1 mM EDTA, pH 8.0 (TE). The fluorescein-labeled primers were diluted in TE to provide final stock concentrations of 40 fmol/μl. One μl of the purified PCR-amplified DNA fragment was used as template for each assay.

Primer extension reactions were performed in a total volume of 8 μL. The thermostable enzyme, UlTma™ DNA polymerase (Perkin-Elmer, Foster City, Calif.) was used in primer extension assays for analyzing exmtDNA to mtDNA ratios. The reactions contained template, 20 fmol fluorescein-labeled primer, 400 μM ddNTPs/25 μM dNTPs of the appropriate nucleotide combination and 0.6 unit of enzyme in buffer containing 10 mM Tris-HCl, pH 8.8, 10 mM KCl, 0.002% Tween 20, 2 mM $MgCl_2$. Each set of primer extension assays included control reactions with mtDNA and exmtDNA templates.

The products of the primer extension reaction were analyzed on an ABI 373 Sequencer using a 12% denaturing polyacrylamide gel and Tris borate/EDTA as running buffer. Prior to electrophoresis, the samples in loading dye were denatured for 3 min at 85° C. Three μl aliquots of the standards (primer with no added template, reaction products from control DNA templates) and each unknown reaction mixture were then loaded and electrophoresed according the manufacturer's instructions. Fluorescent band intensities associated with the primer extension products were estimated by the GENESCAN™ 672 software program (Perkin Elmer, Applied Biosystems Division). Quantitative analysis was carried out by correlating the fluorescent band intensities of mtDNA and exmtDNA-derived extension products from unknown samples with those from mtDNA and exmtDNA control templates.

Example 5

Primer Extension Assay Using DNA Isolated from Affinity Isolated Mitochondria Mitochondria were immunoaffinity isolated from cultured cells and then DNA was extracted from the isolated organelles, to determine whether detectable exmtDNA was present. Normal SH-SY5Y neuroblastoma cells, and normal and $\rho^0$ A431 epidermal carcinoma cells were produced and maintained as described (Miller et al., *J. Neurochem.* 67:1897, 1996). Cells were harvested by scraping in MSB (0.21 M mannitol, 0.07 M sucrose, 0.05 M Tris-HCl, 0.01 M EDTA, pH 7.4; $10^7$ cells/ml) and lysed by three freeze-thaw cycles. Cellular debris was removed by centrifugation at 1000×g for 5 min. The mitochondria enriched supernatants were used for subsequent immunopurification steps. The buffy coat fraction of whole blood containing white blood cells and platelets as described above was also prepared and lysed by freeze-thaw as was done with the cultured cells, to produce a mitochondrial fraction for immunopurification.

Monoclonal anti-mitochondrial antibody MAB 1273 (Chemicon International, Temecula, Calif.) was added to the mitochondria enriched fractions for 2 hr. Antibody-mitochondria complexes were isolated using a secondary antibody bound to magnetic beads (Dynal Inc., Great Neck, N.Y.) according to the manufacturer's instructions. After extensive washing of the bead-bound antibody-mitochondria complexes with PBS/0.1% BSA, mtDNA was extracted from the complexes using DNAzol reagent (Molecular Research Center, Inc., Cincinnati, Ohio) according to the manufacturer's recommendations. Quantification of mtDNA and exmtDNA was performed using the competitive primer extension assay described above in Example 4. No DNA could be amplified from the DNA extracted from immunopurified mitochondria from the $\rho^0$ A431 cell line, consistent with the depletion of mtDNA that is characteristic of the $\rho^0$ state. Primer extension results indicated that no exmtDNA sequences were present in the DNA extracted from mitochondria of blood buffy coat cells, SH-SY5Y cells or A431 cells, confirming that exmtDNA sequences are of extramitochondrial origin.

Example 6

Determination of APOE Genotype by Primer Extension Assay

Primer extension assay procedures., essentially as described above in Example 4 but with the modifications indicated here, were used to determine APOE genotype in a panel of 837 clinically diagnosed AD individuals and 191 control subjects (cognitively normal age matched individuals, patients with non-insulin dependent diabetes mellitus (NIDDM) and neurological controls). The APOE allele distribution in the AD population an controls in the study is shown in Table 4.

TABLE 4

APOE GENOTYPE DISTRIBUTION

| APOE allele | Control (N = 191) | AD (N = 837) |
| --- | --- | --- |
| 2/2 | 1 | |
| 2/3 | 16 | 33 |
| 2/4 | 3 | 22 |
| 3/3 | 112 | 295 |
| 3/4 | 56 | 403 |
| 4/4 | 3 | 84 |

DNA isolation and preparation of primer extension reaction templates by PCR were essentially as described above in Example 4, except that for APOE analysis, a modification of the protocol of Livak and Hainer (1994) was used. Thus, for template preparation by PCR each reaction contained ~1 µg of cellular DNA, 2.5 U of AmpliTaq® DNA polymerase, 20 pmol each of the forward primer 5'-GGCACGGCTGTCCAAGG-3' [SEQ ID NO: 10] and the reverse primer
5'-CCCGGCCTGGTACACTG-3' [SEQ ID NO:11]
and 10 nmol of each dNTP in PCR buffer (10 mM Tris. HCl, pH 8.3, 50 mM KCl, 1.5 mM $MgCl_2$ supplemented with 5% DMSO). After an initial denaturation step at 95° C. for 10 s in a Gene Amp PCR System 9600 thermal cycler (Perkin Elmer), amplification was carried out for 25 cycles under the following conditions: 95° C. for1 min, 55° C. for 1 min, 72° C. for 1 min. The PCR product obtained after amplification was 226 base pairs in length.

The fluorescein-labeled primers and nucleotide combinations for primer extension analysis of Apo-E alleles are shown in Table 5.

TABLE 5

| Gene | Primer Sequence (5'->3') | Size | Primer Extension Product Sizes | dNTP | ddNTP |
| --- | --- | --- | --- | --- | --- |
| APOE Codon 112 | GCGGACATGGAGGACGTG SEQ ID NO:12 | 18 | 19, 20 | T | G, C |
| APOE Codon 158 | CGATGCCGATGACCTGCAGAAG SEQ ID NO:13 | 22 | 23, 24 | T | G, C |

Thermo Sequenase™ (Amersham, Cleveland, Ohio) DNA polymerase catalyzed reactions for Apo-E allele analysis were performed with 20 fmol fluorescein-labeled primer, 25 µM each of the appropriate ddNTP/dNTP combination and 0.64 unit of enzyme in buffer containing 10 mM Tris-HCl, pH 9.5, 5 mM KCl, 0.002% Tween 20, 2 mM $MgCl_2$. Each set of primer extension assays included Apo-E allelic DNA controls. After an initial denaturation step at 95° C. for 2 min, the reaction conditions comprised 20 cycles of 95° C. for 20 s and 55° C. for 40 s. The samples were concentrated to ~1 µl by heating open reaction tubes at 94° C. for 7 min. After the concentration step, 8 µl of loading dye (0.5% blue dextran in 83% formamide/8.3 mM EDTA, pH 8.0) was added.

The products of the primer extension reaction were analyzed as described above in Example 4. The Apo-E allele composition of unknown DNA samples was deduced by comparing the electrophoretic pattern of primer extension products with those from Apo-E allele DNA standards. APOE genotype distribution is shown in Table 4.

Example 7

Correlation of exmtDNA:mtDNA Ratio with Risk for AD

Primer extension assays as described in Example 4 were used to quantify the amounts of mtDNA and exmtDNA in blood samples from a panel of 837 clinically diagnosed AD individuals and 191 control subjects (cognitively normal age matched individuals, patients with non-insulin dependent diabetes mellitus (NIDDM) and neurological controls). For each subject, a ratio r was calculated using the formula:

$$r = x/(x+y)$$

wherein
x is the amount of exmtDNA in a sample, and
y is the amount of mtDNA in the sample.

The values for r were multiplied by 100 to give ranges of values according to which the patient population was stratified as shown in Table 6. Within each stratified range, the ratio of the number of subjects diagnosed with AD (McKhann et al., *Neurology* 34:939, 1984) to the number of subjects not having AD was determined, showing a correlation of increasing r value with increasing risk for AD (Table 6).

TABLE 6

Relative Risk for AD: by r Value

| r × 100 | # of AD subjects: # of Non-AD subjects |
| --- | --- |
| >15 | 1.42 |
| >20 | 1.8 |

TABLE 6-continued

Relative Risk for AD: by r Value

| r × 100 | # of AD subjects: # of Non-AD subjects |
| --- | --- |
| >25 | 2.2 |
| >30 | 2.0 |

Example 8

Increased Predictive Value of exmtDNA:mtDNA Ratio in Subjects having at Least One APOE4 Allele Determination of the value r according to Example 7 was combined with determination of APOE genotype according to Example 6 using the patient populations characterized in Examples 6 and 7 to ascertain the relationship of APOE genotype to relative risk for AD, and to demonstrate the increased correlative value of APOE genotype combined with increasing r values with relative risk for AD. The relative risk for AD as a function of APOE genotype using the APOE alleles 2, 3 or 4 alone is shown in the bottom line of Table 7. The remainder of Table 7 shows the relative risk of AD as a function of APOE genotype and r value when subjects are stratified according to r as in Example 7. The relative risk for AD increases as a function of increasing r. In particular individuals with one APOE4 allele, and especially subjects who are homozygous for the APOE4 allele, exhibit increasing risk for AD as a function of increasing r, as shown in Table 7.

TABLE 7

Relative Risk for AD: by r value and ApoE Genotype
(# AD: #Non-AD) ApoE Genotype

| r × 100 | e2/3 | e3/3 | one e4 allele | e3/4 | e4/4 |
|---|---|---|---|---|---|
| >15 | 1.5 | 1.5 | 2.2 | 2.1 | 7.1 |
| >20 | 2.0 | 1.9 | 3.7 | 3.1 | 9.0 |
| >25 | 1.7 | 1.8 | 5.3 | 3.0 | >9.0 |
| >30 | 2.5 | 2.0 | 4.6 | 3.0 | >9.0 |
| independent of r | 0.5 | 0.6 | 1.9 | 1.7 | 6.3 |

Example 9

Identification of Agents that Alter Value of R

In this example, an agent suitable for treating AD is identified based on its ability to lower the value of r as defined above. A blood sample is obtained from a patient diagnosed with AD (McKhann et al., *Neurology* 34:939, 1984) and a ratio r is calculated using the formula:

$$r = x/(x+y)$$

wherein x is the amount of exmtDNA in a sample, and y is the amount of mtDNA in the sample, where x and y are determined using the primer extension assay as described in Example 4. The candidate agent is then administered to the patient in a quantity and for a time sufficient to impart a therapeutically beneficial effect, and blood samples are periodically collected and processed using the primer extension assay as described in Example 4 to monitor alterations in the value r. Candidate agents are subjected to preliminary characterization for toxicity, bioavailability and modes of delivery prior to administration to a patient. An agent is selected that causes a reduction in the value for r, signifying an effect on the altered mitochondrial function in the patient that may underlie the differential extractability of exmtDNA and mtDNA that contributes to r values associated with increased risk for AD.

Example 10

Detection of exmtDNA Sequences in Telomeres

In this example, fluorescence in situ hybridization (FISH) is used to localize nucleic acid sequences that are present in SEQ ID NO:1 to the telomeric region of at least one human chromosome. The methods of Cannizzaro et al. (*Methods Mol. Biol.* 75:313, 1997) and references cited therein, all of which are incorporated hereby in their entireties, are used to conduct FISH. Human cell lines are grown to confluence on coverslips and then fixed and permeabilized for FISH analysis of metaphase chromosomes. The cloned pBeloBAC insert containing SEQ ID NO:1 as described above is excised from the plasmid vector and fluorescein labeled as described, and used to probe the fixed and permeabilized cells. Metaphase cells are evaluated by fluorescent laser scanning confocal microscopy and subchromosomal localization of the fluorescent probe to telomeric regions is observed. Cytological methods are used to prepare metaphase spreads of human peripheral blood leukocytes as described in the cited references, and the chromosomes are doubly labeled using suitable reporter moieties for discerning two signals, one being quinacrine to identify each chromosome by its characteristic banding pattern and the other being the labeled SEQ ID NO:1 insert, to correlate a particular chromosome with telomeric hybridization of the insert. The nucleic acid insert of SEQ ID NO:1 is next fragmented with restriction endonucleases, and the separated fragments are labeled to generate a panel of probes representing distinct sequence portions of SEQ ID NO:1, to determine whether the portion of the insert hybridizing to telomeres corresponds to an exmtDNA sequence or a non-exmtDNA sequence present in the insert as it was cloned from the human genomic library, as described above in Example 1.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated nucleic acid comprising SEQ ID NO:1 or a complementary sequence thereto.

2. An isolated nucleic acid comprising SEQ ID NO:3 or a complementary sequence thereto.

* * * * *

UNITED STATES PATENT AND TRADEMARK OFFICE
CERTIFICATE OF CORRECTION

PATENT NO. : 6,441,149 B1
DATED : August 27, 2002
INVENTOR(S) : Corinna Herrnstadt et al.

It is certified that error appears in the above-identified patent and that said Letters Patent is hereby corrected as shown below:

<u>Title page,</u>
Item [56], References Cited, OTHER PUBLICATIONS, "DeKosky and Scheff, "Synapse Loss in Frontal Cortex Biopsies in Alzheimer's Disease: Correlation with Cognitive Serverity," *Annals of Neurology* 27(5):457-464, 1990." should read -- DeKosky and Scheff, "Synapse Loss in Frontal Cortex Biopsies in Alzheimer's Disease: Correlation with Cognitive Severity," *Annals of Neurology* 27(5):457-464, 1990. --.

"Gerbitz et al., "Mitochondria and Diabetes. Genetic, Biocheical, And Clinical Implications Of The Cellular Energy Circuit," *Diabetes* 45:113-126, 1996." should read -- Gerbitz et al., "Mitochondria and Diabetes. Genetic, Biochemical, And Clinical Implications Of The Cellular Energy Circuit," *Diabetes* 45:113-126, 1996. --.

"Hirano et al., "Apparent mtDNA heteroplamsy in Alzheimer's disease patients and in normals due to PCR amplification of nucleus-embedded mtDNA pseudogenes," *Proc. Natl. Acad. Sci. USA* 94:14894-14899, 1997." should read -- Hirano et al., "Apparent mtDNA heteroplasmy in Alzheimer's disease patients and in normals due to PCR amplification of nucleus-embedded mtDNA pseudogenes," *Proc. Natl. Acad. Sci. USA* 94:14894-14899, 1997. --.

"National Institue on Aging/Alzheimer's Association Working Group, "Apoliprotein E genotyping in Alzheimer's disease," *The Lancet* 347:1091-1095, 1996." should read -- National Institute on Aging/Alzheimer's Association Working Group, "Apoliprotein E genotyping in Alzheimer's disease," *The Lancet* 347:1091-1095, 1996.

UNITED STATES PATENT AND TRADEMARK OFFICE
CERTIFICATE OF CORRECTION

PATENT NO. : 6,441,149 B1
DATED : August 27, 2002
INVENTOR(S) : Corinna Herrnstadt et al.

It is certified that error appears in the above-identified patent and that said Letters Patent is hereby corrected as shown below:

OTHER PUBLICATIONS cont'd,
"Parfait et al., "Coamplification of Nuclear Pseudogenes and Assessment of Hetroplasmy of Mitochondrial DNA Mutations," *Biochemical and Biophysical Research Communications 247*:57-59, 1998." should read -- Parfait et al., "Coamplification of Nuclear Pseudogenes and Assessment of Heteroplasmy of Mitochondrial DNA Mutations," *Biochemical and Biophysical Research Communications 247*:57-59, 1998. --.

Signed and Sealed this

Eighteenth Day of February, 2003

JAMES E. ROGAN
*Director of the United States Patent and Trademark Office*